(12) United States Patent
Makarov et al.

(10) Patent No.: US 10,208,338 B2
(45) Date of Patent: Feb. 19, 2019

(54) ENHANCED ADAPTOR LIGATION

(71) Applicant: SWIFT BIOSCIENCES, INC., Ann Arbor, MI (US)

(72) Inventors: Vladimir Makarov, Ann Arbor, MI (US); Julie Laliberte, Ypsilanti, MI (US)

(73) Assignee: SWIFT BIOSCIENCES, INC., Ann Arbor, MI (US)

( * ) Notice: Subject to any disclaimer, the term of this patent is extended or adjusted under 35 U.S.C. 154(b) by 136 days.

(21) Appl. No.: 15/122,980

(22) PCT Filed: Mar. 3, 2015

(86) PCT No.: PCT/US2015/018557
§ 371 (c)(1),
(2) Date: Sep. 1, 2016

(87) PCT Pub. No.: WO2015/134552
PCT Pub. Date: Sep. 11, 2015

(65) Prior Publication Data
US 2017/0088887 A1    Mar. 30, 2017

Related U.S. Application Data

(60) Provisional application No. 61/952,854, filed on Mar. 13, 2014, provisional application No. 61/947,235, filed on Mar. 3, 2014.

(51) Int. Cl.
| | |
|---|---|
| *C12Q 1/68* | (2018.01) |
| *C12Q 1/6855* | (2018.01) |
| *C12Q 1/6806* | (2018.01) |
| *C12N 9/12* | (2006.01) |
| *C12N 9/00* | (2006.01) |

(52) U.S. Cl.
CPC ......... *C12Q 1/6855* (2013.01); *C12N 9/1252* (2013.01); *C12N 9/93* (2013.01); *C12Q 1/6806* (2013.01); *C12Y 207/07007* (2013.01); *C12Y 605/01001* (2013.01)

(58) Field of Classification Search
None
See application file for complete search history.

(56) References Cited

U.S. PATENT DOCUMENTS

2011/0224105 A1* 9/2011 Kurn .................. C12P 19/34
506/26

* cited by examiner

*Primary Examiner* — Stephanie K Mummert
(74) *Attorney, Agent, or Firm* — Matthew S. Gibson; Ryan P. Cox; Reed Smith LLP

(57) ABSTRACT

The present disclosure describes a method of adapter ligation to the ends of fragmented double-stranded DNA molecules.

7 Claims, 71 Drawing Sheets
Specification includes a Sequence Listing.

Fill-in adapter contains oligonucleotides 12-900 and 13-426

12-900
AATGATACGGCGACCACCGAGATCTACACTCTTTCCCTACACGACGCTCTTCCGATCT -OH 3'
             /3SpC3/ TCTAGCCGAGGTGTGAGA -OH-5'
                     13-426

3' Adapter: 1st oligonucleotide 13-340 and 2nd oligonucleotide option 1 (a blocking 3' deoxythymidine base at the 3' terminus) 13-559

13-340
/5PHOS/AGATCGGAAGAGCGTCGTGTAGGGAAAGAGTGTAGATCTCGGTGGTCGCCGTATCATT/3SpC3/
       TCTAGCCTTCTCGCAGCACA
       13-559

3' Adapter: 1st oligonucleotide 13-340 and 3'Adapter: 2nd oligonucleotide option 2 (a phosphate group at the 3' terminus) 13-558

13-340
/5PHOS/AGATCGGAAGAGCGTCGTGTAGGGAAAGAGTGTAGATCTCGGTGGTCGCCGTATCATT/3PHOS/
       TCTAGCCTTCTCGCAGCACA
       13-558

FIG. 30

FAM substrate A composed of oligonucleotides 13-562 and 13-563, where the FAM group labels ligation to the 5' Phosphate of the substrate 13-562
/5Phos/TGTACCTCACTTCTCATCACTGCT/3Fam/
3' HO-ACACATGGAGTGAAGAGTAGTGACGA 13-563

FAM substrate B composed of oligonucleotides 13-561 and 13-564, where the FAM group labels ligation to the 3' OH of the substrate and where the corresponding 5' terminus of the substrate has a phosphate 13-561
/5Fam/AGCAGTGATGAAGAAGTGAGGTACA-OH 3'
/5Phos/TGTACCTCACTTCTCATCACTGCT 13-564

FAM substrate C composed of oligonucleotides 13-560 and 13-564, where the FAM group labels ligation to the 3' OH of the substrate and where the corresponding 5' terminus of the substrate lacks a phosphate 13-560
5' OH-TGTACCTCACTTCTCATCACTGCT
3' HO-ACATGGAGTGAAGAGTAGTGACGA/5Fam/

Fill-in adapter contains oligonucleotides 13-489 and 13-426

13-489
/5SpC3/A*A*TGATACGGCGACCACCGAGATCTACACTCTTTCCCTACACGACGCTCTTCCGATCT
                                                  AGATGTGAAAGGGATGTGCTGCGAGAAGGCTAG 5'
                                                  /3SpC3/
                                                  13-426

3'Adapter; 1st oligonucleotide 13-340 and 2nd oligonucleotide option 1 (containing a blocking 3' deoxythymidine base at the 3' terminus) 13-559

13-340
/5PHOS/AGATCGGAAGAGCGTCGTGTAGGGAAAGAGTGTAGATCTCGGTGGTCGCCGTATCATT/3SpC3/
                                    ACACGACGCTCTTCCGATCT/idT/ 5'
                                    13-559

FIG. 32

"P7 adapter"

3' Adapter; 1st oligonucleotide 13-501

/5PHOS/AGATCGGAAGAGCACACGTCTGAACTCCAGTCACGATCTCGTATGCCGTCTTCTGCT*T*G/3SpC3/

3' Adapter; 2nd oligonucleotide 13-712

/5Phos/AGATCGGAAGAGCACACGT*C*T₅/

"P5 adapters"

5' adapter oligonucleotide for nick-translation (13-489)

/5SpC3/A*A*TGATACGGCGACCACCGAGATCTACACTCTTTCCCTACACGACGCTCTTCCGATCT

5' adapter oligonucleotide for displacement-cleavage (13-595)

/5SpC3/A*A*TGATACGGCGACCACCGAGATCTACACTCTTTCCCTACACGACGCTCTTCCGATCTN

FIG. 37

"P7 adapter"

3' Adapter; 1st oligonucleotide 13-510

/5PHOS/AGATCGGAAGAGCACACGTCTGAACTCCAGTCACGCCAATATCTCGTATGCCGTCTTCTGCT*T*G/3SpC3/

3' Adapter; 2nd oligonucleotide 13-712

AGACGTCACTGGAGTTCAAGCT 5'

"P5 adapters"

5' adapter oligonucleotide for nick-translation (13-489)

/5SpC3/A*A*TGATACGGCGACCACCGAGATCTACACTCTTTCCCTACACGACGCTCTTCCGATCT

FIG. 38

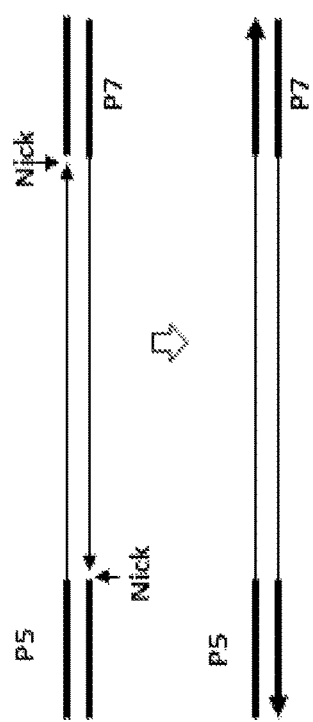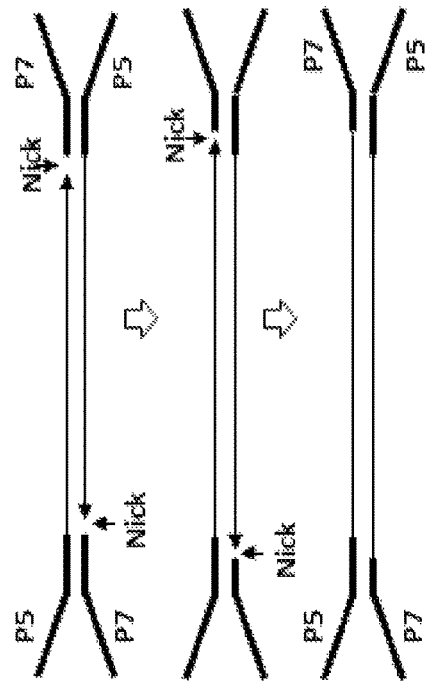
FIG. 40

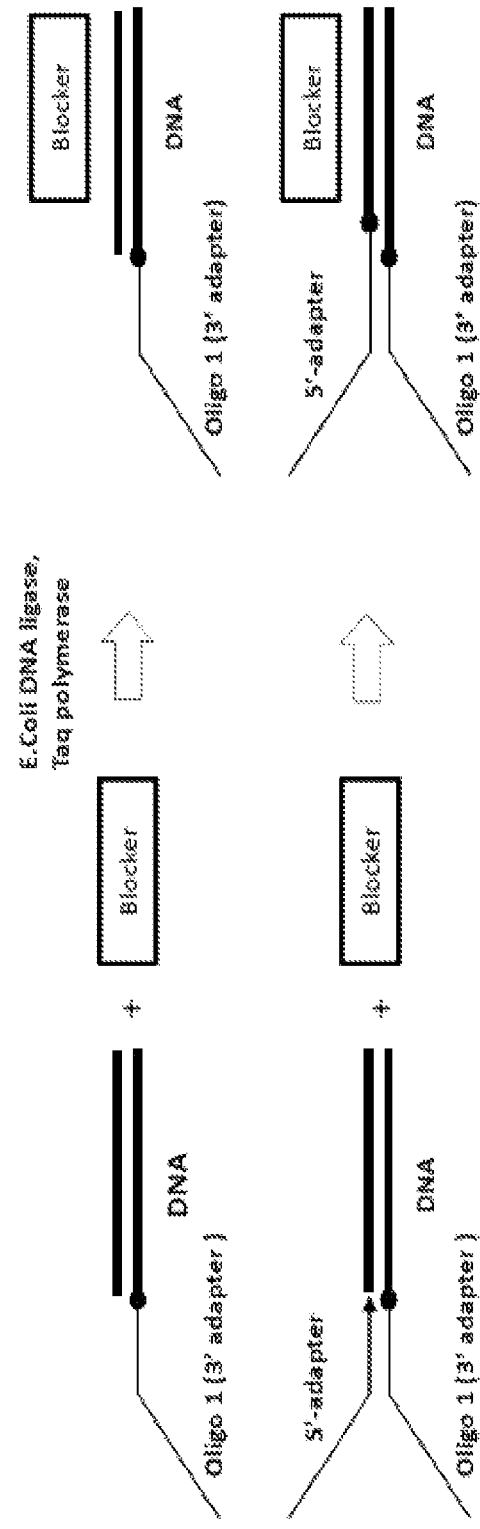
FIG. 46

ENHANCED ADAPTOR LIGATION

CROSS REFERENCE TO RELATED APPLICATIONS

This application claims the priority benefit under 35 U.S.C. § 119(e) of Provisional U.S. Patent Application No. 61/947,235, filed Mar. 3, 2014, and Provisional U.S. Patent Application No. 61/952,854, filed Mar. 13, 2014, the disclosure of each of which is incorporated herein by reference in its entirety.

INCORPORATION BY REFERENCE OF MATERIALS SUBMITTED ELECTRONICALLY

This application contains, as a separate part of disclosure, a Sequence Listing in computer readable form (Filename: 48485A_Seqlisting.txt; created Mar. 3, 2015; 8,776 bytes), which is incorporated herein by reference in its entirety.

BACKGROUND

All commercially available next-generation sequencing (NGS) technologies require library preparation, whereby a pair of specific adapter sequences are ligated to the ends of DNA fragments in order to enable sequencing by the instrument. Most NGS adapters comprise three functional domains: (1) unique PCR primer annealing sequences for library and clonal amplification, (2) unique sequencing primer annealing sequences and (3) unique sample indexing sequences. Currently, most platforms utilize clonal amplification to make hundreds of copies of each individual DNA library molecule. This is achieved by bridge amplification or emulsion PCR for the purpose of amplifying the signal generated for the particular mode of sequence detection for each library molecule (e.g. fluorescence or pH). For sequencing by synthesis, annealing domains for sequencing primers are juxtaposed to the adapter-insert junctions; to enable paired-end sequencing, each adapter possesses a unique sequence for primer annealing. Sample index sequences are comprised of short unique sequences, typically 6-8 bases, that when sequenced, identify the sample source of a particular sequence read, enabling samples to be multiplexed or co-sequenced. There are existing and emerging single molecule sequencing technologies that do not rely on clonal amplification for signal detection but still require the attachment of adapter sequences to their termini for other purposes, such as adding a terminal hairpin-loop to DNA duplexes to enable sequencing of both strands as a single molecule or introducing a leader sequence for nanopore entry.

Typically, preparation of an NGS DNA library involves 5 steps: (1) DNA fragmentation, (2) polishing, (3) adapter ligation, (4) size selection, and (5) library amplification (See FIGS. 1 and 2).

(1) Fragmentation: Fragmentation of DNA can be achieved by enzymatic digestion or physical methods such as sonication, nebulization or hydrodynamic shearing. Each fragmentation method has its advantages and limitations. Enzymatic digestion produces DNA ends that can be efficiently polished and ligated to adapter sequences. However, it is difficult to control the enzymatic reaction and produce fragments of predictable length. In addition, enzymatic fragmentation is frequently base-specific thus introducing representation bias into the sequence analysis. Physical methods to fragment DNA are more random and DNA size distribution can be more easily controlled, but DNA ends produced by physical fragmentation are damaged and the conventional polishing reaction is insufficient to generate ample ligation-compatible ends.

(2) Polishing: Typical polishing mixtures contain T4 DNA polymerase and T4 polynucleotide kinase (PNK). The 5'-3' polymerase and the 3'-5' exonuclease activities of T4 DNA polymerase excise 3' overhangs and fill-in 3' recessed ends, which results in excision of damaged 3' bases as well as polishing (creation of blunt) DNA ends. The T4 polynucleotide kinase in the polishing mix adds a phosphate to the 5' ends of DNA fragments that can be lacking such, thus making them ligation-compatible to NGS adapters.

What has remained unknown in the art is that a significant number of 5' ends produced by physical fragmentation are damaged in an unidentified manner and do not get phosphorylated by PNK. There is no enzyme in a conventional polishing mix that can trim a damaged 5' terminal base. As a result, a substantial fraction of DNA fragments in the preparation do not get converted into NGS library molecules because they remain ligation incompatible at their 5' termini to NGS adapters. Although it is known in the art that adapter ligation is inefficient, ligation is typically performed on both strands simultaneously so it has remained unknown which strand is limiting. We separated the reactions into strand-specific ligation to test the efficiency of each, respectively. Through this analysis, we were able to pinpoint the rate limiting step in the overall process to the 5' termini which, for a significant fraction of the DNA fragments, are poor substrates for PNK and as a result, adapter ligation.

(3) Adapter Ligation: Another factor that contributes to low NGS library yield apart from a lack of 5' phosphate groups is the ligation reaction itself. Prior to ligation, adenylation of repaired DNA using a DNA polymerase which lacks 3'-5' exonuclease activity is often performed in order to minimize chimera formation and adapter-adapter (dimer) ligation products. In these methods, single 3' A-overhang DNA fragments are ligated to single 5' T-overhang adapters, whereas A-overhang fragments and T-overhang adapters have incompatible cohesive ends for self-ligation. However, the adenylation reaction is incomplete and generates non-specific side products, further reducing the number of available molecules for ligation which reduces library yield. A more efficient, alternative approach to minimize concatamer formation is presented herein.

(4) Size Selection: The size selection process also impacts library yield. During size selection, fragments of undesired size are eliminated from the library using gel or bead-based selection in order to optimize the library insert size for the desired sequencing read length. This maximizes sequence data output by minimizing overlap of paired end sequencing that occurs from short DNA library inserts. In the case of samples with extremely limited input quantities, this step can be skipped, and in exchange for a higher degree of paired-end overlap, more rare fragments are sequenced.

(5) Amplification: The problem of low library yield results in the necessity to amplify libraries by PCR prior to NGS analysis, which leads to loss of library complexity and introduction of base composition bias. The only current solution to avoid this problem is higher quantities of input DNA for library prep, but up to 20% of clinical samples submitted for NGS analysis have insufficient DNA quantity, so instead, additional PCR cycles are applied to overcome the insufficient DNA input. This results in reduced sequence data from the presence of an unacceptable percentage of PCR duplicates.

SUMMARY OF THE INVENTION

To address some of the existing problems described above which cause low yields for NGS library construction, we introduce an enhanced adapter ligation method. This novel method overcomes the necessity to add a phosphate group to the 5' ends of DNA fragments (which is required for conventional adapter ligation; see FIGS. 1 and 2). Instead, the 5' terminal bases that are damaged as a result of physical fragmentation of the DNA, are removed. By removal of the damaged base, a ligation compatible base with a 5' phosphate is exposed and adapter ligation efficiency is restored, leading to a significant increase in library yield and the ability to construct libraries from reduced input DNA quantities. In addition, an alternative to adenylation/TA ligation for the prevention of chimeric library inserts (concatamer formation during ligation) and formation of adapter dimer ligation products is introduced, which also contributes to higher library preparation yields.

This method, in its exemplary form, is comprised of 4 separate incubations (see FIGS. 3, 4 and 5) to generate a processed substrate molecule. In the first incubation, double-stranded fragmented DNA is combined with a phosphatase enzyme and under appropriate reaction conditions, the enzyme removes phosphate groups from the termini of the DNA fragments. This prevents chimeric library inserts from being generated by preventing DNA fragment concatamer formation in the subsequent ligation reactions.

In the second incubation, the de-phosphorylated DNA fragments are combined with a polymerase or a cocktail of polymerases that possess 3'-5' exonuclease activity. Under appropriate reaction conditions and in the presence of dNTPs, damaged 3' bases are trimmed and polishing of the double-stranded DNA fragments is achieved by excision of 3' overhangs and filling in of 3' recessed ends that were generated during physical fragmentation. At the completion of this step, the DNA fragments possess blunt ends with ligation compatible 3' termini and 5' termini which lack phosphate groups, therefore rendering the DNA fragments incapable of self-ligation.

In the third incubation, the blunt ended, double-stranded DNA fragments are combined with a DNA ligase and a first double-stranded blunt ended NGS adapter (3' adapter) that comprises a 5' phosphate and which is capable of ligating to the 3' ends of the DNA fragments (see FIG. 3). The special feature of this 3' adapter is that the adapter DNA strand that would typically simultaneously ligate to the 5' end of the DNA fragments has a 3' end modification that prevents ligation, and therefore a nick remains at the junction of the 5' terminus of each DNA fragment and the 3' end of the 3' adapter following the ligation reaction even in the presence of the 5' phosphate. The same 3' modification that prevents ligation to the 5' termini of the DNA fragments also prevents adapter-adapter ligation products from forming, albeit they would be comprised of a single adapter sequence which would not be a functional adapter dimer (functional dimers are comprised of both adapters). The product of this step is double-stranded DNA fragments with a single NGS adapter ligated to only one strand on both 3' termini.

In the fourth incubation, the strand of the 3' adapter that remains unligated to the DNA fragments (due to the 3' modification) is also displaceable or degradable due to the incorporation of degradable bases during oligo synthesis. In the presence of an optional, appropriate enzyme during the fourth incubation, the 3' adapter strand is degraded or is displaced by a new single-stranded adapter comprising the second NGS adapter sequence that is also present in the reaction (5' adapter, see FIG. 3), and through a complementary sequence to the 3' adapter at the junction of the adapter-insert, the single-stranded 5' adapter anneals to the complementary portion of the 3' adapter that is ligated to the 3' ends of the double-stranded DNA fragments, resulting in the restoration of a nick or gap. Additionally in the reaction is a DNA polymerase that possesses 5'-3' exonuclease activity, and in the presence of dNTPs, a ligase and the appropriate reaction conditions, nick translation is initiated at the nick or gap residing at the junction of the 5' adapter and the 5' termini of the DNA fragments. Nick translation results in replacement of the damaged 5' terminal base (and an additional one or more bases internal to the 5' terminus) and exposes a ligation-compatible 5' terminal phosphate group. Subsequently, efficient ligation of the 5' adapter to the DNA substrate molecule occurs when ligase seals the nick that is translated one or more bases (see FIG. 4). At the completion of this novel adapter ligation process, both ends of each double-stranded DNA fragment are flanked by two different, single-stranded NGS adapters that share a short complementary adapter sequence at the adapter-insert junction.

Alternatively, removal of the 5' terminal base and 5' adapter ligation can be achieved without polymerization, by annealing the single-stranded 5' adapter with one or more additional random bases at its 3' terminus which overlaps with the damaged 5' base(s) of the substrate molecule, and in the absence of dNTPs, cleavage of the displaced base at the 5' terminus of DNA substrate molecules by a 5' flap-specific nuclease occurs following displacement, which results in efficient ligation of the second NGS adapter to the exposed 5' phosphate on the termini of the cleaved DNA substrate molecules (see FIG. 5).

In another alternative, 5' terminal base removal and 5' adapter ligation can be achieved by a single dideoxy base extension from the degradable or displaceable strand of the 3' adapter that is followed by cleavage of the 5' terminal base of the DNA fragments by the 5' flap endonuclease activity of the polymerase. The strand is then degraded or displaced by the 5' adapter, and in the presence of a ligase, the 5' adapter efficiently ligates to the exposed 5' phosphate on the DNA fragments. Alternative embodiments of this step and preceding steps are presented below.

Accordingly, in one aspect the disclosure provides a method of producing a processed substrate molecule, the method comprising (i) ligating a first polynucleotide to a 3' terminus of a substrate molecule that is at least partially double stranded; (ii) annealing a second polynucleotide to the first polynucleotide under conditions that promote the annealing; (iii) excising at least one nucleotide from the 5' terminus of the substrate molecule; and then (iv) ligating the second polynucleotide to the 5' terminus of the double stranded substrate molecule to produce the processed substrate molecule. In one embodiment, the method further comprises the step, prior to step (i), of contacting the substrate molecule with a phosphatase enzyme. In another embodiment, the method further comprises the step of making the substrate molecule blunt-ended by contacting the substrate molecule with a polymerase enzyme possessing 3'-5' exonuclease activity. In yet another embodiment, the method further comprises the step of contacting the substrate molecule with a template-independent polymerase to adenylate the 3' end of the substrate molecule.

In any of the methods disclosed herein, it is contemplated that the substrate molecule is naturally occurring or the substrate molecule is synthetic. In one embodiment, the substrate molecule is naturally occurring. In another embodiment, the substrate molecule is genomic DNA, and in further embodiments the genomic DNA is eukaryotic or prokaryotic. In embodiments in which the substrate molecule is genomic DNA, the disclosure contemplates that the genomic DNA is fragmented in vitro or in vivo. In some embodiments, the in vitro fragmenting is performed by a process selected from the group consisting of shearing, cleaving with an endonuclease, sonication, heating, irradiation using an alpha, beta, or gamma source, chemical cleavage in the presence of metal ions, radical cleavage, and a combination thereof. In some embodiments, the in vivo fragmenting occurs by a process selected from the group consisting of apoptosis, radiation, and exposure to asbestos.

The disclosure also contemplates embodiments in which the substrate molecule is synthetic and is selected from the group consisting of cDNA, DNA produced by whole genome amplification, primer extension products comprising at least one double-stranded terminus, and a PCR amplicon.

In any of the aspects or embodiments of the disclosure, it is contemplated that the first polynucleotide is at least partially double stranded and comprises oligonucleotide 1 and oligonucleotide 2. In some embodiments, the second polynucleotide anneals to oligonucleotide 1, and in further embodiments, the annealing results in a nick, a gap, or an overlapping base between the second polynucleotide and the substrate molecule. In some embodiments, the annealing results in dehybridization of oligonucleotide 1 and oligonucleotide 2.

The second polynucleotide, in various embodiments, is contacted with a polymerase, resulting in degradation of oligonucleotide 2.

Also contemplated by the disclosure are embodiments wherein oligonucleotide 2 comprises a base that is susceptible to degradation, and the disclosure also provides embodiments wherein oligonucleotide 2 comprises a blocking group at its 3' end that prevents ligation. In some embodiments, the second polynucleotide comprises a modified base.

In further embodiments, a method of the disclosure further comprises (i) ligating a third polynucleotide to a 3' terminus of an additional substrate molecule that is at least partially double stranded; (ii) annealing a fourth polynucleotide to the third polynucleotide under conditions that promote the annealing; (iii) excising at least one nucleotide from the 5' terminus of the additional substrate molecule; and then (iv) ligating the fourth polynucleotide to the 5' terminus of the double stranded additional substrate molecule to produce a processed additional substrate molecule. In some embodiments, the first polynucleotide and the third polynucleotide are the same. In some embodiments, the second polynucleotide and the fourth polynucleotide are the same.

In another aspect, the disclosure provides a method of producing a processed substrate molecule, the method comprising (i) ligating a polynucleotide 1 to a 5' terminus of a substrate molecule that is at least partially double stranded; (ii) annealing a polynucleotide 2 to polynucleotide 1 under conditions that promote the annealing; (iii) excising at least one nucleotide from the 5' terminus of the polynucleotide 2; and then (iv) ligating polynucleotide 2 to the 3' terminus of the double stranded substrate molecule to produce the processed substrate molecule.

Adapter-dimers represent a serious problem in NGS library construction, especially when dealing with ultra-low DNA input quantities in the picogram range. At such low DNA input levels, adapter dimers can constitute a majority of the NGS library molecules formed, thus reducing the amount of useful information generated by DNA sequencing. For this reason, suppression of adapter dimer formation during library construction is a very important but challenging task.

There are several ways to reduce adapter dimer formation in the sequential adapter ligation NGS library preparation described herein, including:
1. More stringent purification step (SPRI) after 3' adapter ligation to remove non-ligated 3' adapter molecules, prior to the second ligation of the 5' adapter (existing approach of sequential adapter ligation separated by a SPRI cleanup)
2. Use of A-tailed DNA and T-overhang adapters (existing approach in many library protocols).
3. Alkaline phosphatase treatment after 3' adapter ligation (before SPRI) to remove 5' phosphate group from the 3' adapter to render any carryover 3' adapter to be ligation incompatible and inert in the 5' adapter ligation step (novel method disclosed herein)
4. Use of adapter-dimer blockers during 5' adapter ligation to specifically inhibit adapter dimer formation while not interfering with the desired reaction of 5' adapter ligation to the substrate molecule (methods as disclosed herein).

In further aspects the disclosure provides a composition comprising a polymerase possessing nick translation activity, a ligase and a partially double stranded adapter comprising oligonucleotide 1 and oligonucleotide 2; wherein oligonucleotide 1 comprises a 5' phosphate; and wherein the 5' portion of oligonucleotide 1 is complementary to the 3' portion of oligonucleotide 2, and wherein the 3' portion of oligonucleotide 1 is not complementary to the 5' portion of oligonucleotide 2. In some embodiments, the polymerase is Taq polymerase or DNA Polymerase I and the ligase is E. coli DNA ligase or T4 DNA ligase.

In related aspects, a method of producing a processed substrate molecule is provided, the method comprising (i) annealing oligonucleotide 1 and 2 where the 5' portion of oligonucleotide 1 is complementary to the 3' portion of oligonucleotide 2; (ii) ligating the 5' terminus of oligonucleotide 1 of the duplex created in (i) to a 3' terminus of a substrate molecule that is at least partially double stranded; (iii) excising at least one nucleotide from the 5' terminus of the substrate molecule; and then (iv) ligating the 3' terminus of oligonucleotide 2 of the duplex created in (i) to the 5' terminus of the double stranded substrate molecule to produce the processed substrate molecule. In some embodiments, the 5' end of oligonucleotide 1 includes a phosphate group. In further embodiments, oligonucleotide 1 and 2 comprise non-complementary regions at the 3' portion of oligonucleotide 1 and the 5' portion of oligonucleotide 2. The disclosure also provides, in various embodiments, that the method further comprises the step, prior to step (i), of contacting the substrate molecule with a phosphatase enzyme. In some embodiments, the method further comprises the step of making the substrate molecule blunt-ended by contacting the substrate molecule with a polymerase enzyme possessing 3'-5' exonuclease activity. In still further embodiments, the method further comprises the step of contacting the substrate molecule with a template-independent polymerase to adenylate the 3' end of the substrate molecule.

In various embodiments, the substrate molecule is naturally occurring or the substrate molecule is synthetic. In related embodiments, the substrate molecule is naturally occurring. In further embodiments, the substrate molecule is genomic DNA. In further embodiments, the genomic DNA is eukaryotic or prokaryotic. In still further embodiments, the genomic DNA is fragmented in vitro or in vivo. In related embodiments, the in vitro fragmenting is performed by a process selected from the group consisting of shearing, cleaving with an endonuclease, sonication, heating, irradiation using an alpha, beta, or gamma source, chemical cleavage in the presence of metal ions, radical cleavage, and a combination thereof. In some embodiments, the in vivo fragmenting occurs by a process selected from the group consisting of apoptosis, radiation, and exposure to asbestos. In additional embodiments, the substrate molecule is synthetic and is selected from the group consisting of cDNA, DNA produced by whole genome amplification, primer extension products comprising at least one double-stranded terminus, and a PCR amplicon. In various embodiments, there is a nick or a gap between oligonucleotide 2 and the substrate molecule after ligation to oligonucleotide 1. In some embodiments, the method further comprises the step of contacting the substrate molecule with a polymerase possessing 5'-3' exonuclease activity and a ligase. In additional embodiments, the method further comprises the step of providing a deoxynucleotide triphosphate.

In further aspects, the disclosure provides a composition comprising a polymerase possessing nick translation activity, a ligase and a partially double stranded adapter comprising oligonucleotide 1 and oligonucleotide 2; wherein oligonucleotide 1 lacks a 5' phosphate; and wherein the 5' portion of oligonucleotide 1 is complementary to the 3' portion of oligonucleotide 2, and wherein the 3' portion of oligonucleotide 1 is not complementary to the 5' portion of oligonucleotide 2. In some embodiments, the polymerase is Taq polymerase or DNA Polymerase I and the ligase is *E. coli* DNA ligase or T4 DNA ligase.

In some aspects, a method of producing a processed substrate molecule is provided, the method comprising (i) annealing oligonucleotide 1 and 2 where the 5' portion of oligonucleotide 1 is complementary to the 3' portion of oligonucleotide 2; (ii) ligating the 3' terminus of oligonucleotide 2 of the duplex created in (i) to a 5' terminus of a substrate molecule that is at least partially double stranded; (iii) excising at least one nucleotide from the 5' terminus of oligonucleotide 1; and then (iv) ligating the 3' terminus of the substrate molecule to the 5' terminus of oligonucleotide 1 of the duplex created in (i) to produce the processed substrate molecule. In some embodiments, the 5' end of oligonucleotide 1 lacks a phosphate group. In further embodiments, oligonucleotide 1 and 2 comprise non-complementary regions at the 3' portion of oligonucleotide 1 and the 5' portion of oligonucleotide 2. In still further embodiments, the method further comprises the step of contacting the substrate molecule with a polynucleotide kinase to add a phosphate group to the 5' end of the substrate molecule. In still further embodiments, the method further comprises the step of making the substrate molecule blunt-ended by contacting the substrate molecule with a polymerase enzyme possessing 3'-5' exonuclease activity. In yet additional embodiments, the method further comprises the step of contacting the substrate molecule with a template-independent polymerase to adenylate the 3' end of the substrate molecule. In various embodiments, the substrate molecule is naturally occurring or the substrate molecule is synthetic. In related embodiments, the substrate molecule is naturally occurring. In some embodiments, the substrate molecule is genomic DNA, and in further embodiments the genomic DNA is eukaryotic or prokaryotic. In further embodiments, the genomic DNA is fragmented in vitro or in vivo. In still further embodiments, the in vitro fragmenting is performed by a process selected from the group consisting of shearing, cleaving with an endonuclease, sonication, heating, irradiation using an alpha, beta, or gamma source, chemical cleavage in the presence of metal ions, radical cleavage, and a combination thereof. In some embodiments, the in vivo fragmenting occurs by a process selected from the group consisting of apoptosis, radiation, and exposure to asbestos. In further embodiments, the substrate molecule is synthetic and is selected from the group consisting of cDNA, DNA produced by whole genome amplification, primer extension products comprising at least one double-stranded terminus, and a PCR amplicon. In some embodiments, there is a nick or a gap between oligonucleotide 1 and the substrate molecule after ligation to oligonucleotide 2. In some embodiments, the method further comprises the step of contacting the substrate molecule with a polymerase possessing 5'-3' exonuclease activity and a ligase. In some embodiments, the method further comprises the step of providing a deoxynucleotide triphosphate.

In some aspects of the disclosure, a composition is provided comprising a ligase and a first polynucleotide that is at least partially double stranded and comprises oligonucleotide a and oligonucleotide b; wherein oligonucleotide a lacks a 5' phosphate; and wherein oligonucleotide a (i) comprises a base that is susceptible to degradation. In some embodiments, the base that is susceptible to degradation is deoxyuridine, a ribonucleotide, deoxyinosine, or inosine. In further embodiments, oligonucleotide a comprises a base modification that reduces the binding stability of oligonucleotide a, wherein the base modification is deoxyinosine, inosine or a universal base.

In additional aspects, the disclosure provides a composition comprising a ligation product resulting from incubation of a double stranded substrate with a composition of the disclosure; a ligase, a DNA polymerase having nick translation activity, an endonuclease that recognizes a base that is susceptible to degradation, and a second polynucleotide that is single stranded and comprises a 5' domain that is sufficiently complementary to the 3' portion of oligonucleotide b of the first polynucleotide to anneal under appropriate conditions when oligonucleotide a of the first polynucleotide is either degraded or displaced. In some embodiments, the second polynucleotide is of a sufficient length to displace oligonucleotide a of the first polynucleotide or the second polynucleotide comprises a base modification that increases its binding stability. In further embodiments, the endonuclease is selected from the group consisting of UDG plus endonuclease VIII, RNase HI, RNase H2 and Endonuclease V. In some embodiments, the ligase is *E. coli* DNA ligase or T4 DNA ligase and the polymerase possessing nick translation activity is Taq polymerase or DNA Polymerase I. In still further embodiments, the base modification that increases its binding stability is a locked nucleic acid (LNA).

In further aspects, the disclosure provides a composition comprising a ligation product resulting from incubation of a double stranded substrate with a composition of the disclosure; a ligase; a flap endonuclease; an endonuclease that recognizes a base that is susceptible to degradation; a second polynucleotide comprising a single stranded oligonucleotide comprising a 5' domain that is sufficiently complementary to the 3' portion of oligonucleotide b of the first polynucleotide to anneal under appropriate conditions when oligonucleotide a of the first polynucleotide is either degraded or displaced, wherein the second polynucleotide is of a sufficient length to displace oligonucleotide a of the first polynucleotide or the second polynucleotide comprises a base modification that increases its binding stability. In some embodiments, the endonuclease is selected from the group consisting of UDG plus endonuclease VIII, RNase HI, RNase H2 and Endonuclease V. In some embodiments, the ligase is *E. coli* DNA ligase or T4 DNA ligase. In further embodiments, the base modification that increases its binding stability is a locked nucleic acid (LNA).

In some aspects, the disclosure provides a method of producing a processed substrate molecule, the method comprising (i) ligating a polynucleotide 1 to a 5' terminus of a substrate molecule that is at least partially double stranded; (ii) annealing a polynucleotide 2 to polynucleotide 1 under conditions that promote the annealing; (iii) excising at least one nucleotide from the 5' terminus of the polynucleotide 2; and then (iv) ligating polynucleotide 2 to the 3' terminus of the double stranded substrate molecule to produce the processed substrate molecule. In some embodiments, the method further comprises the step of contacting the substrate molecule with a polynucleotide kinase to add a phosphate group to the 5' end of the substrate molecule. In further embodiments, the method further comprises the step of making the substrate molecule blunt-ended by contacting the substrate molecule with a polymerase enzyme possessing 3'-5' exonuclease activity. In still further embodiments, the method further comprises the step of contacting the substrate molecule with a template-independent polymerase to adenylate the 3' end of the substrate molecule. In some embodiments, the substrate molecule is naturally occurring or the substrate molecule is synthetic. In related embodiments, the substrate molecule is naturally occurring. In some embodiments, the substrate molecule is genomic DNA, and in further embodiments the genomic DNA is eukaryotic or prokaryotic. In various embodiments, the genomic DNA is fragmented in vitro or in vivo, while in still further embodiments the in vitro fragmenting is performed by a process selected from the group consisting of shearing, cleaving with an endonuclease, sonication, heating, irradiation using an alpha, beta, or gamma source, chemical cleavage in the presence of metal ions, radical cleavage, and a combination thereof. In some embodiments, the in vivo fragmenting occurs by a process selected from the group consisting of apoptosis, radiation, and exposure to asbestos. In other embodiments, the substrate molecule is synthetic and is selected from the group consisting of cDNA, DNA produced by whole genome amplification, primer extension products comprising at least one double-stranded terminus, and a PCR amplicon. In some embodiments, polynucleotide 1 is at least partially double stranded and comprises oligonucleotide a and oligonucleotide b. In further embodiments, polynucleotide 2 anneals to oligonucleotide b. In additional embodiments, the annealing results in a nick, a gap, or an overlapping base between polynucleotide 2 and the 3' end of the substrate molecule. In some embodiments, oligonucleotide a comprises a base that is susceptible to degradation. In further embodiments, oligonucleotide a is contacted with an enzyme capable of degrading oligonucleotide a. In additional embodiments, the polynucleotide 2 anneals to polynucleotide 1.

In some embodiments, the method further comprises the step of contacting the substrate molecule with a polymerase, a deoxynucleotide triphosphate, and a ligase. In some embodiments, a polymerase has a 5' exonuclease activity and can support a nick-translation reaction. In further embodiments, the method further comprises the step of contacting the substrate molecule with a 5' flap endonuclease and a ligase. In some embodiments, oligonucleotide a lacks a 5' phosphate group. In further embodiments, polynucleotide 2 comprises a modified base. In still further embodiments, the annealing results in dehybridization of oligonucleotide a and oligonucleotide b. In some embodiments, polynucleotide 2 lacks a 5' phosphate.

Alternatively, DNA fragmentation or other processing can result in pre-existing DNA ends with 3'-overhangs sufficient for 5' adapter annealing.

Figure 8:
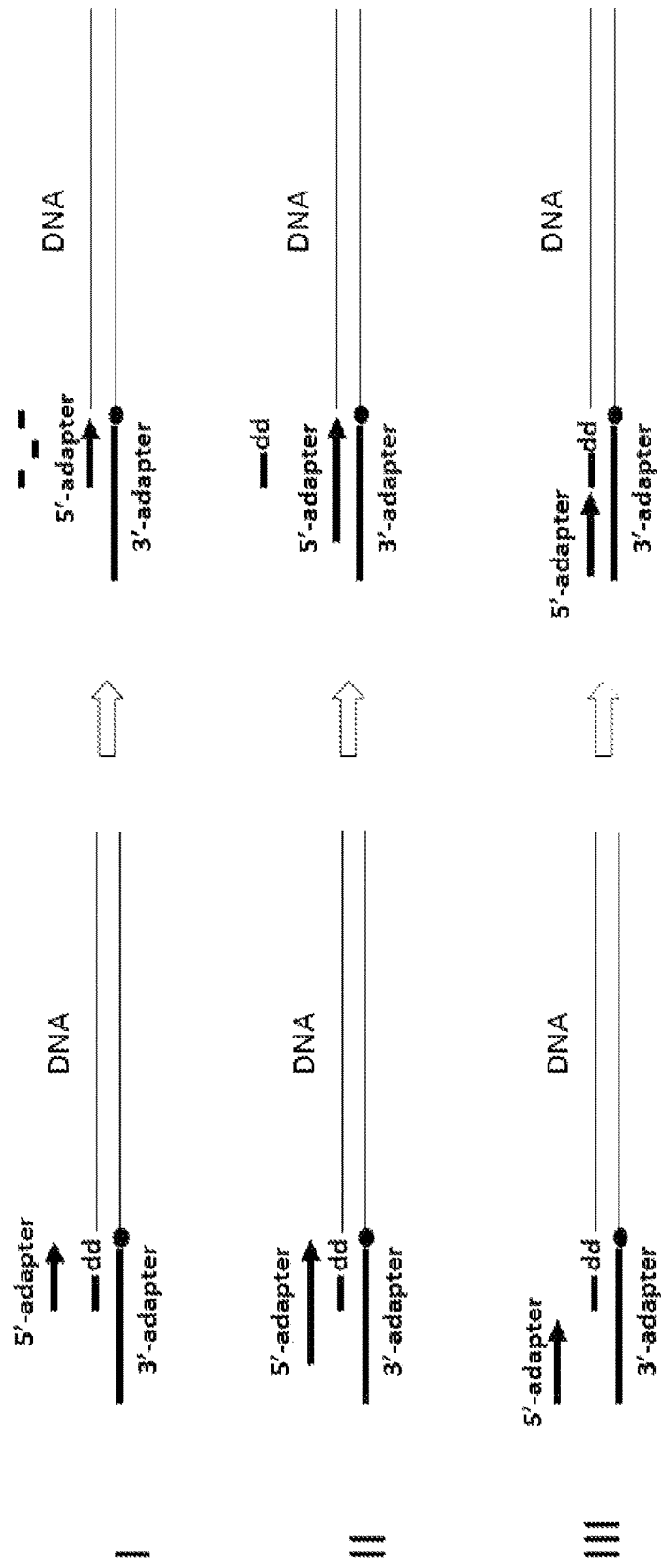
Figure 8:
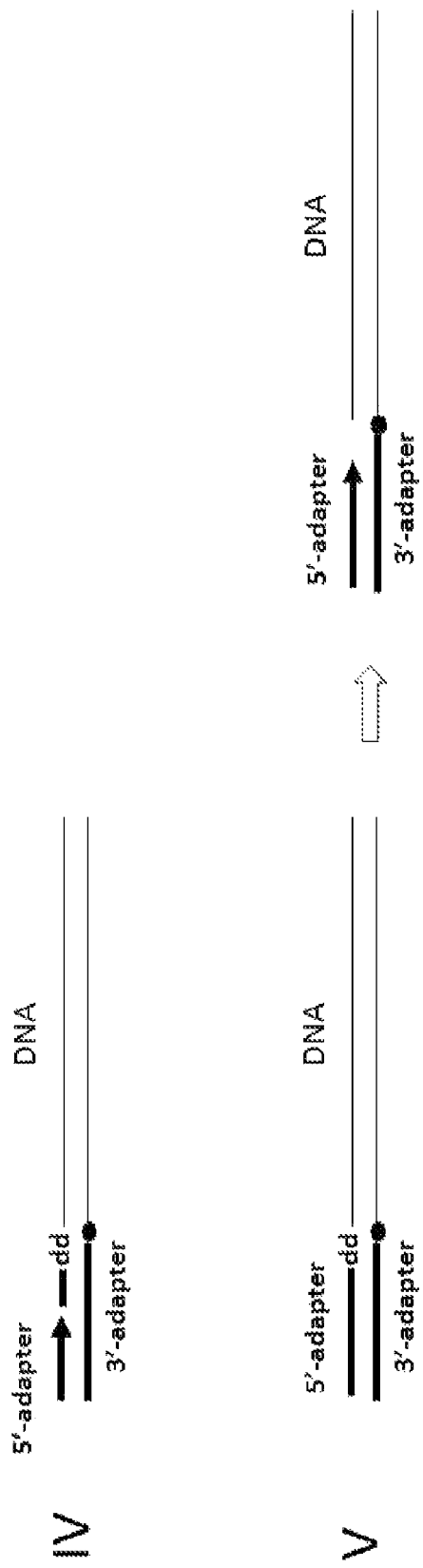
Figure 9A:
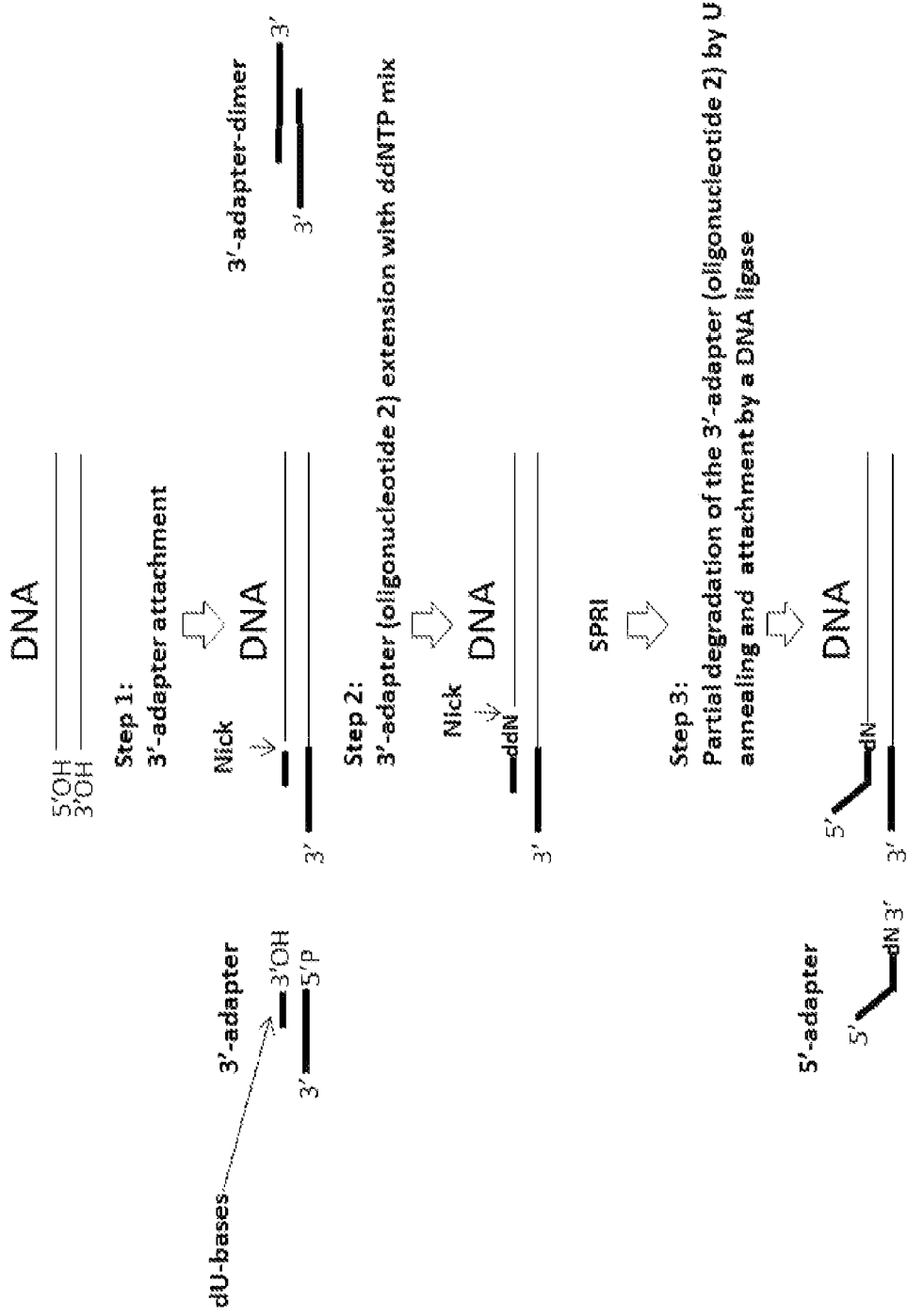
Figure 9B:
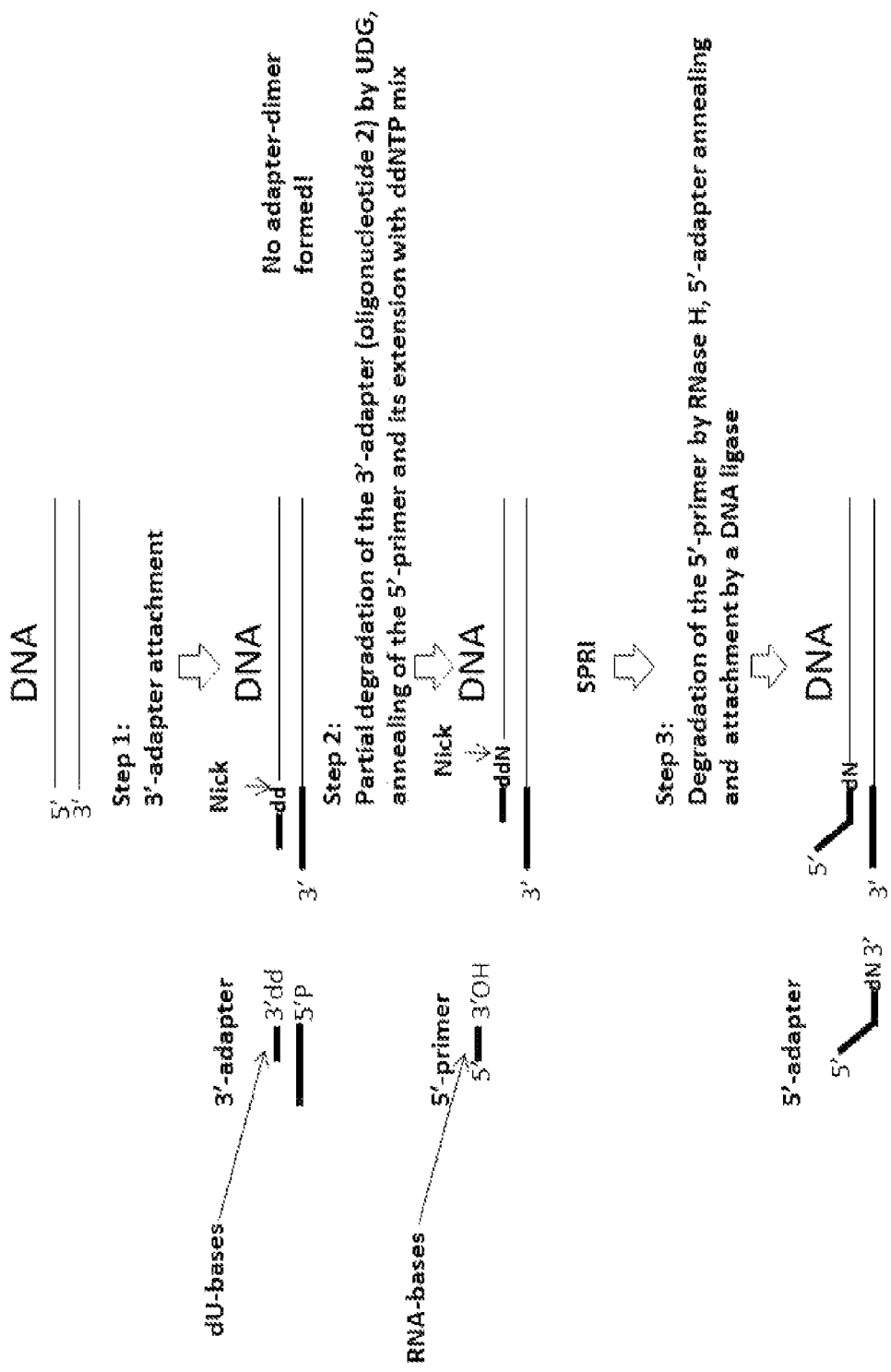
Figure 9C:
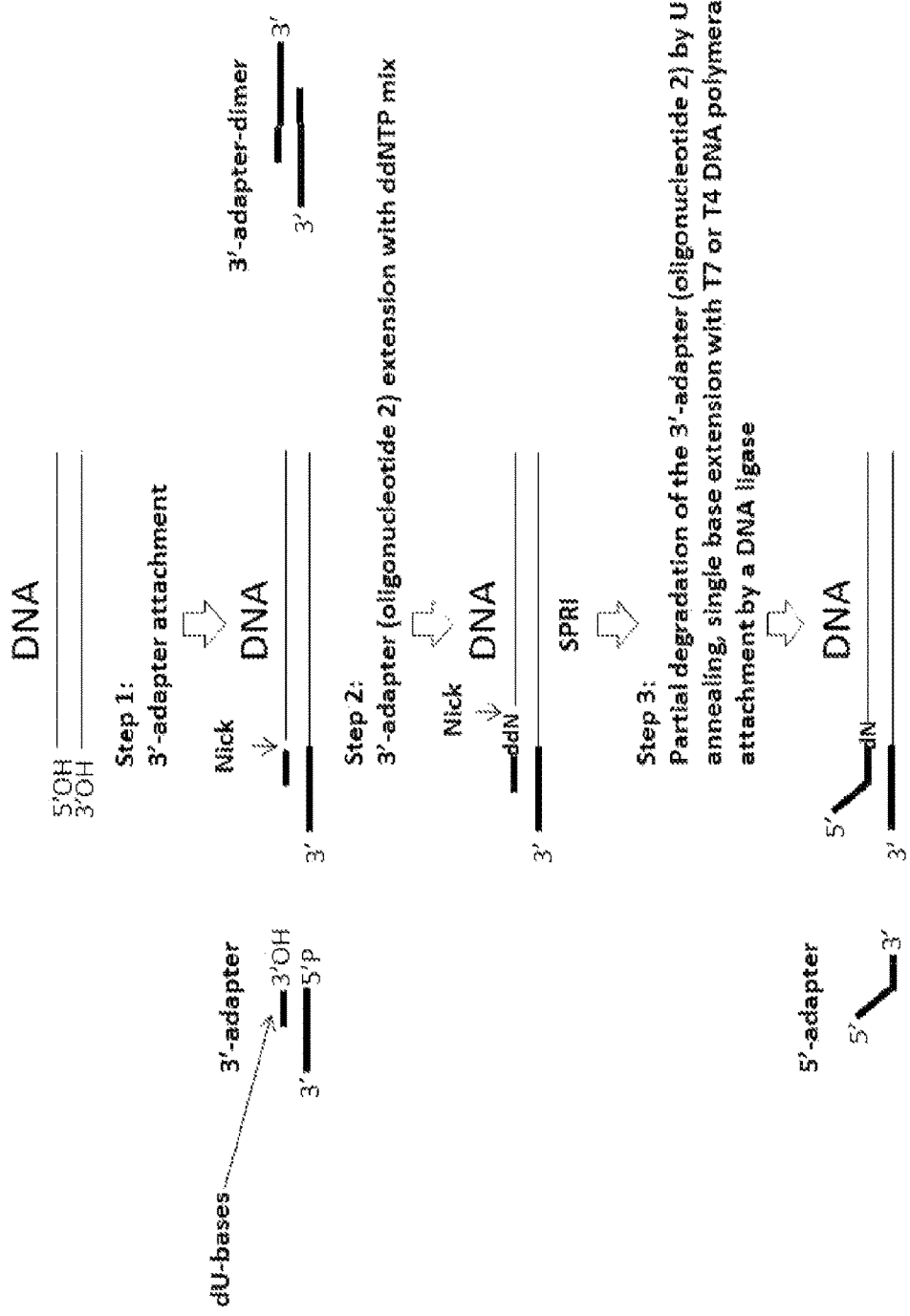
Figure 9D:
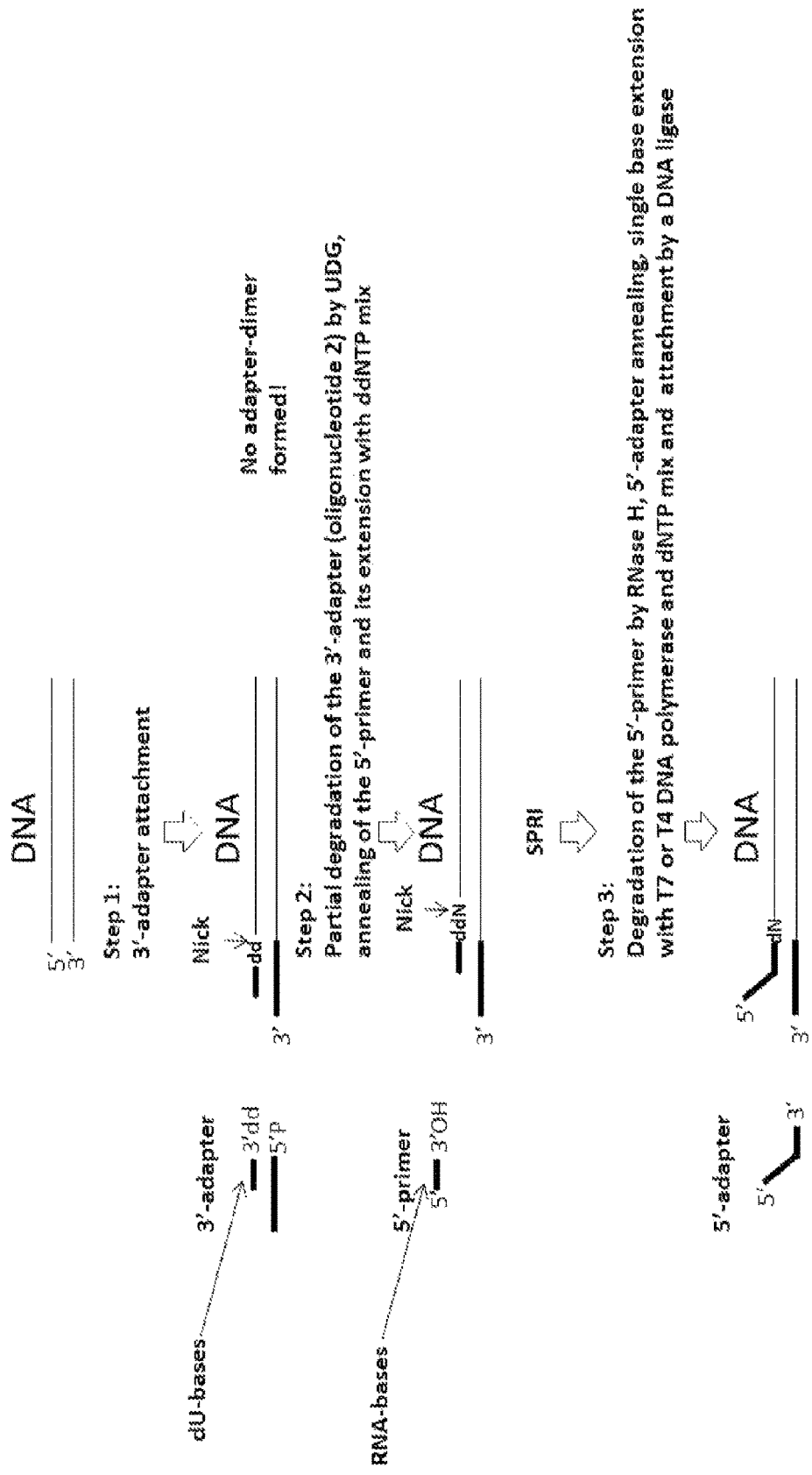

FIG. 8 Methods to anneal the 5' adapter by binding after degradation of the $2^{nd}$ oligonucleotide that was previously annealed to the 3'-adapter by competitive displacement of the $2^{nd}$ oligonucleotide that was previously annealed to the 3'-adapter by binding to the upstream region of the 3'-adapter (followed by limited nick-translation and degradation of the $2^{nd}$ oligonucleotide that was previously annealed to the 3'-adapter)

by having the 5'-adapter pre-annealed to the upstream region of the 3'-adapter (followed by limited nick-translation and degradation of the $2^{nd}$ oligonucleotide that was previously annealed to the 3'-adapter)

by having 3' blocked 5'-adapter instead of the $2^{nd}$ oligonucleotide that is activated by cleavage FIG. 9 A-D. 5' adapter ligation using single base extension FIG. 10 Synthesis of Illumina NGS library I Library I synthesis occurs in either 5 or 6 steps:

FIG. 10a:

1—substrate molecule dephosphorylation and polishing

2—ligation of the 3' adapter with Illumina sequence P7 (10a) or P5' (10b)

3—partial degradation of the 3' adapter and annealing of the complementary 5' adapter with Illumina sequence P5 (10a) or P7' (10b)

4—polymerase extension of the 5' adapter by nick-translation, and

Figure 10A:
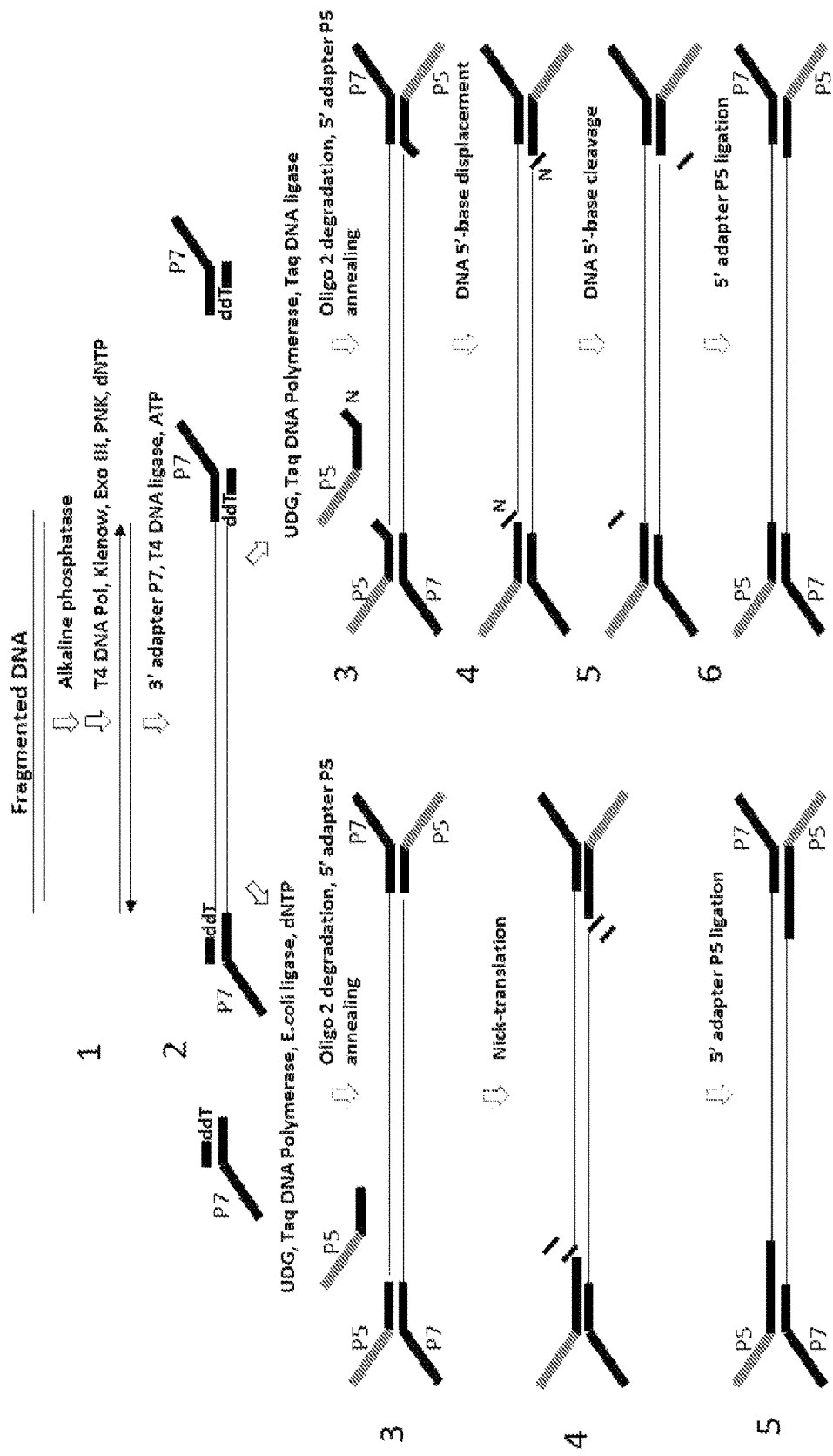
Figure 10B:
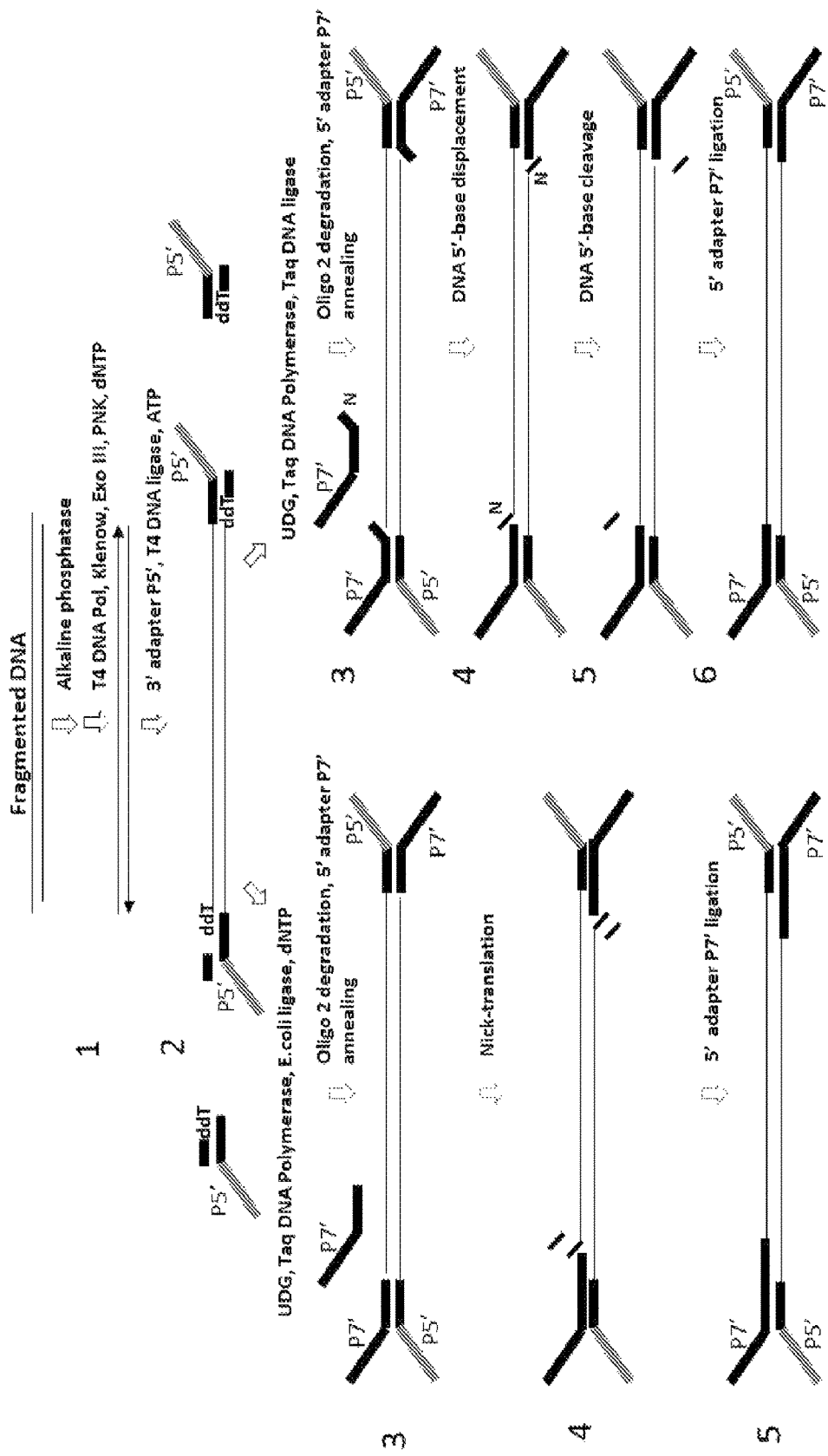

5—ligation of the 3' end of the 5' adapter to the exposed 5' phosphate of the DNA substrate or, alternatively, in FIG. 10b:

4—displacement of the 5' base(s) of the DNA substrate and annealing of the 3' base(s) of the 5' adapter 5—cleavage of the displaced 5' base(s) of the DNA substrate by a 5'-flap endonuclease, and 6—ligation of the 3' end of the 5' adapter to the exposed 5' phosphate of the DNA substrate The library can be amplified by PCR using primers P5 and P7'

Figure 11:
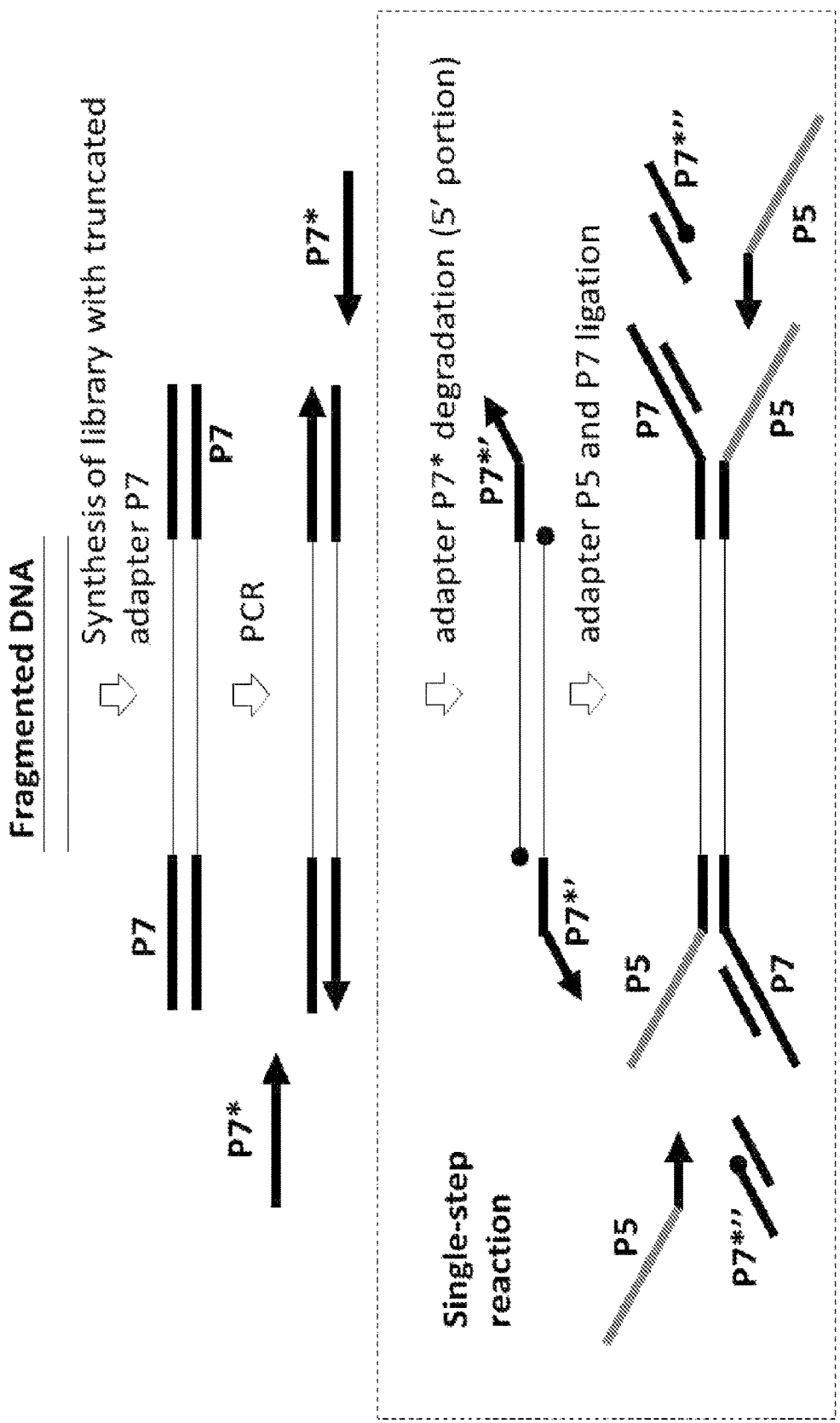

FIG. 11 Synthesis of an Illumina NGS library II

Library II synthesis occurs in 4 steps:

1—Synthesis of NGS library with truncated adapter P7 by one of two methods described in FIG. 6

2—Library amplification with truncated or full length degradable primer P7*

3—Degradation of the incorporated P7* primer followed by annealing and ligation of the 5' adapter P5

4—If a truncated degradable primer P7* was used in step two, a bridge-ligation of the P7*'" adapter to the truncated adapter P7*' is performed to complete full-length adapter P7

FIGS. 12 A and B. Synthesis of an Ion Torrent library

Library synthesis is performed by:

1—DNA substrate dephosphorylation and polishing

2—ligation of the 3' adapter with sequence A1'-P1' (a) or A' (b)

3—nick-translation ligation or base cleavage ligation of the 3' end of the 5' adapter with sequence A (a) or sequence P1-$A_1$ (b) to the 5' end of trimmed DNA 4—library amplification by PCR using primers A and P1

Figure 13A:
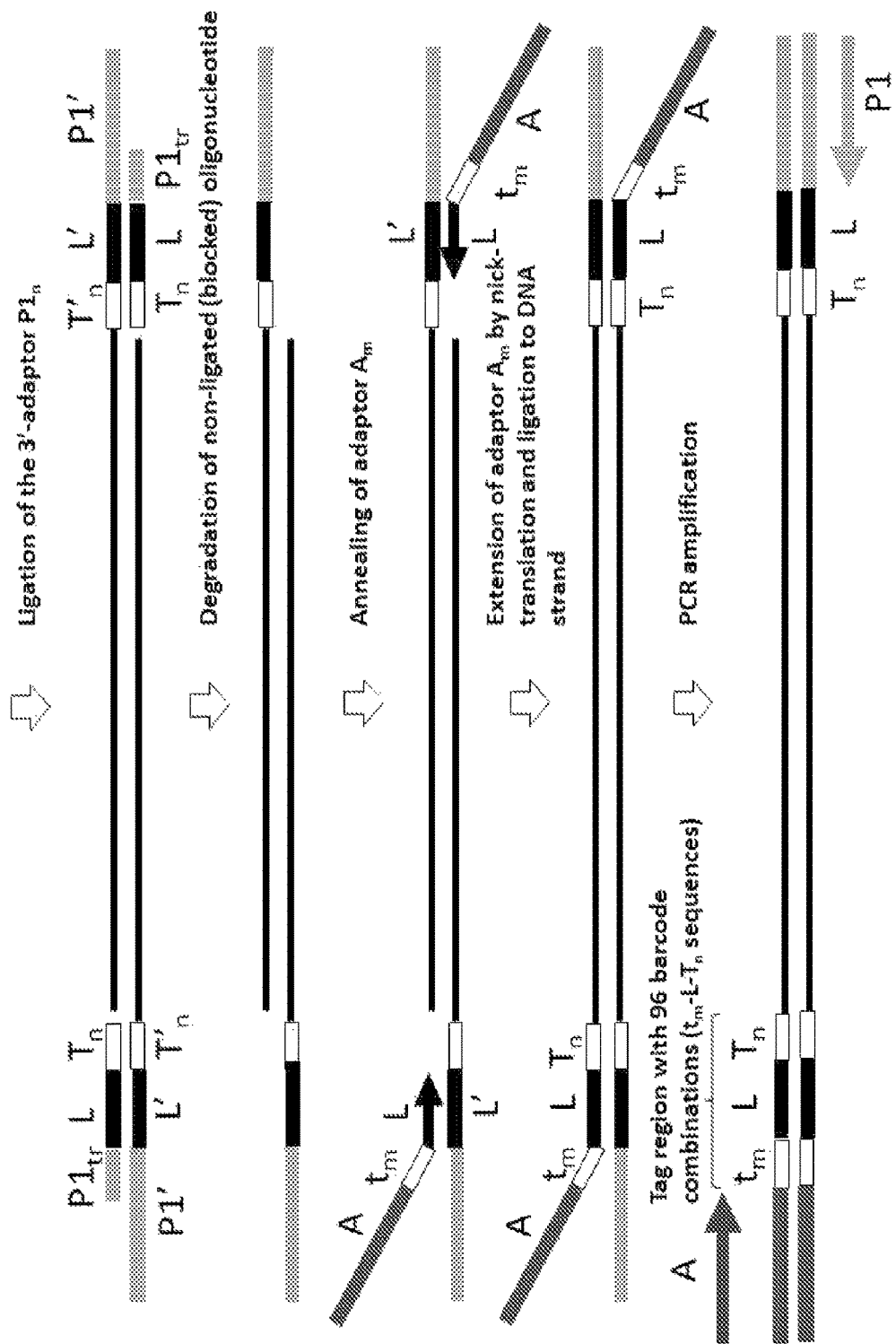
Figure 13B:
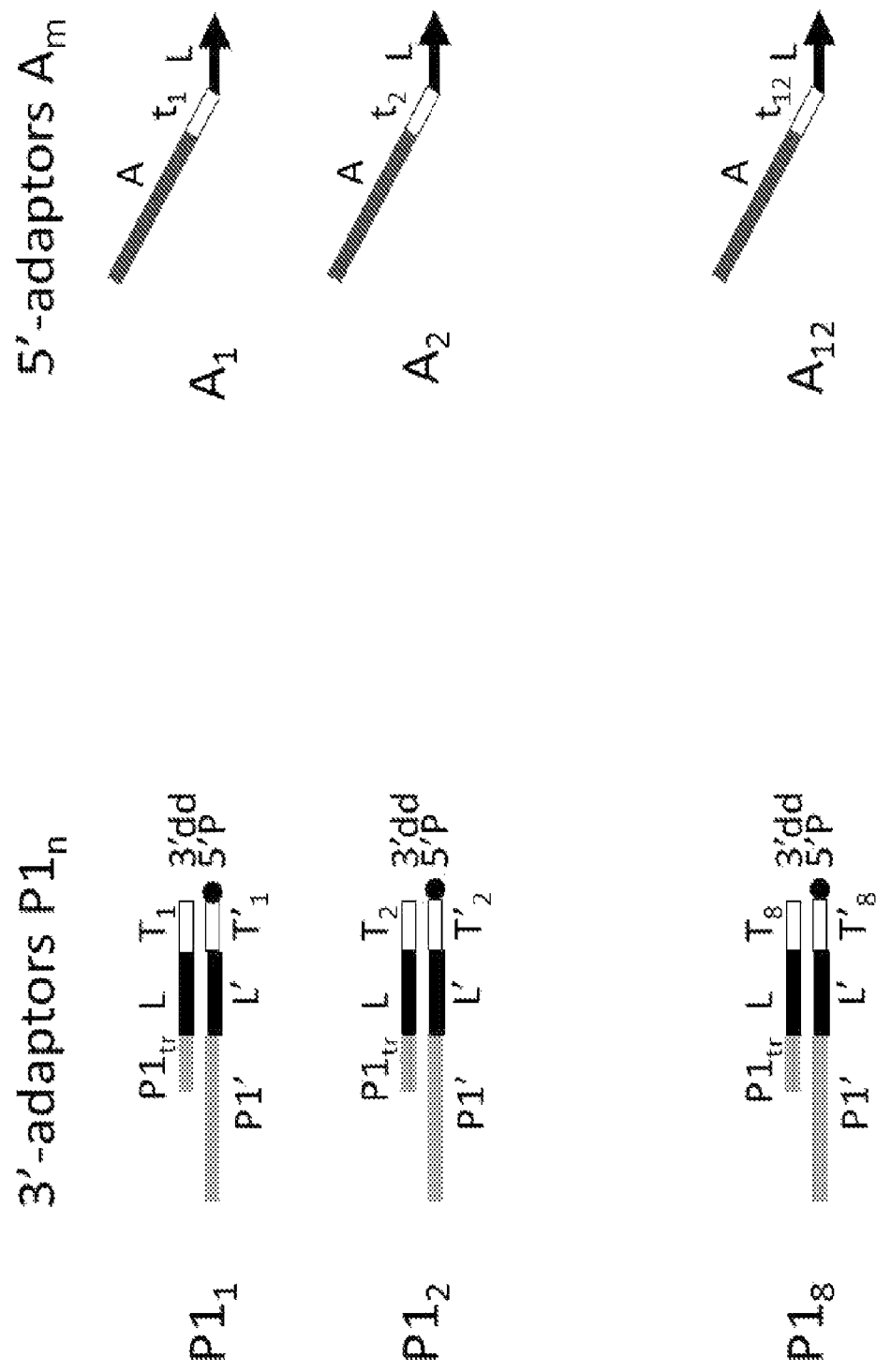

FIG. 13 Synthesis of an Ion Torrent library with 96 combinatorial barcode sequences using only 20 adapter sequences Library synthesis steps:

1—DNA end dephosphorylation and polishing (not shown)

2—ligation of the (blunt) 3'-adapter $P1_n$ with sequence $T'_n$-L'-P1' and 5' phosphate group and 3'-blocked complementary oligonucleotide with sequence $P1_{n'}$-L-$T_n$ 3—degradation of the 3'-blocked complementary oligonucleotide $P1_{n'}$-L-T 4—annealing of the 5'-adapter $A_m$ with sequence A-$t_m$-L to the linker region L'

5—extension of the 5'-adapter $A_m$ by nick-translation polymerization and ligation of the 3' end of the extended 5'-adapter $A_m$ to the 5' end of DNA 6—library amplification by PCR using primers A and P1

Adapters with combinatorial barcodes include 8 adapters $P1_n$ containing barcode sequences $T_1, T_2, \ldots, T_8$ and 12 adapters $A_m$ containing barcode sequences $t_1, t_2, \ldots, t_{12}$ Created library has a combinatorial barcode sequence $t_m$-L-$T_n$ with up to 96 barcode combinations.

Figure 14:
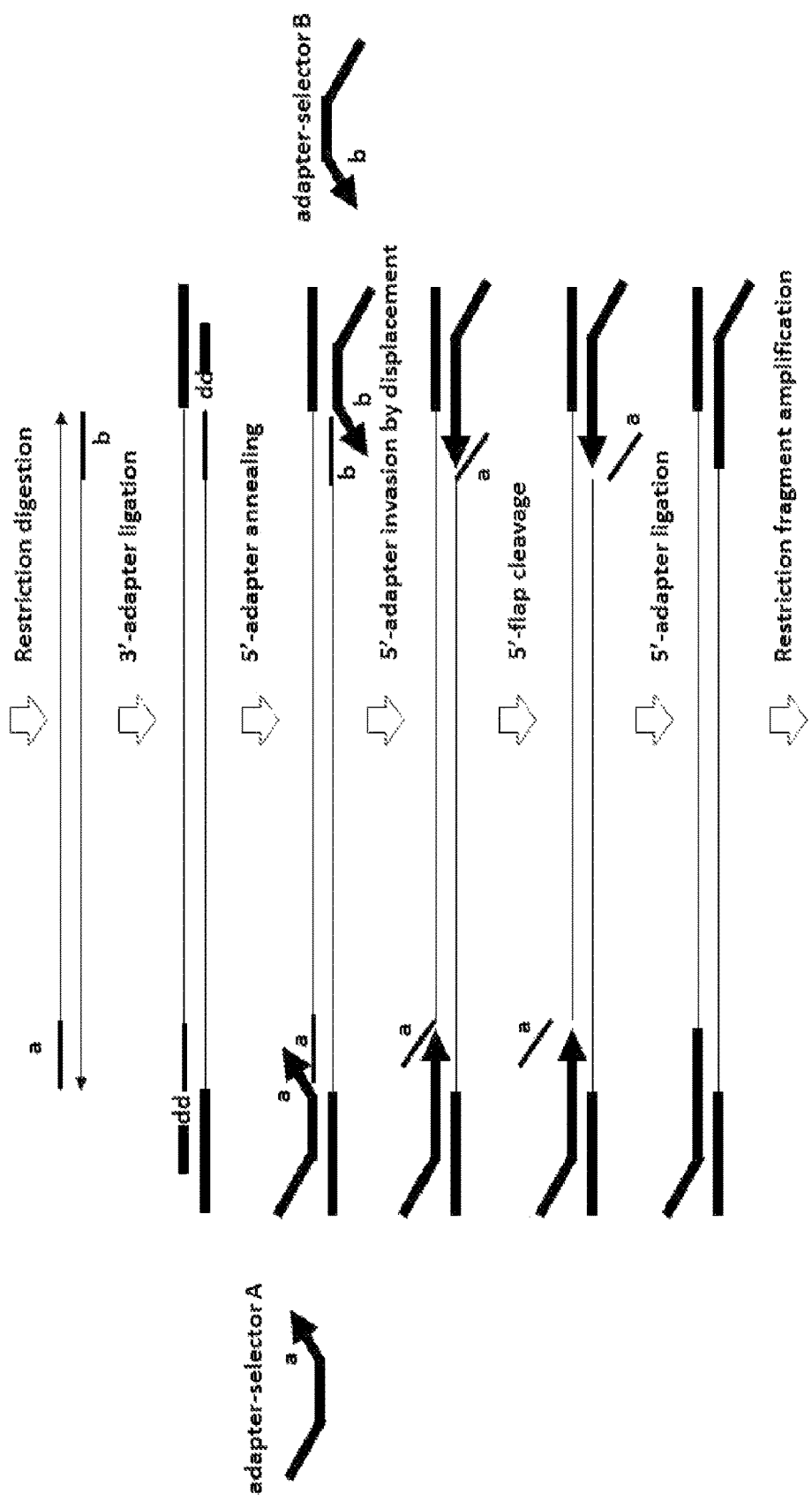

FIG. 14 Enrichment of selected restriction fragments by 5' adapter ligation

A restriction DNA fragment is selected by 5'-adapter ligation followed by PCR amplification. Selection occurs by two 5'-adapter-selectors A and B containing sequences a and b that are identical to the 5' terminal sequences of the restriction fragment. The method of enrichment involves:

DNA digestion with restriction endonuclease;

ligation of the 3'-adapter;

partial degradation of the 3'-adapter and annealing of the 5'-adapter-selectors;

invasion of the 5'-adapter-selectors into terminal sequences a and b of the restriction fragment;

cleavage of the displaced terminal sequences a and b by a 5'-flap endonuclease;

ligation of the 5'-adapter-selectors to the ends of the restriction fragment;

amplification of the selected restriction fragment by PCR.

Steps 1, 2 and also steps 3-6 can be combined into a single incubation reaction.

FIG. 15 Target enrichment by primer extension

Enrichment is performed by 5' adapter attachment where the 3' overhang is created by extension of a primer complementary to a target DNA region on a library with adapters A and B and partial digestion of the 5' domain of adapter A. Biotinylated 5'-adapter is annealed to the 3'-overhang of adapter A and then ligated to the 5' end of adapter A either after trimming by limited nick-translation (a) or invasion-cleavage reaction (b). Library fragments containing target DNA region are then isolated by affinity capture using streptavidin magnetic beads, amplified by PCR and analyzed by sequencing.

Figure 16:
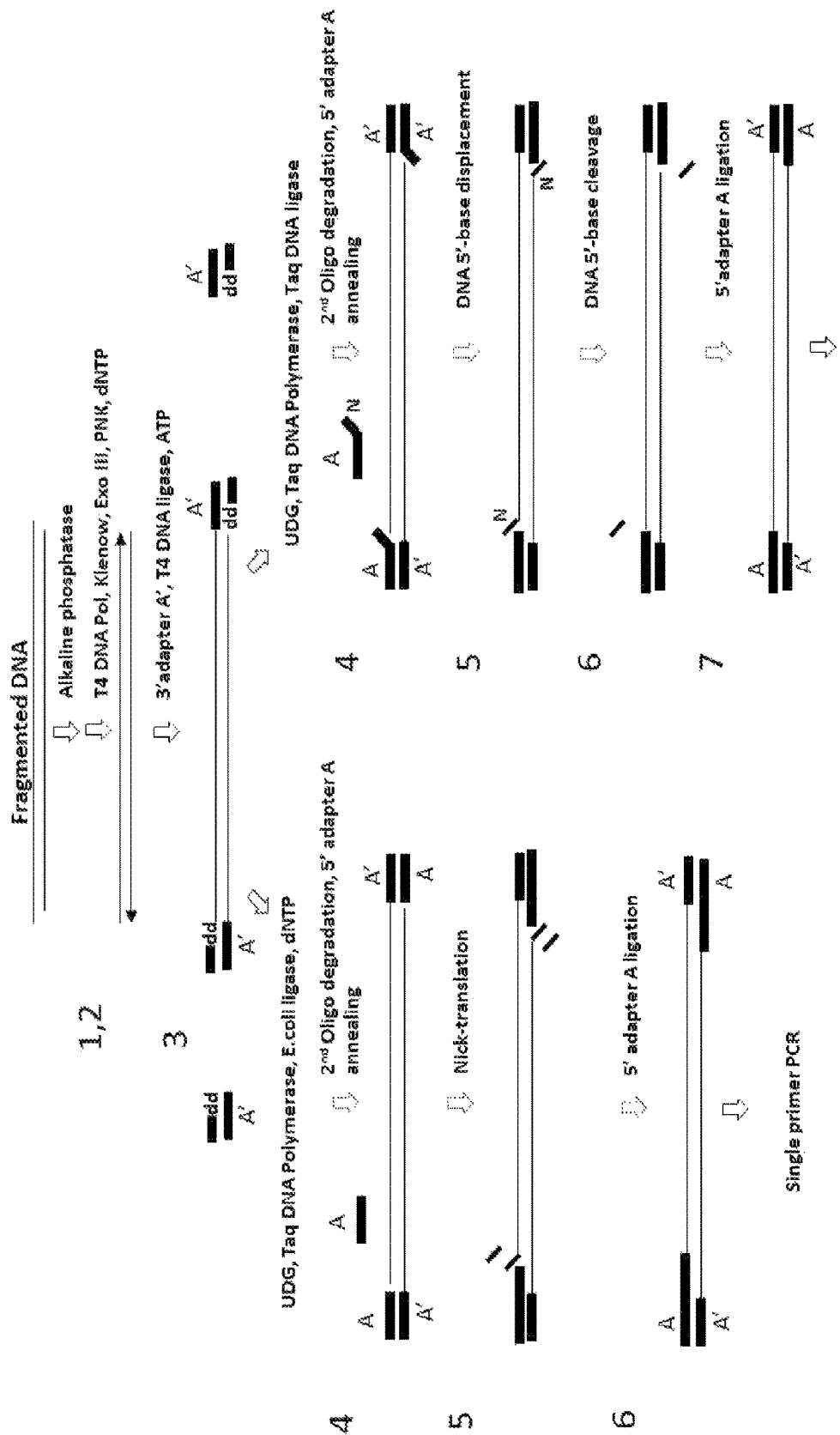

FIG. 16 Alternative library construction I

Library construction can be performed using a single adapter in either 6 or 7 steps:

1—substrate molecule dephosphorylation

2—substrate molecule end polishing/blunt end generation

3—ligation of the 3' adapter with sequence A'

Figure 17:
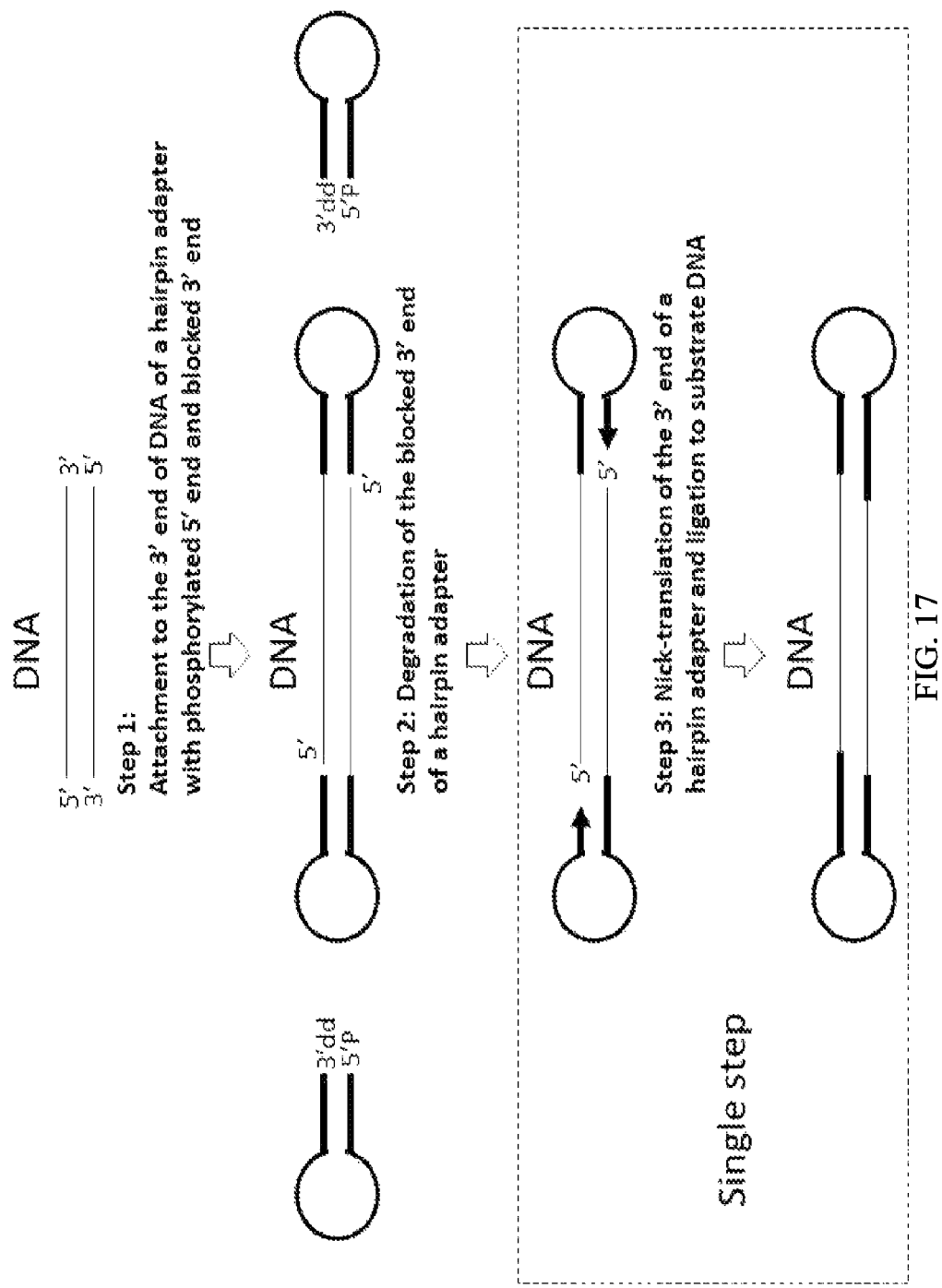

4—partial degradation of the 3' adapter and annealing of the complementary 5' adapter with sequence A 5—polymerase extension of the 5' adapter by nick-translation, and 6—ligation of the 3' end of the 5' adapter to the exposed 5' phosphate of the DNA substrate or, alternatively, by 5—displacement of the 5' base(s) of DNA and annealing of the 3' base(s) of the 5' adapter 6—cleavage of the displaced 5' base(s) of DNA by a 5'-flap endonuclease, and 7—ligation of the 3' end of the 5' adapter to the exposed 5' phosphate of the DNA substrate The library can be amplified by PCR using single primer A FIG. 17 Alternative library construction II Adapter attachment can create a library of double-stranded DNA fragments with covalently linked 3' and 5' DNA ends. Library construction is performed by:

1—substrate molecule dephosphorylation (not shown)

2—substrate molecule end polishing/blunt end generation (not shown)

Figure 18:
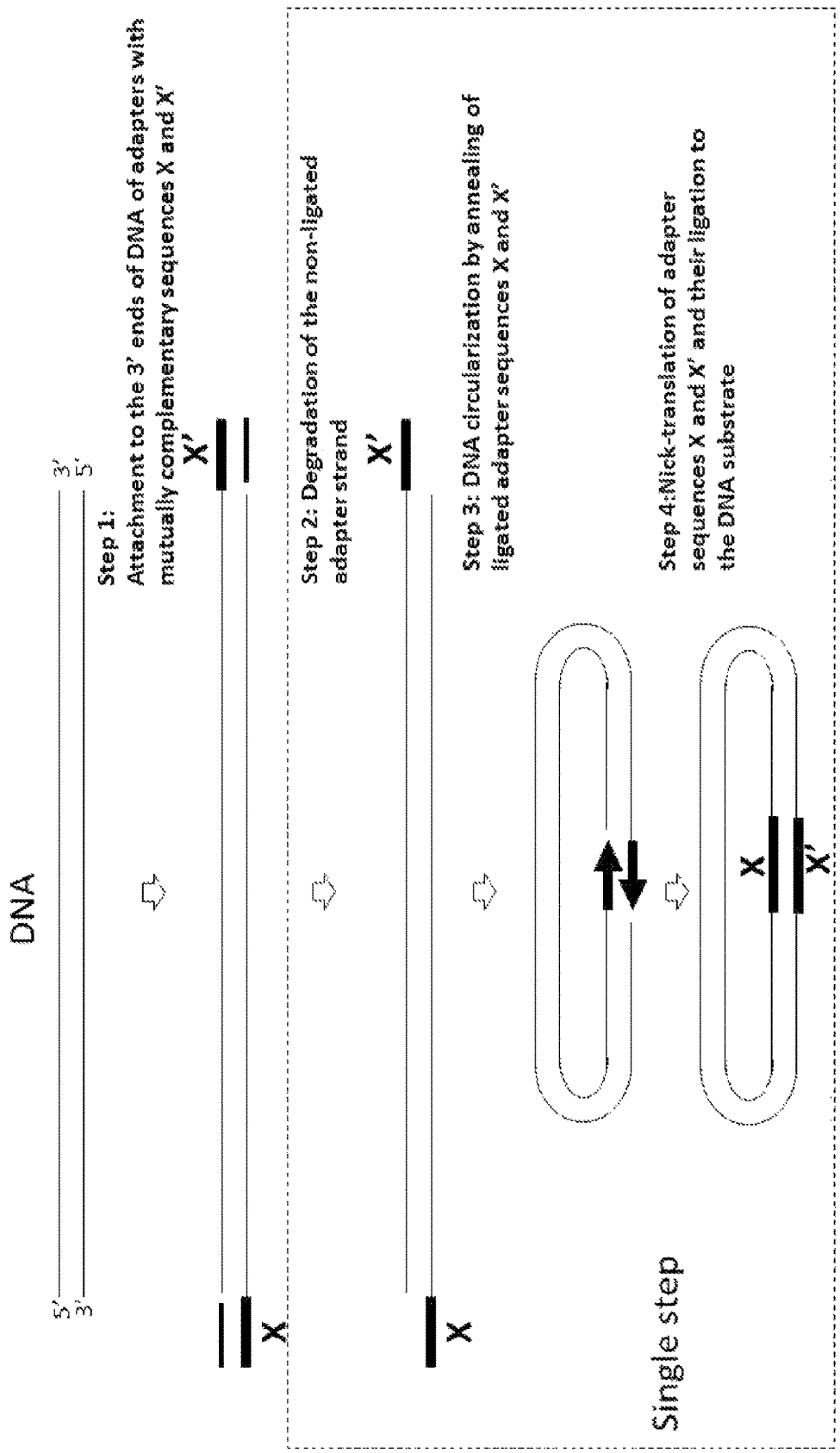

3—ligation of the hairpin blunt adapter with phosphorylated 5' end and blocked (optionally) 3' end 4—partial degradation of the hairpin adapter to create an extendable 3' end 5—nick-translation of the 3' end of the hairpin adapter and its ligation to the exposed 5' phosphate of the DNA substrate FIG. 18 Alternative library construction III A circularize NGS library can be constructed using following steps:

1—substrate molecule dephosphorylation (not shown)

2—substrate molecule end polishing/blunt end generation (not shown)

3—ligation of adapters with a phosphorylated 5' end and blocked (optionally) 3' end and mutually complementary sequences X and X'

4—degradation of the non-ligated adapter strands to create single-stranded 3' overhangs 5—non-covalent circularization of DNA by annealing of terminal sequences X and X' (performed at low DNA concentration)

6—covalent circularization of DNA by nick-translation ligation reaction

Figure 19:
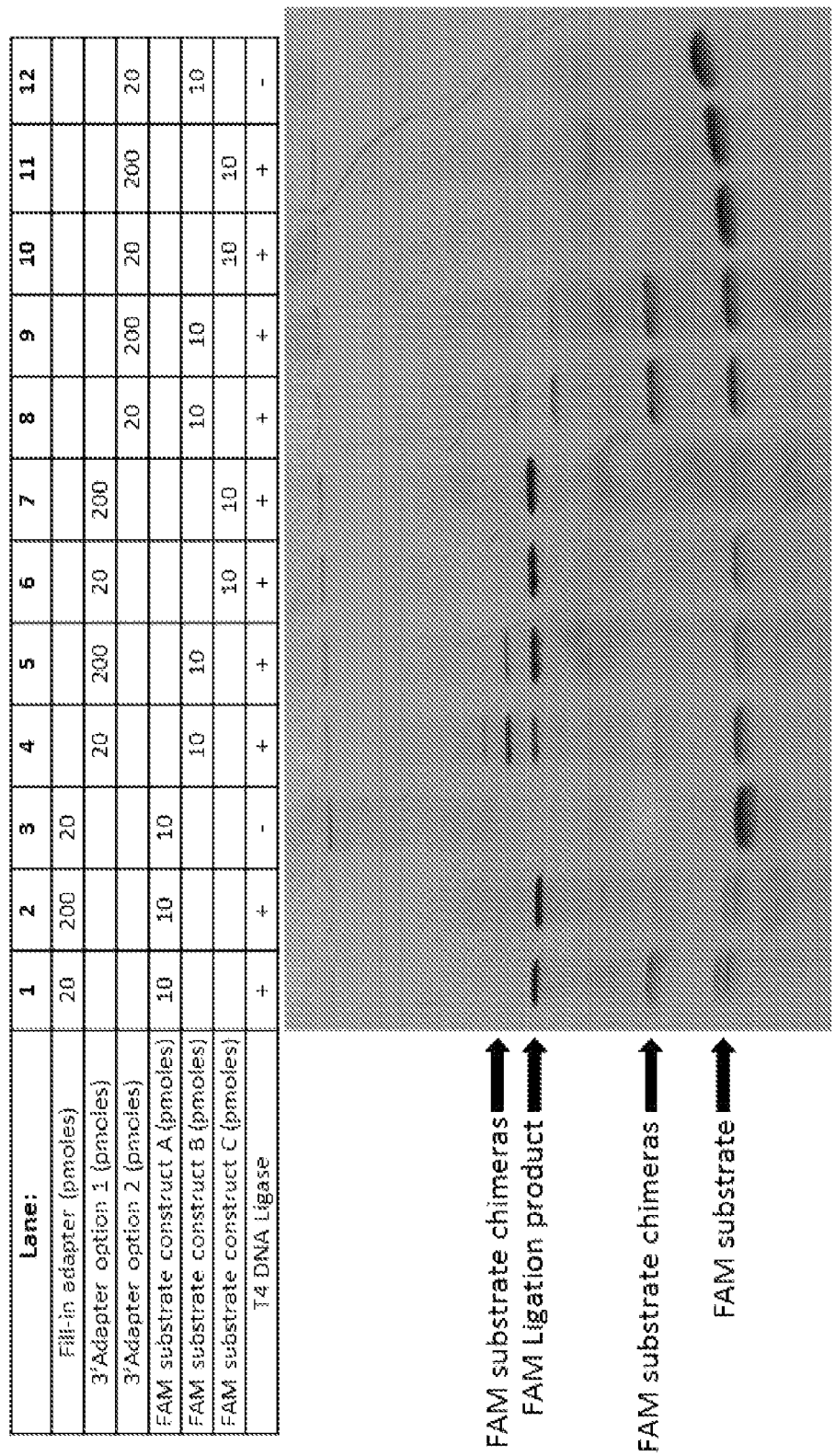

FIG. 19 Comparison of conventional adapter ligation to 3' adapter ligation using FAM-labeled oligonucleotide substrates (Example 1)

Figure 20:
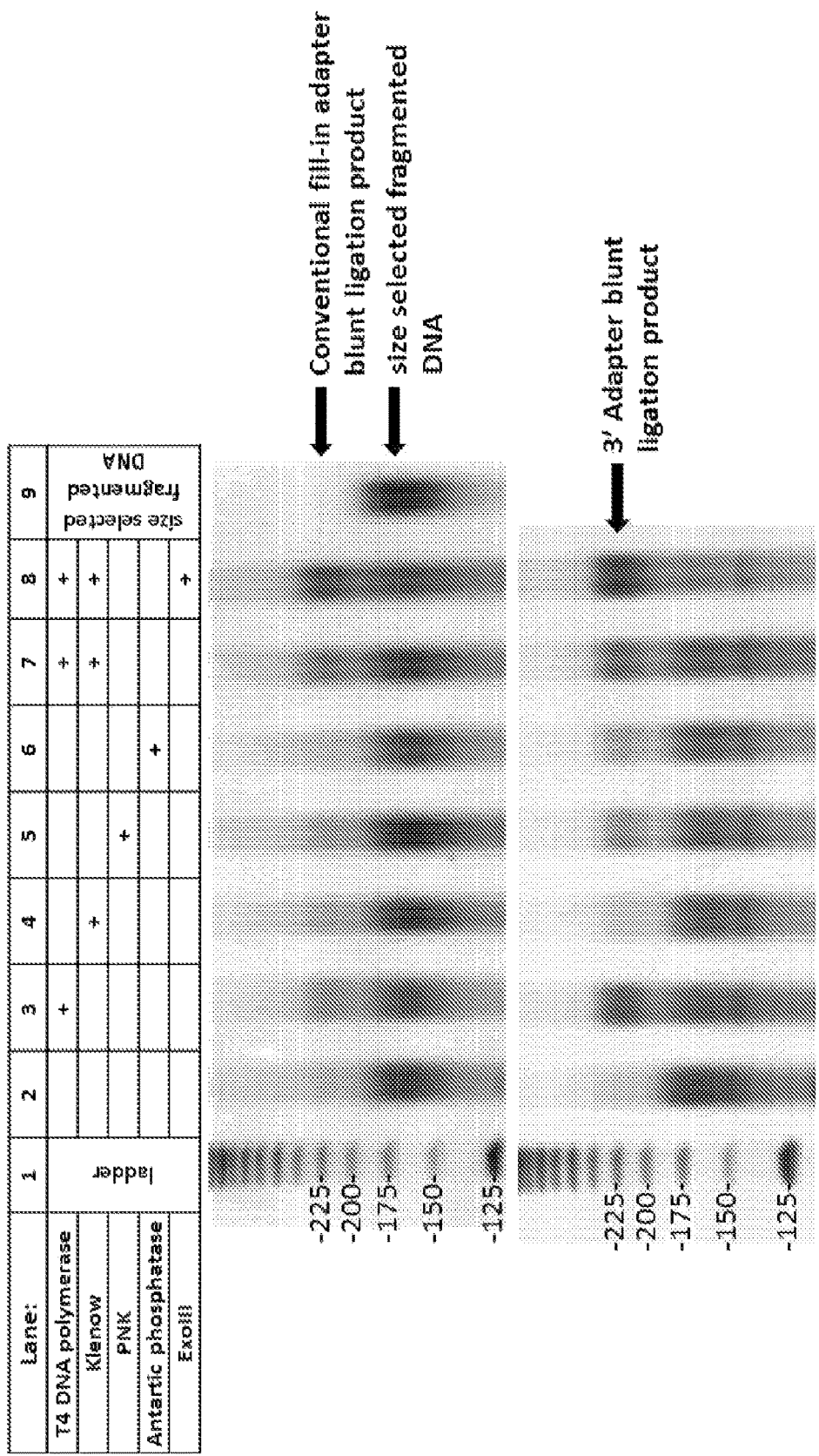

FIG. 20 Comparison of conventional adapter ligation to 3' adapter ligation using sheared, size-selected genomic DNA substrate (Example 2)

Figure 21A:
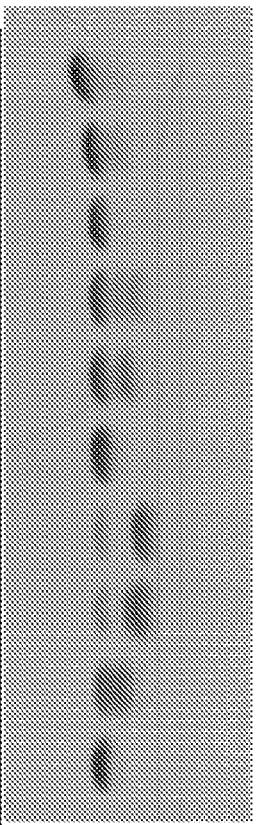
Figure 21B:
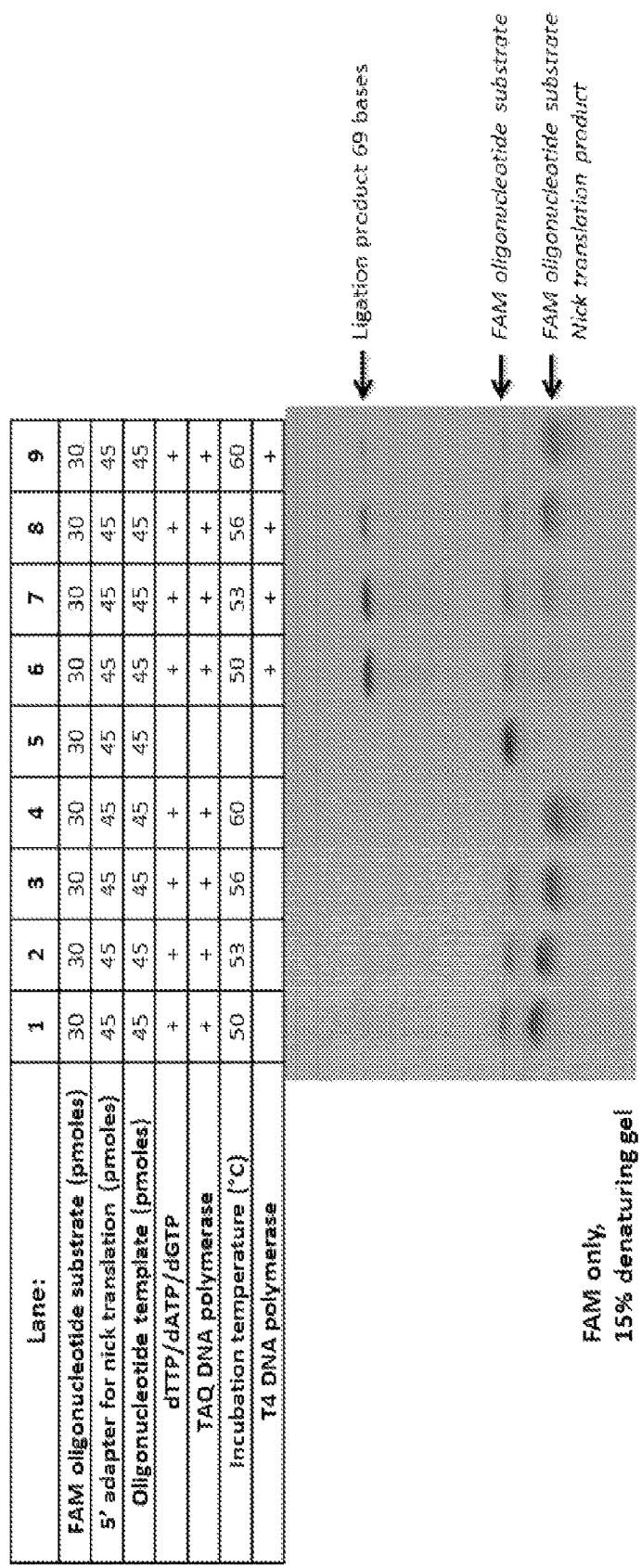

FIGS. 21 A and B. Temperature optimization for 5' adapter ligation using a FAM-labeled oligonucleotide substrate (Example 3)

Figure 22:
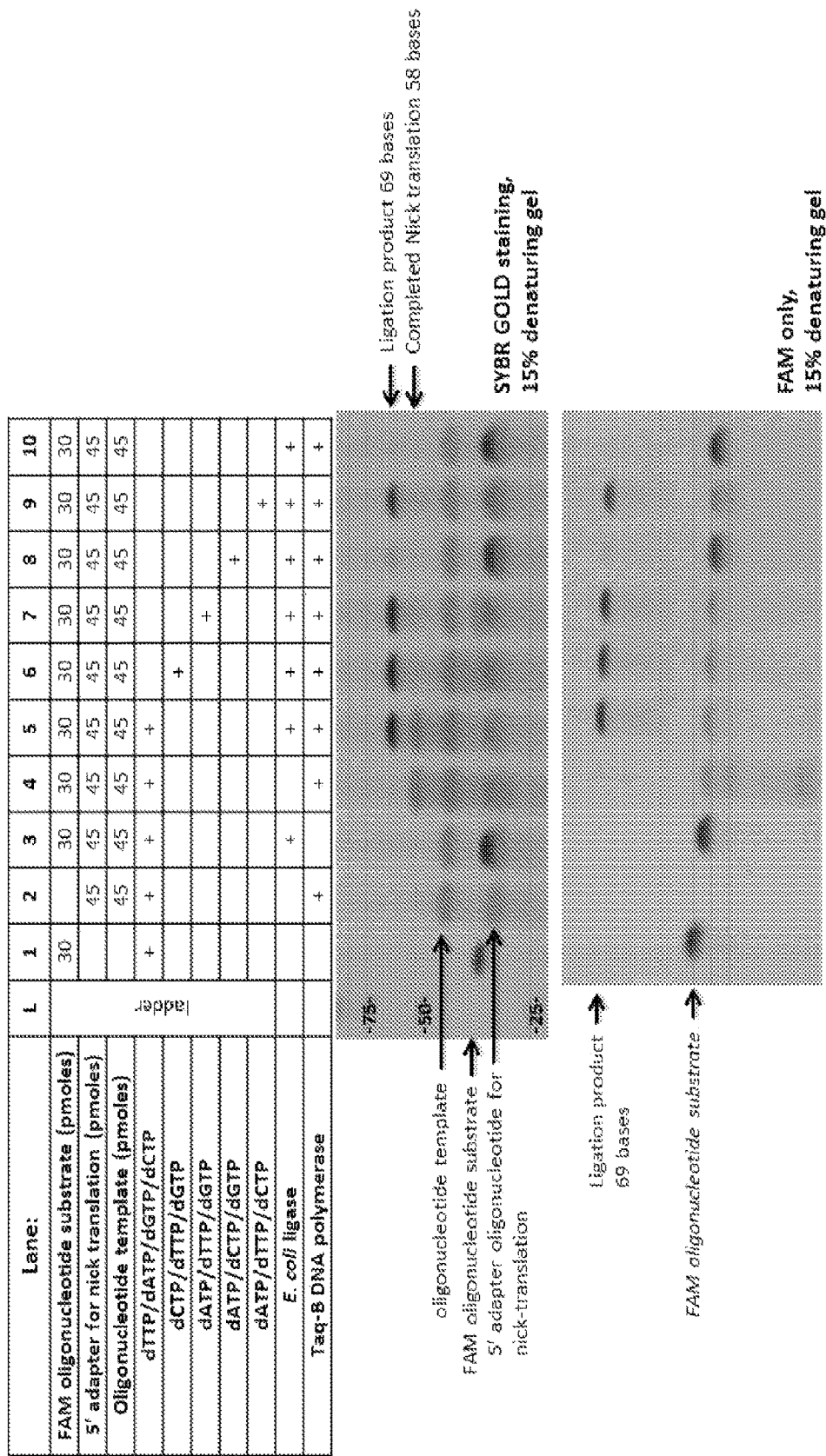

FIG. 22 Analysis of dNTP composition effects on 5' adapter ligation (Example 4)

Figure 23A:
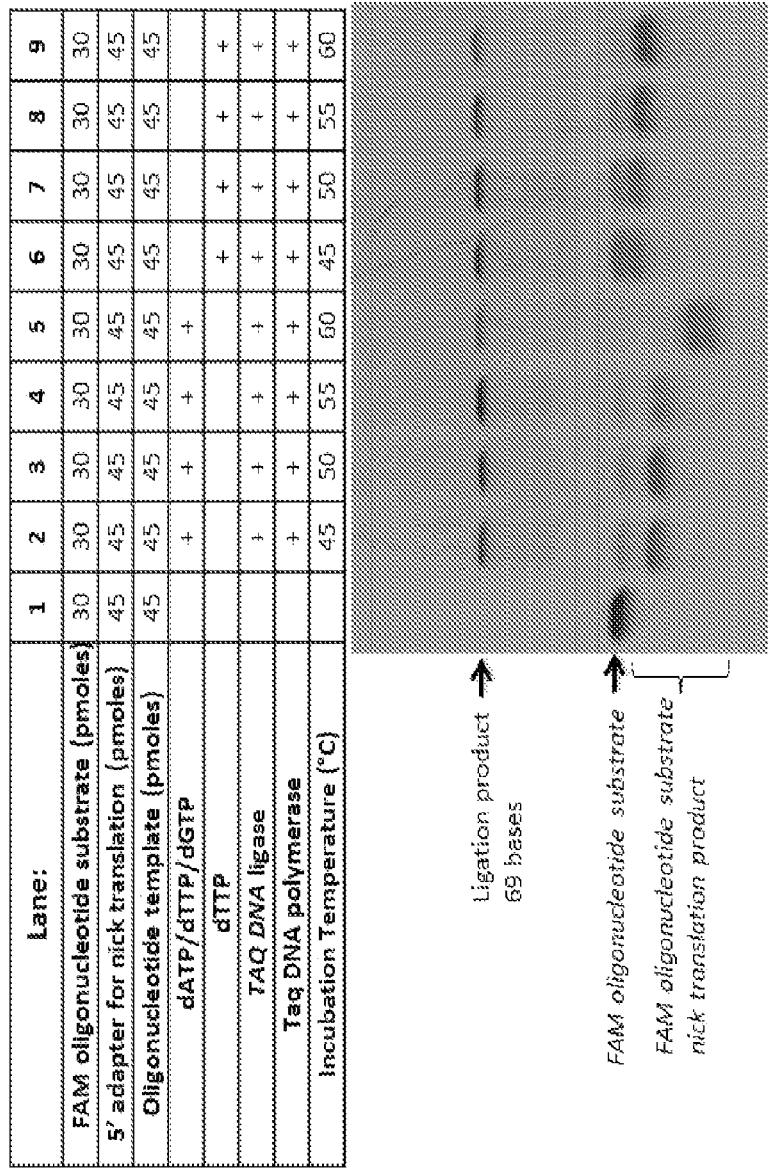
Figure 23B:
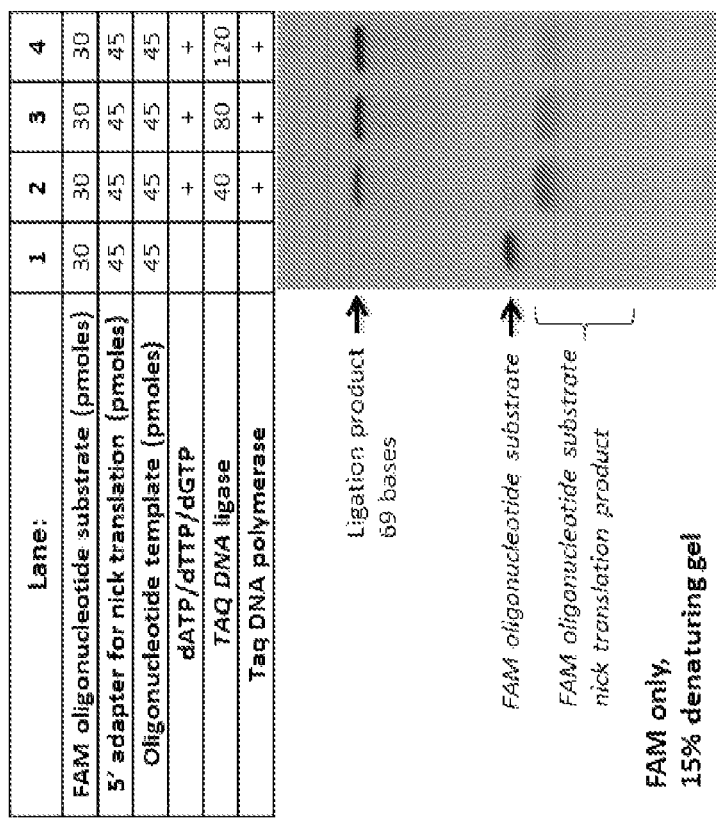

FIGS. 23 A and B. Coupled nick translation-ligation reaction with thermo stable enzymes (Example 5)

Figure 24:
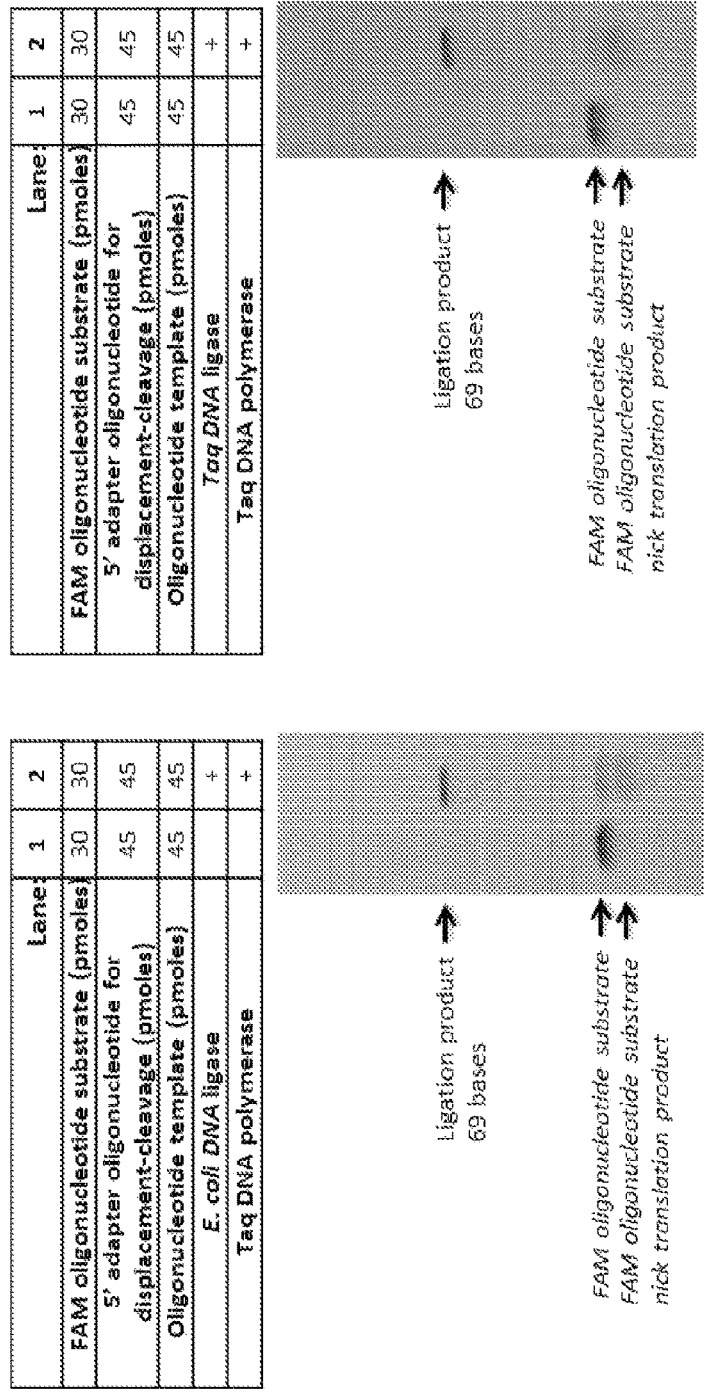

FIG. 24 Coupled displacement-cleavage-ligation reaction (Example 6)

Figure 25:
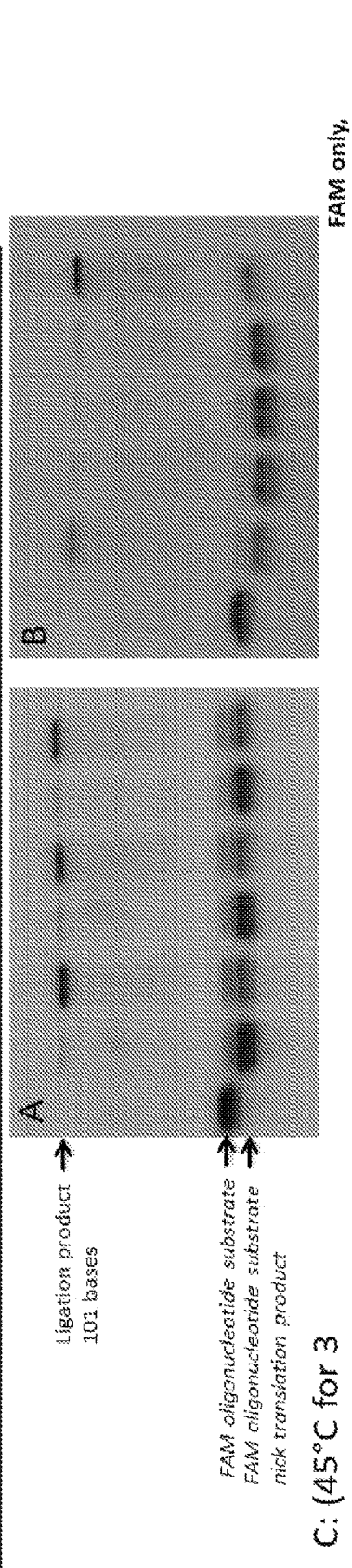

FIG. 25 Coupled displacement-cleavage-ligation reaction with either "N" universal/degenerate or "T" substrate-specific 5' adapter 3' overhang (Example 7)

Figure 26:
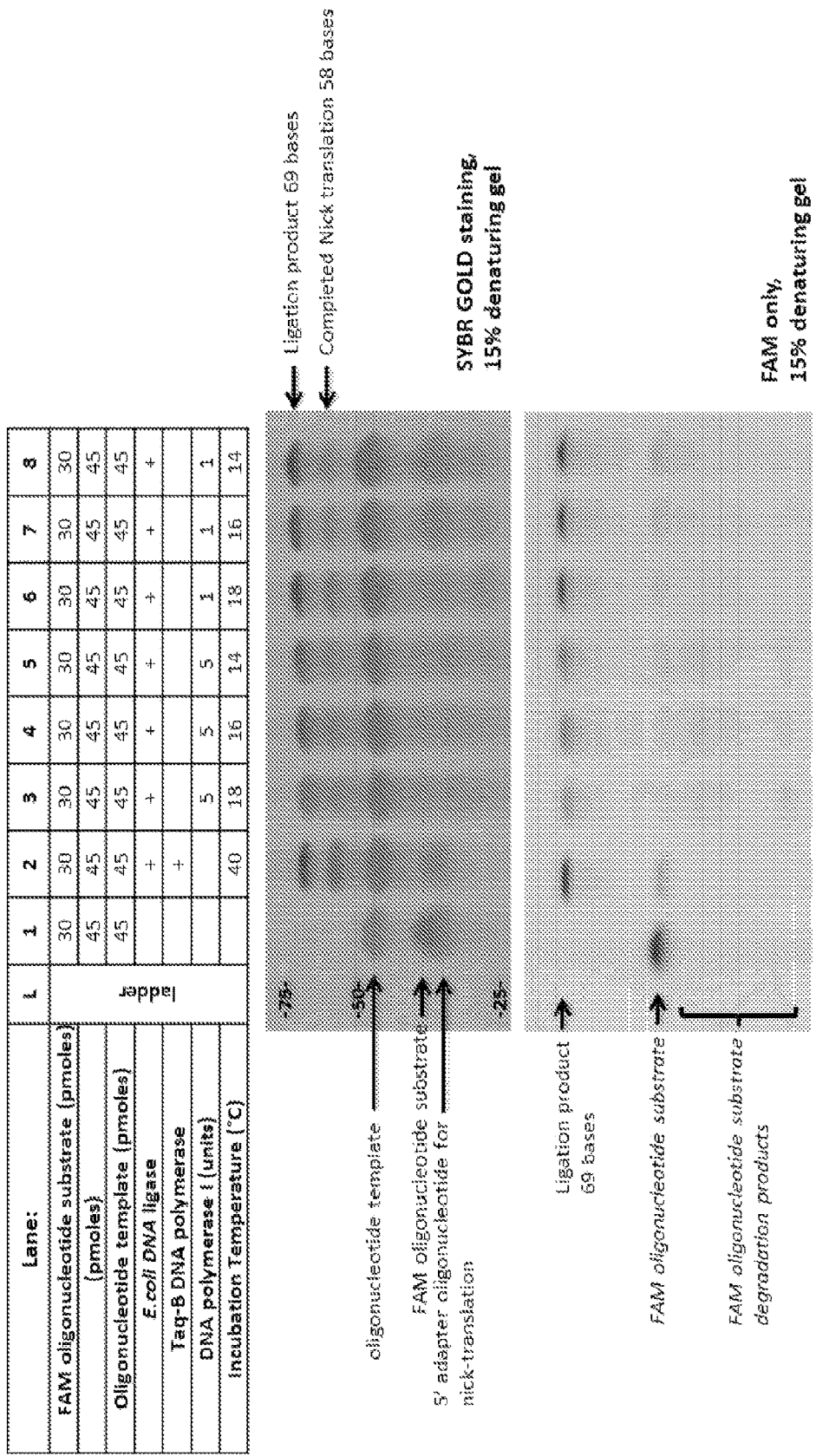

FIG. 26 Coupled nick-translation-ligation reaction using DNA polymerase I (Example 8)

Figure 27:
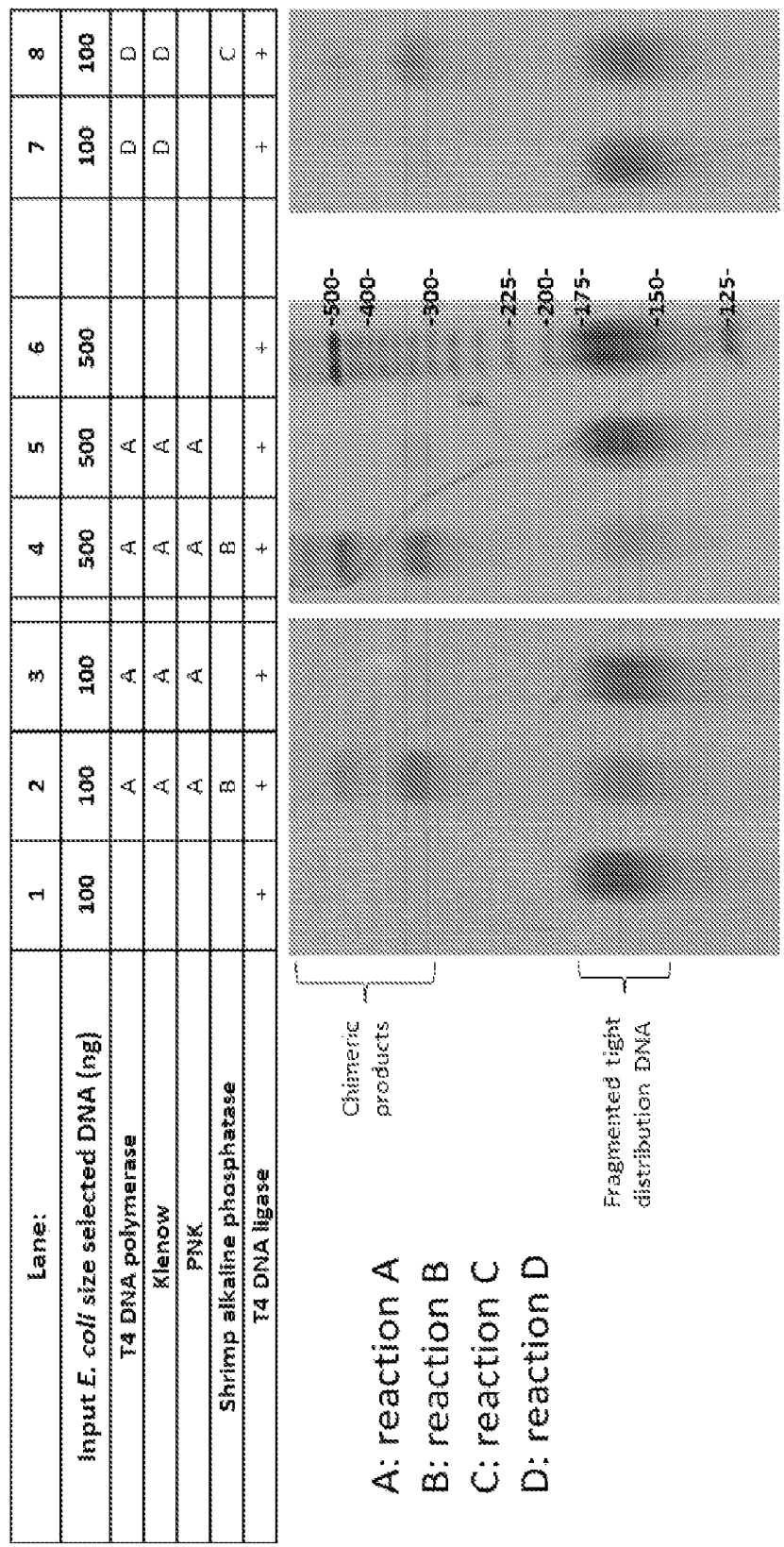

FIG. 27 Polishing is required for blunt ligation of physically sheared DNA and dephosphorylation prevents the formation of chimeric ligation products (Example 9)

Figure 28A:
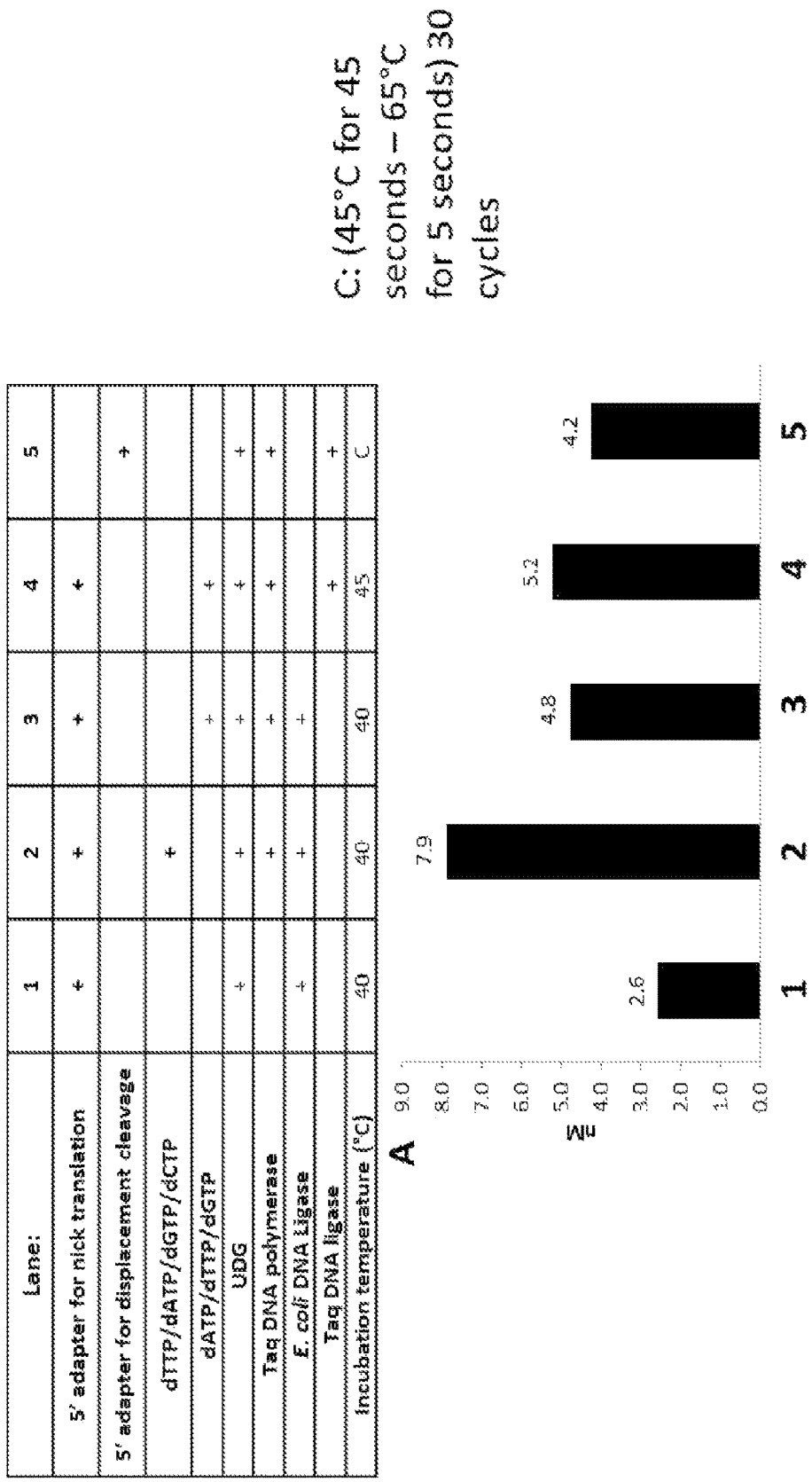
Figure 28B:
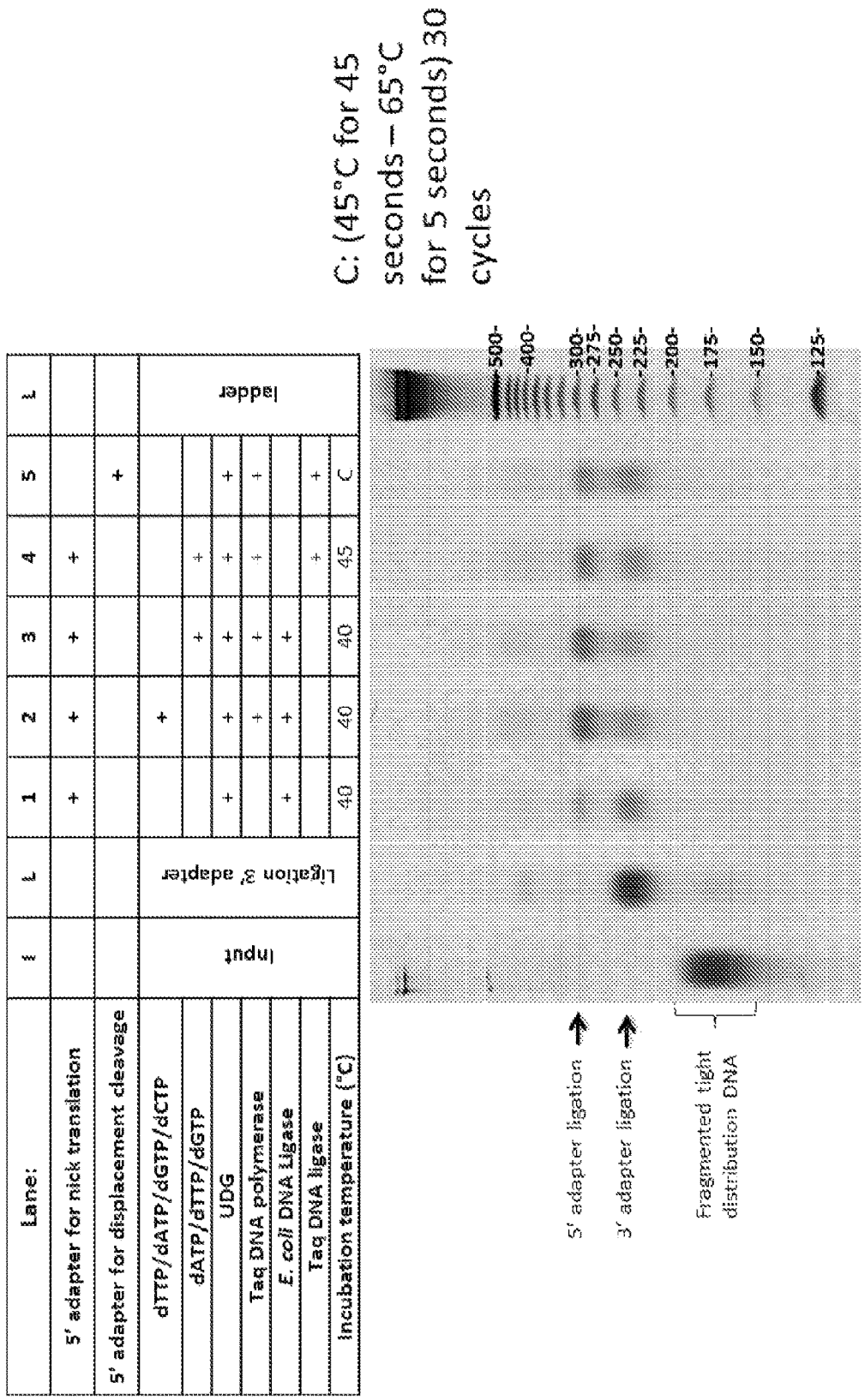
Figure 29A:
Figure 29A:
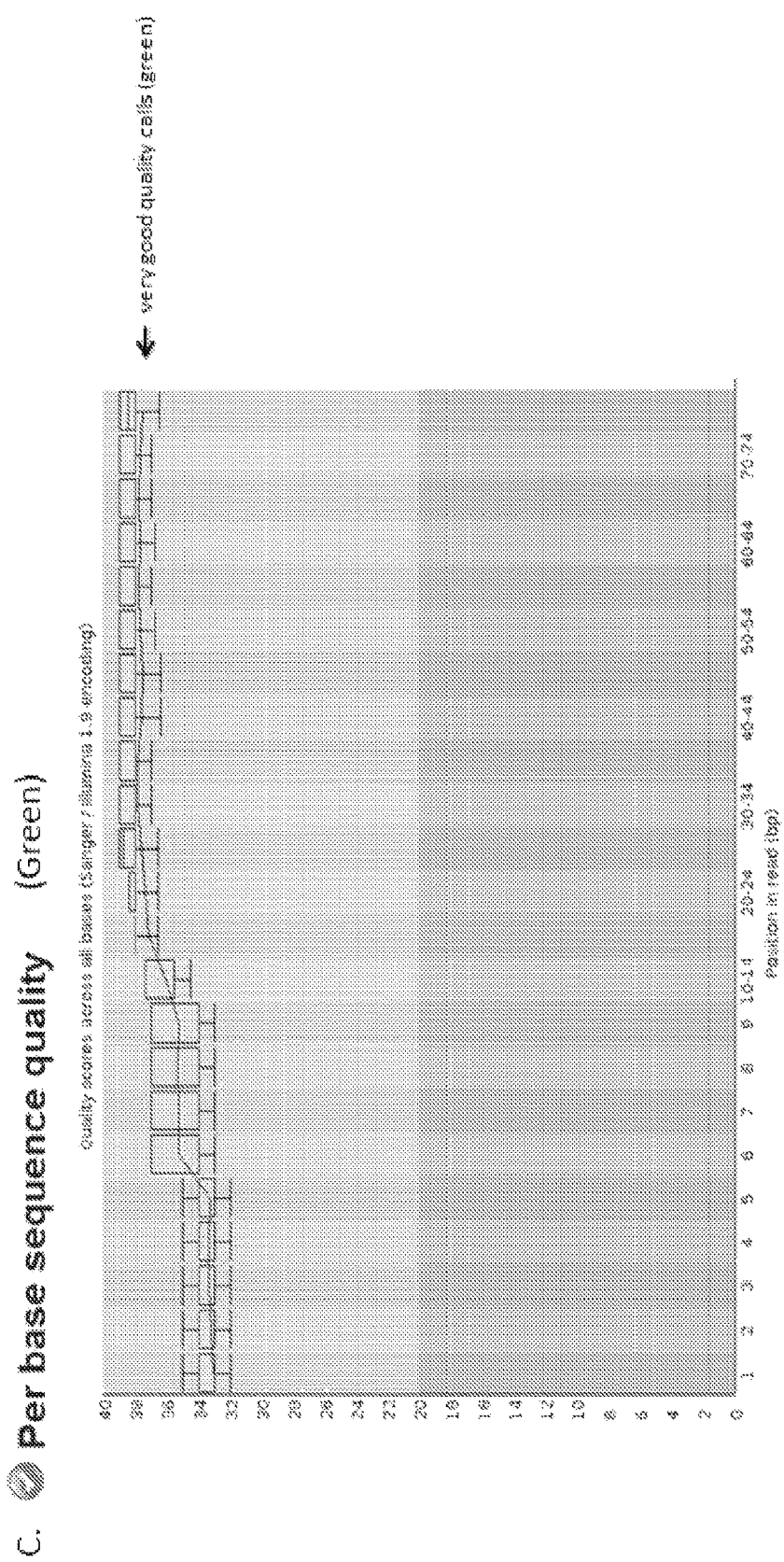
Figure 29B:
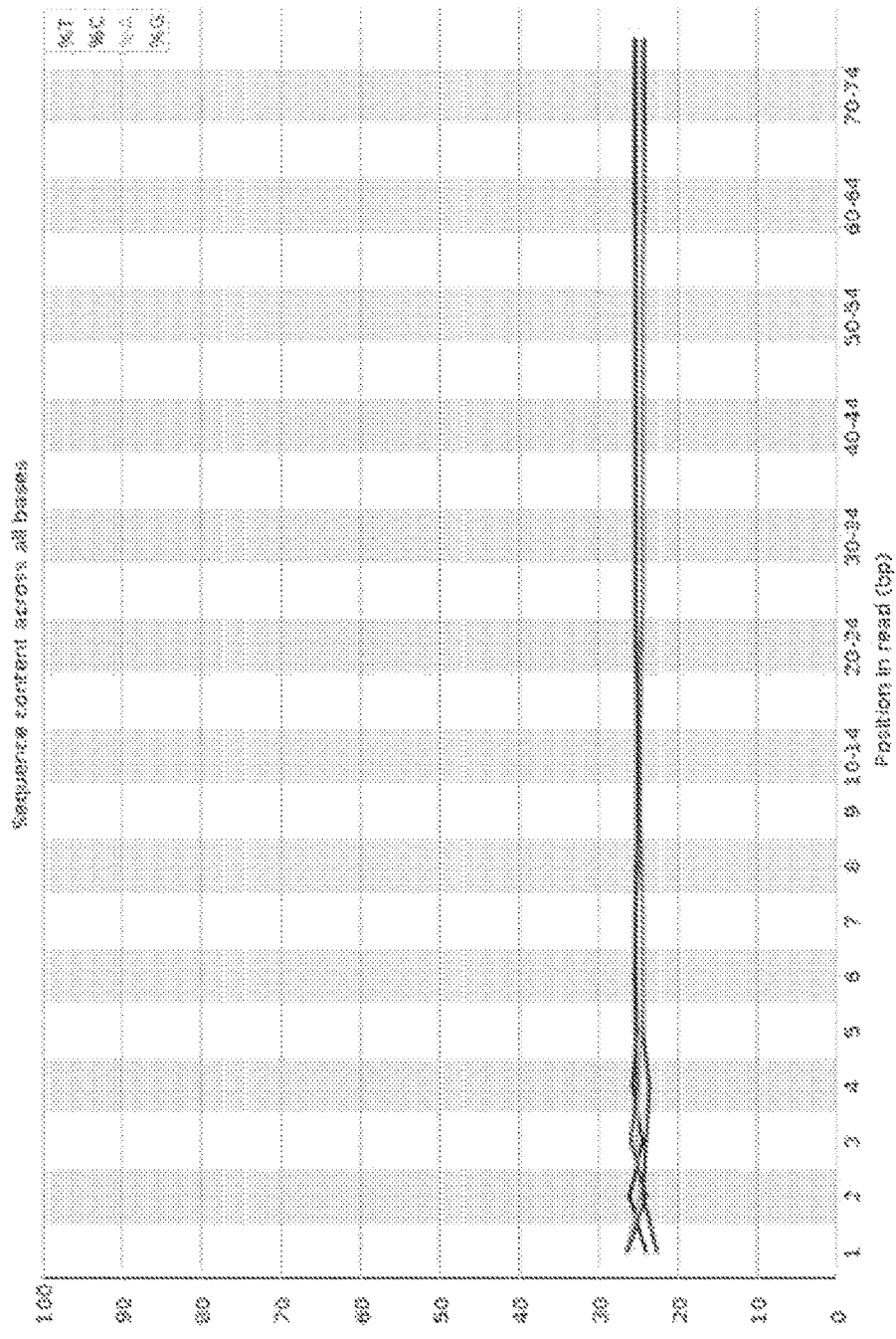
Figure 29B:
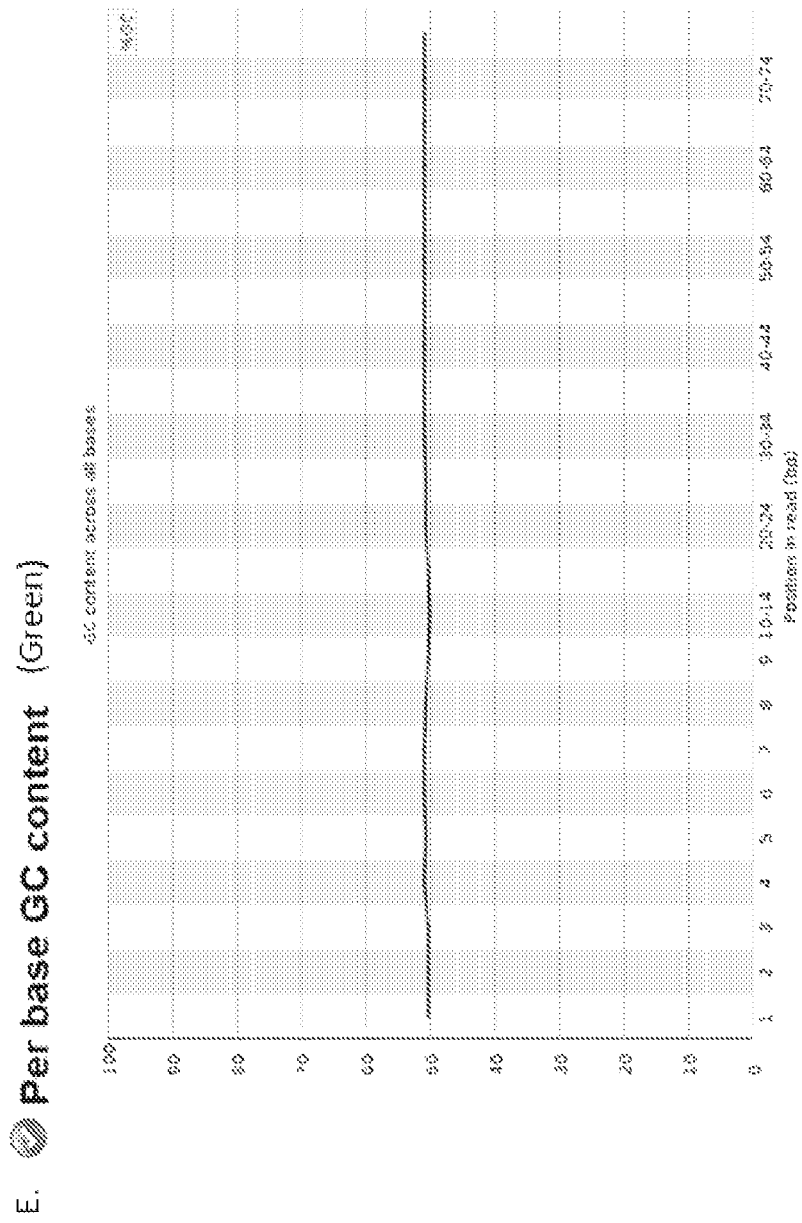
Figure 29B:
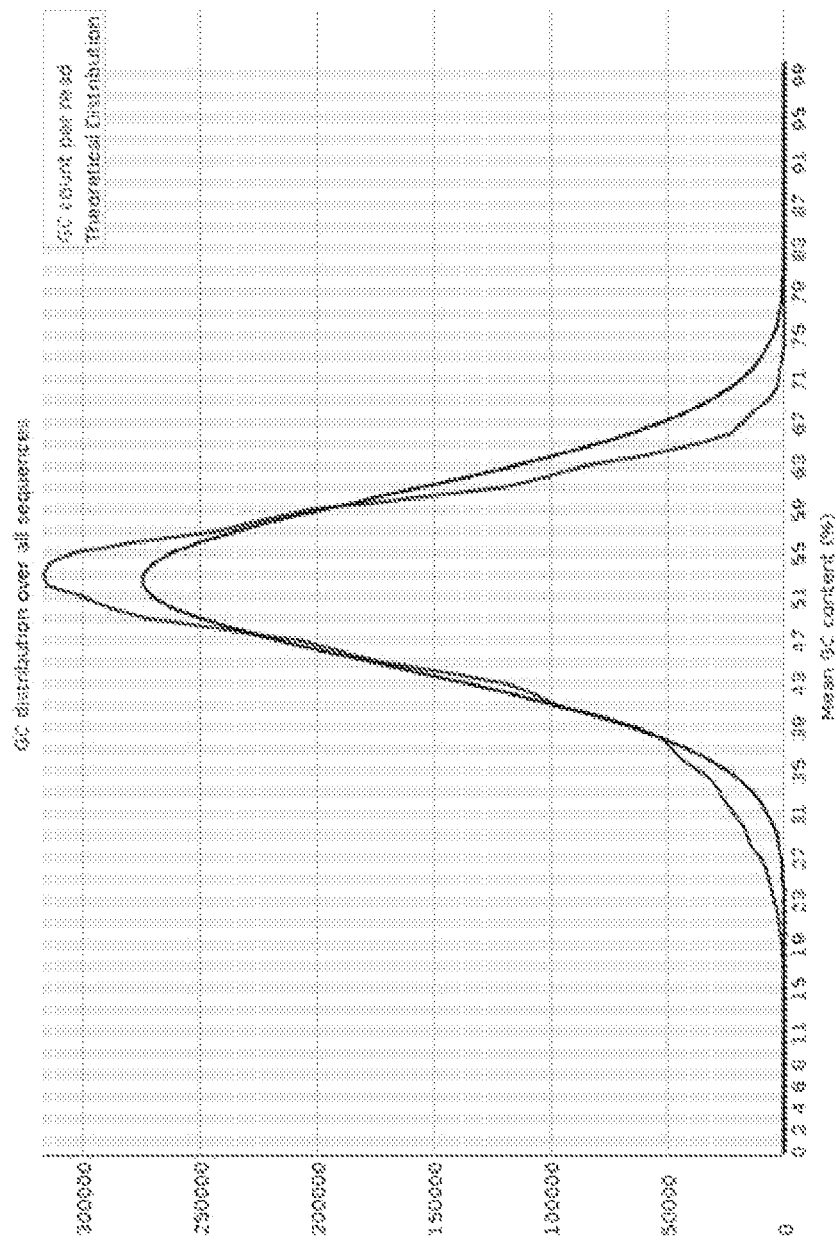
Figure 29B:
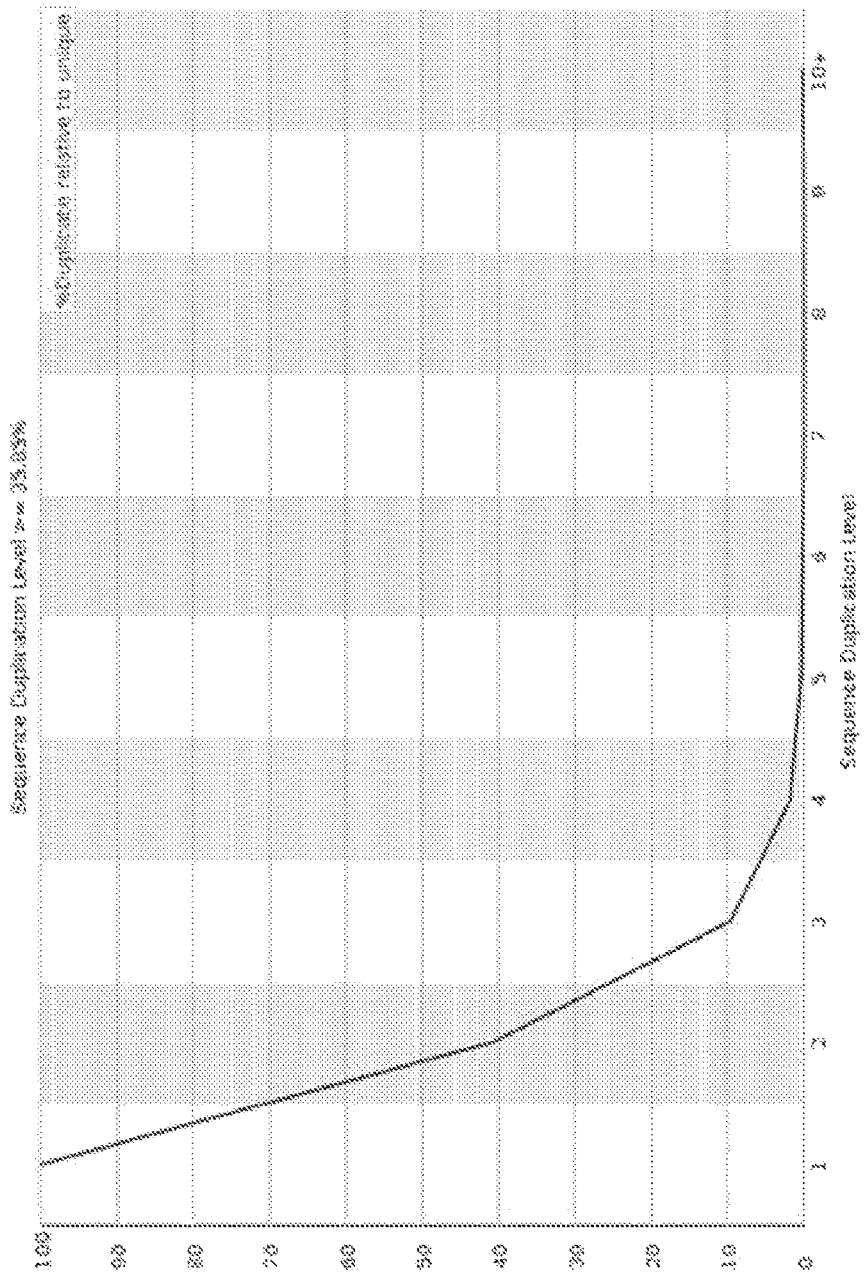
Figure 29C:
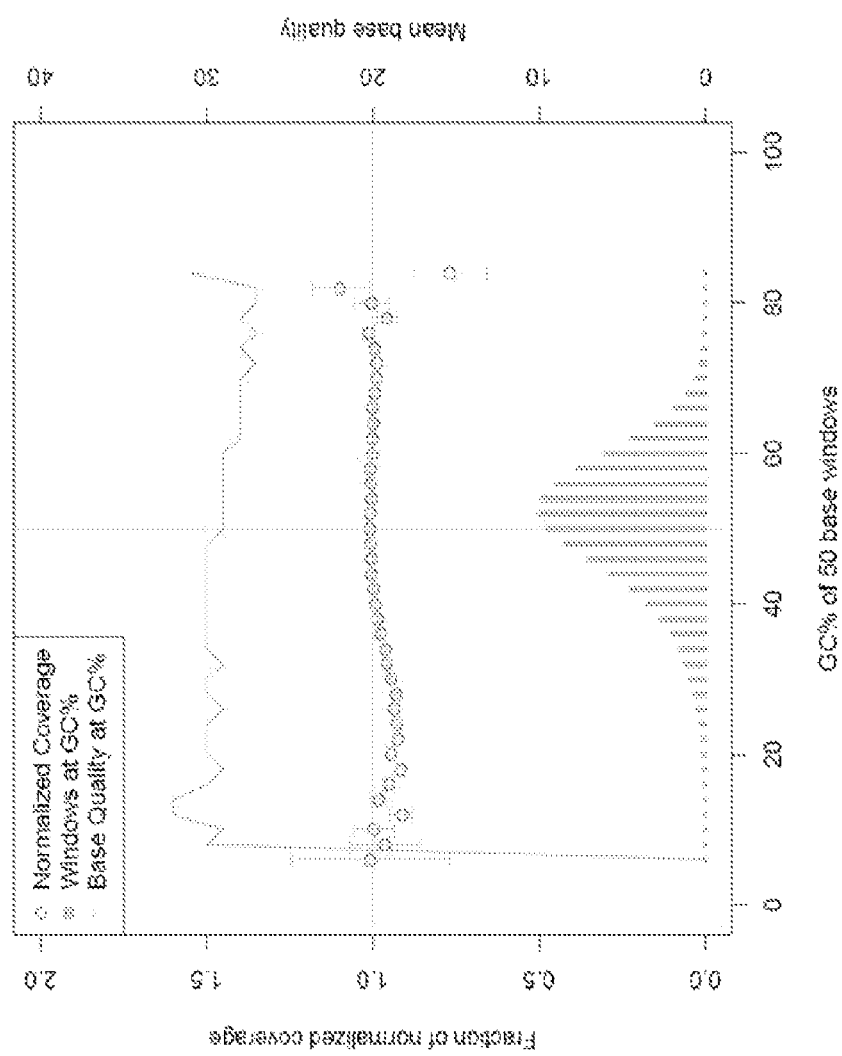

FIGS. 28 A and B. NGS Libraries have increased yield when prepared using 5' base trimming coupled to adapter ligation reaction (Example 10)

FIGS. 29 A, B, and C. Sequence analysis of NGS Libraries prepared using 5' base trimming coupled to adapter ligation (Example 11)

FIG. 30 depicts the structure of adapters, model substrates and oligonucleotide constructs described in Example 1.

FIG. 31 depicts FAM substrate molecules (see Example 1).

FIG. 32—depicts the structure of adapters as described in Example 2

Figure 33:
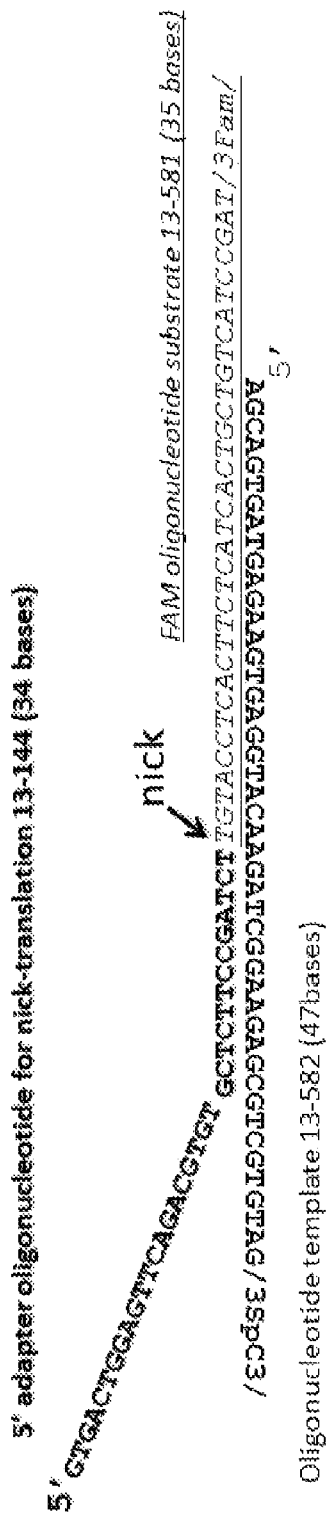

FIG. 33—depicts the oligonucleotide construct system as described in Examples 3, 4, 5, and 8.

Figure 34:
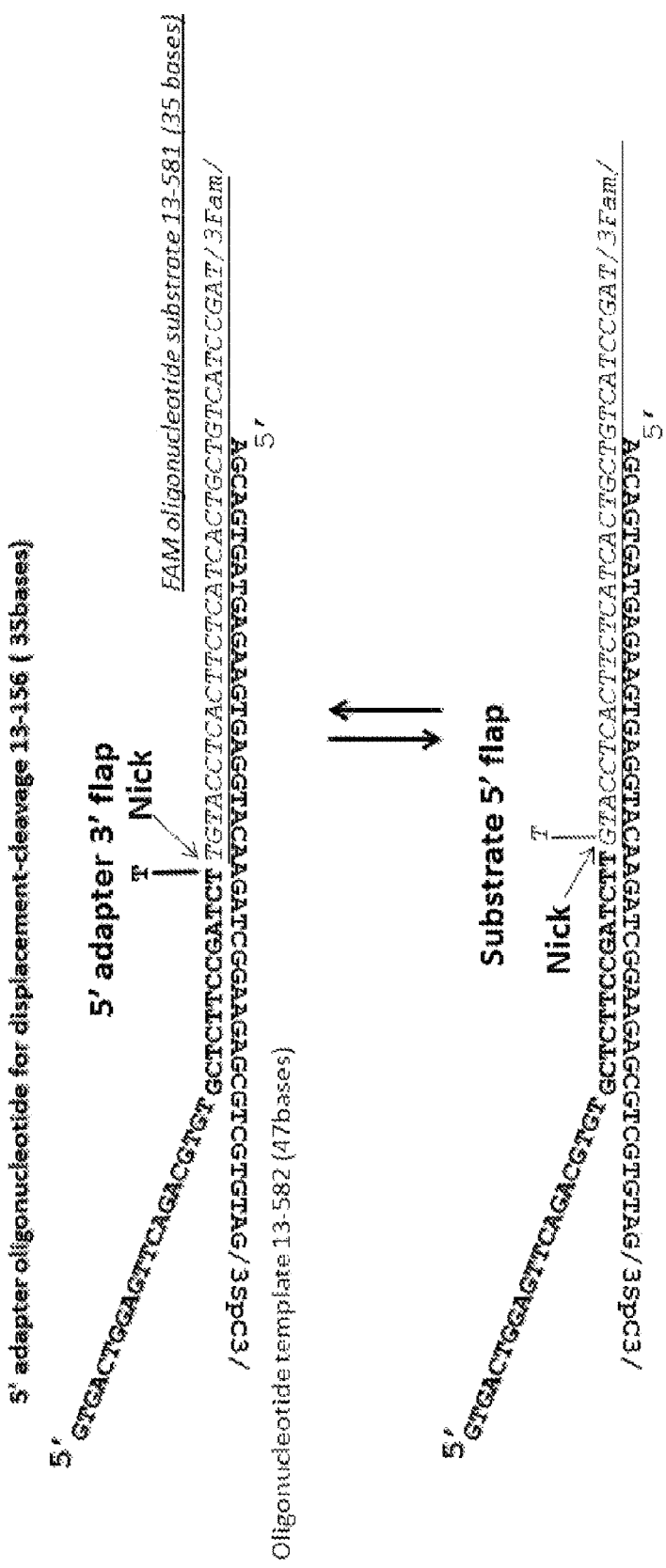

FIG. 34—depicts the oligonucleotide construct system as described in Example 6.

Figure 35:
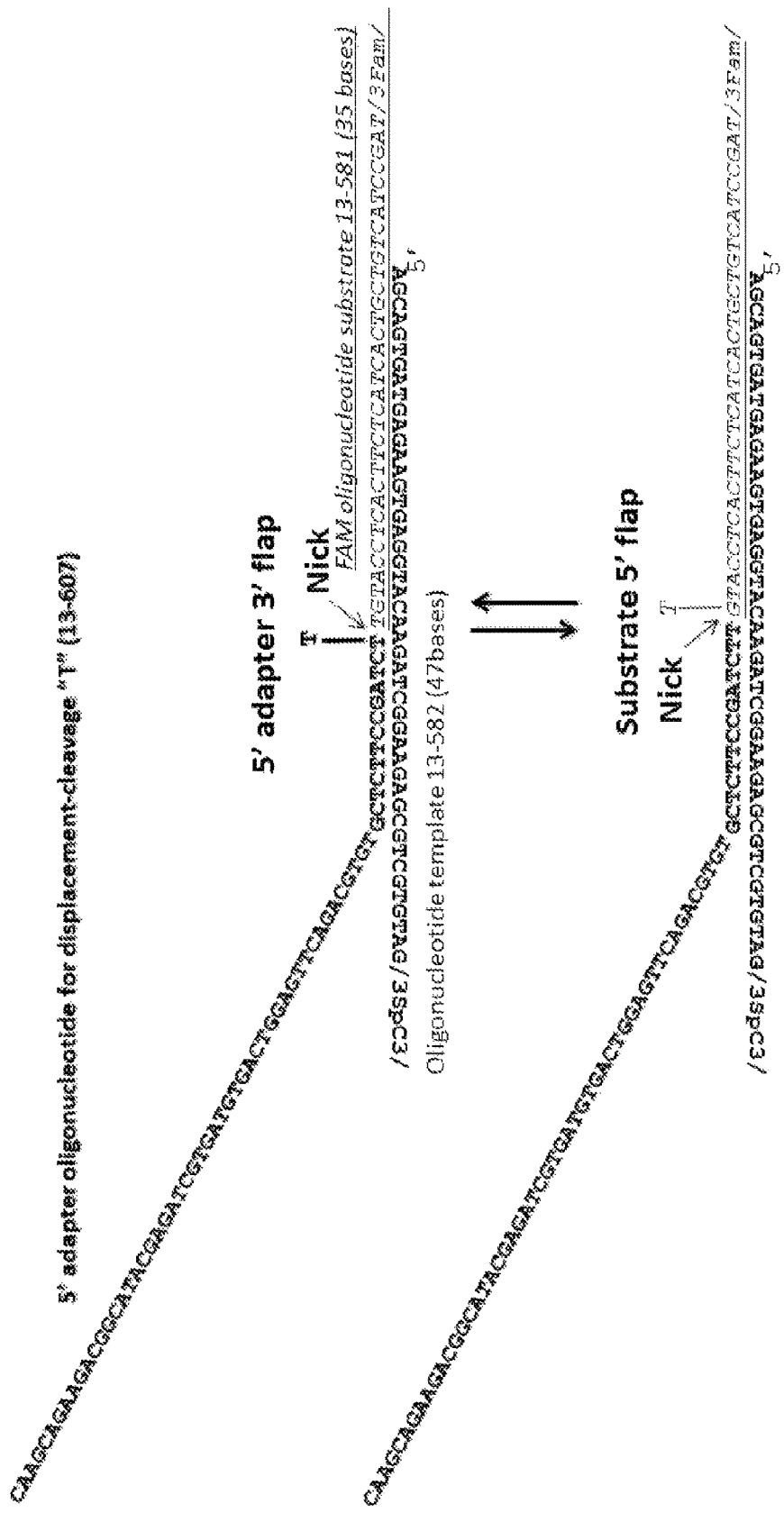

FIG. 35—depicts the oligonucleotide construct system as described in Example 7.

Figure 36:
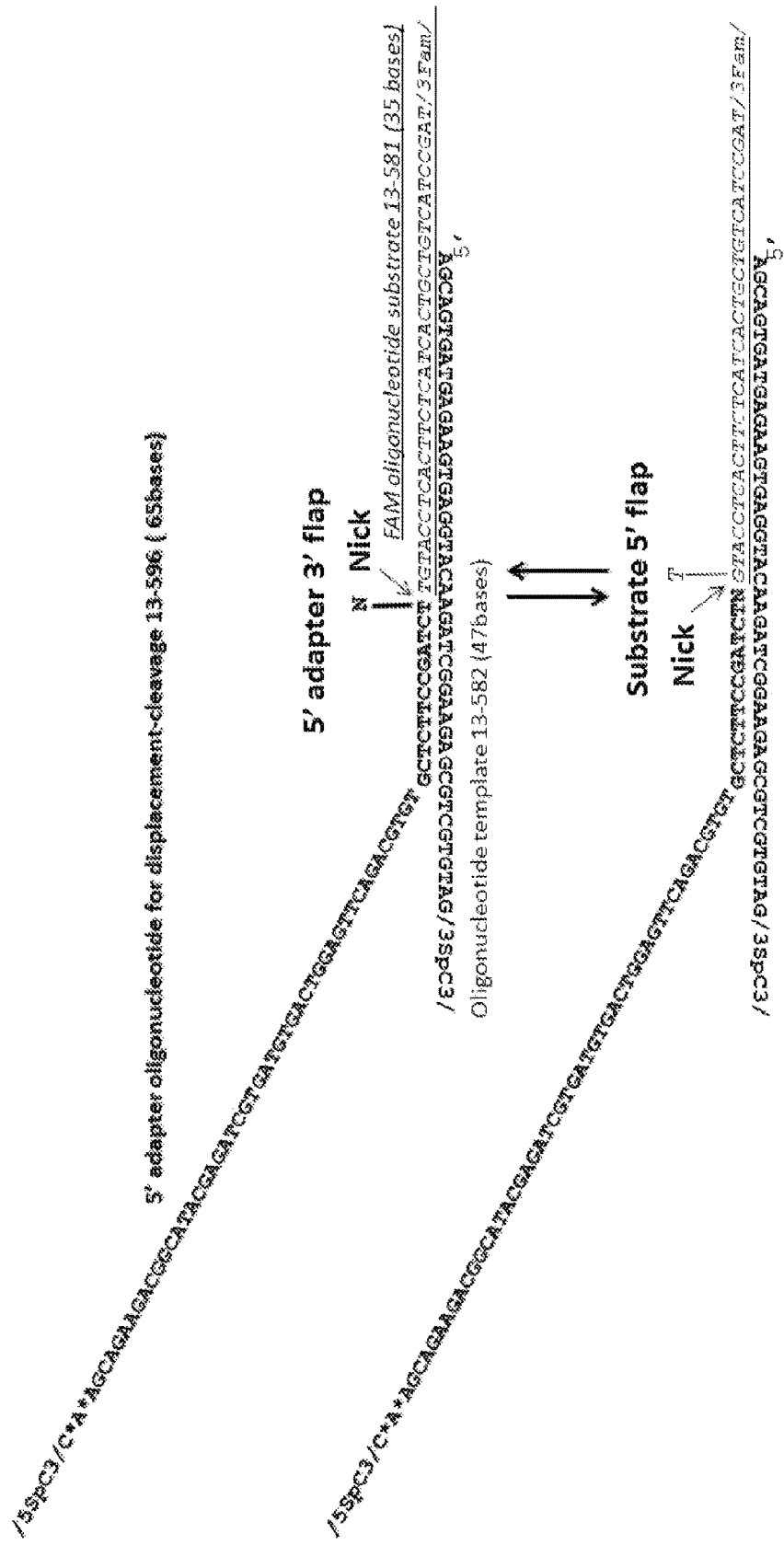

FIG. 36—depicts the oligonucleotide construct system as described in Example 7.

FIG. 37—depicts the structure of P7 and P5 adapters as described in Example 10.

FIG. 38—depicts the structure of P7 and P5 adapters as described in Example 11.

Figure 39:
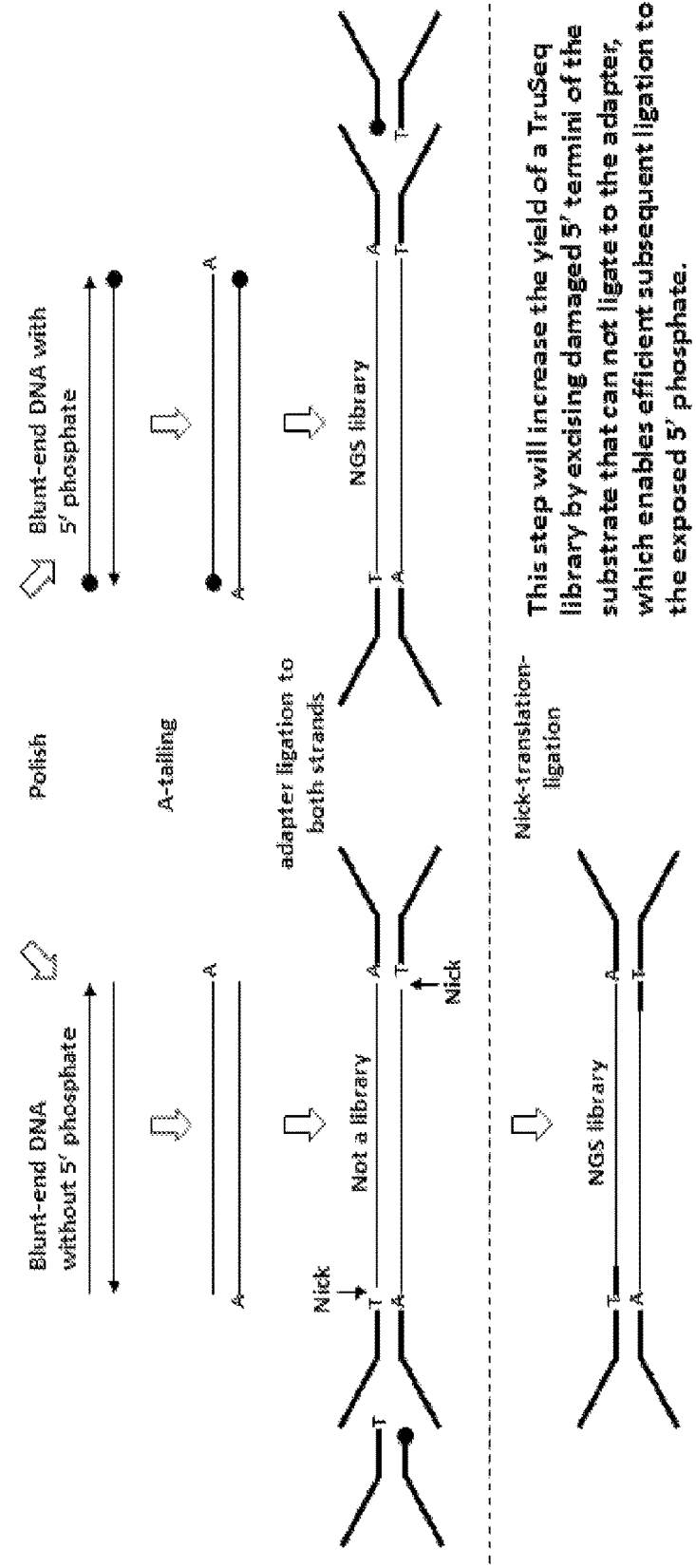

FIG. 39. Figure depicting a nick-translation-ligation step to improve genomic library yield.

FIG. 40. Figure depicting a method to eliminate formation of adapter dimers.

Figure 41:
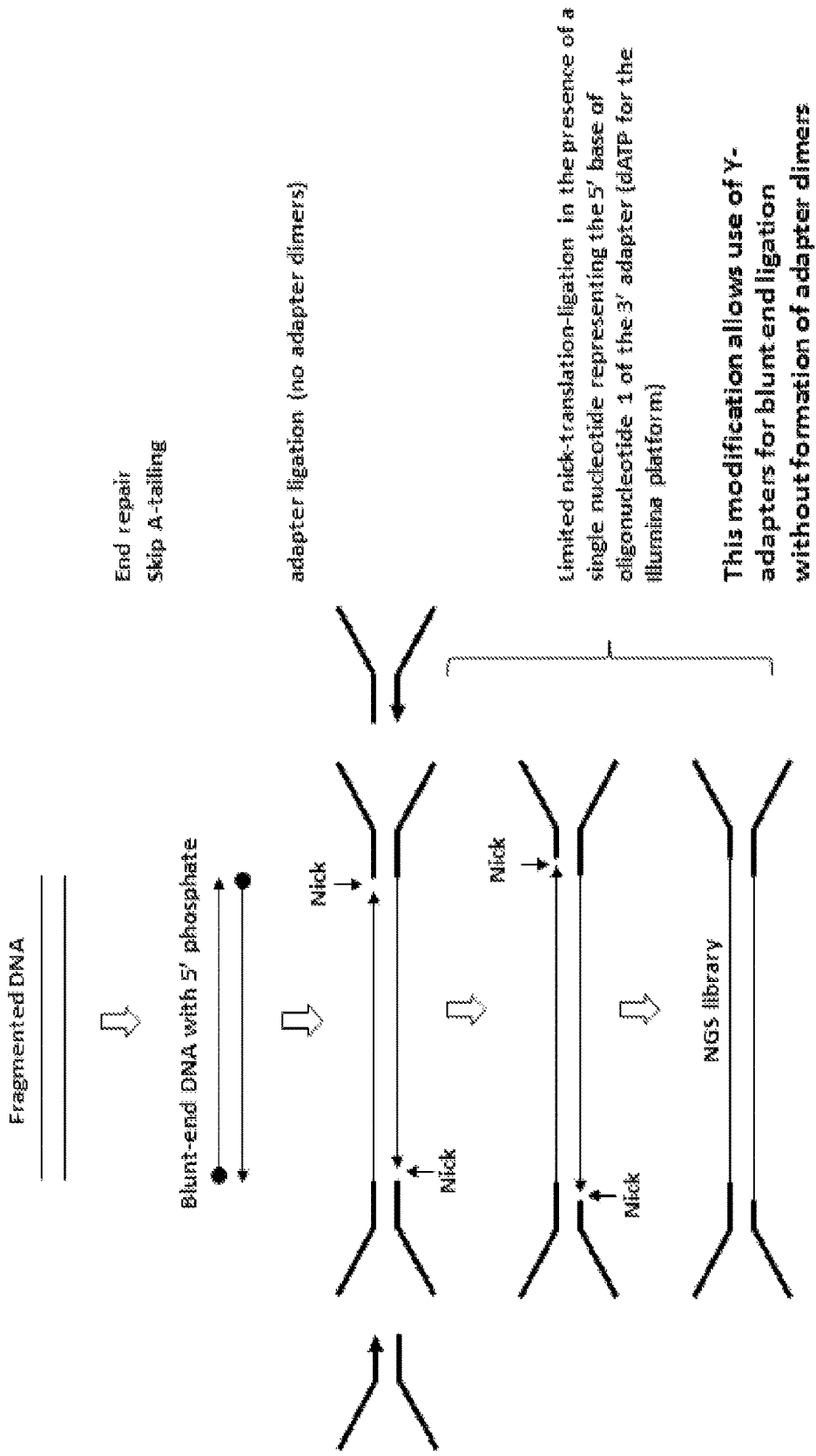

FIG. 41. Figure showing a modified low adapter-dimer protocol.

Figure 42:
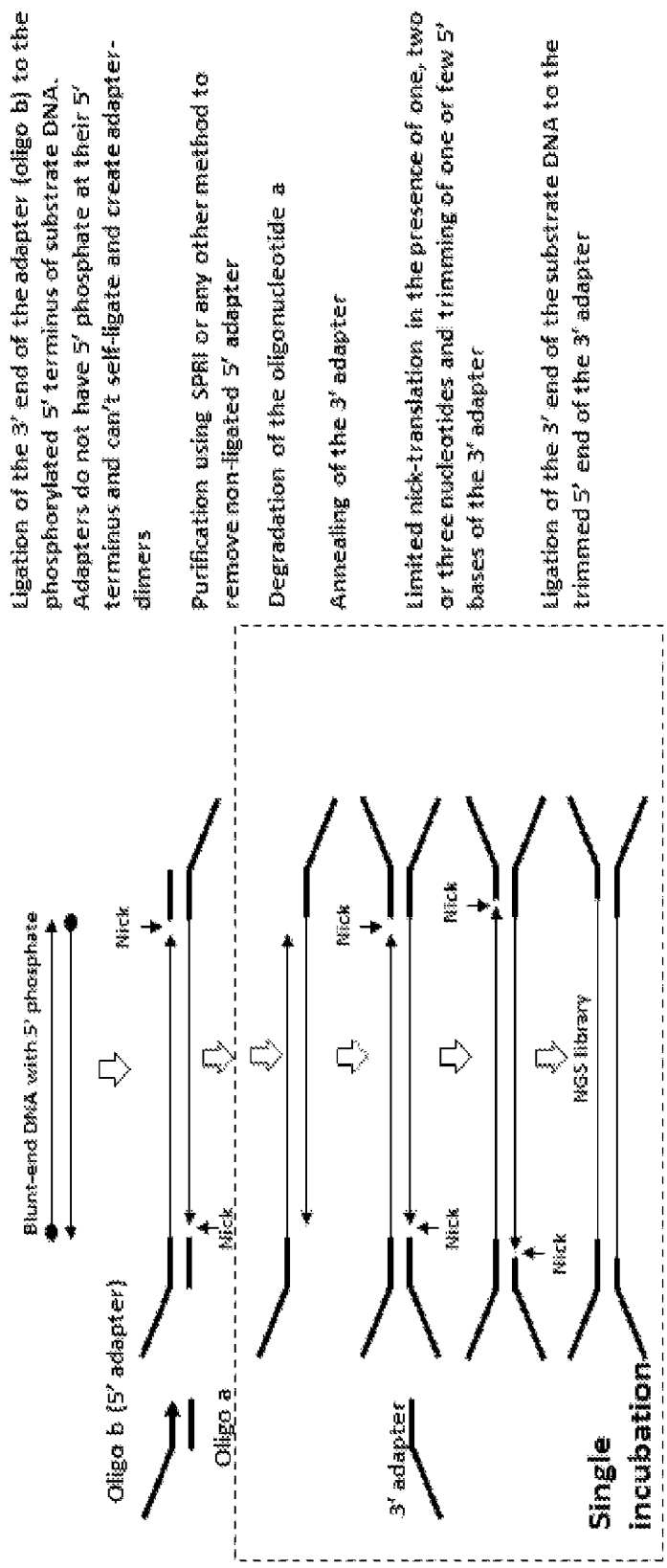
Figure 43:
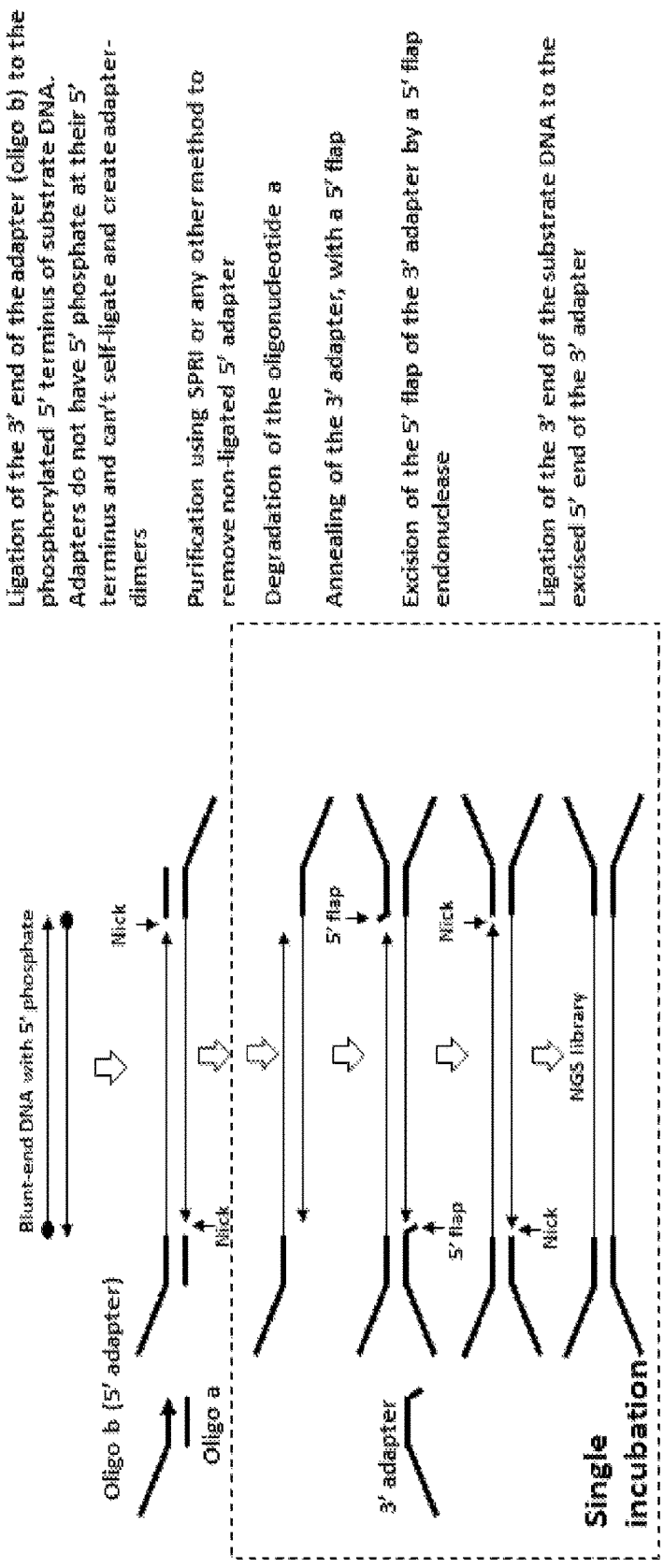

FIG. 42. Figure depicting an alternative modified low adapter dimer protocol using nick translation FIG. 43. Figure depicting an alternative modified low adapter dimer protocol using a 5' flap endonuclease.

Figure 44:
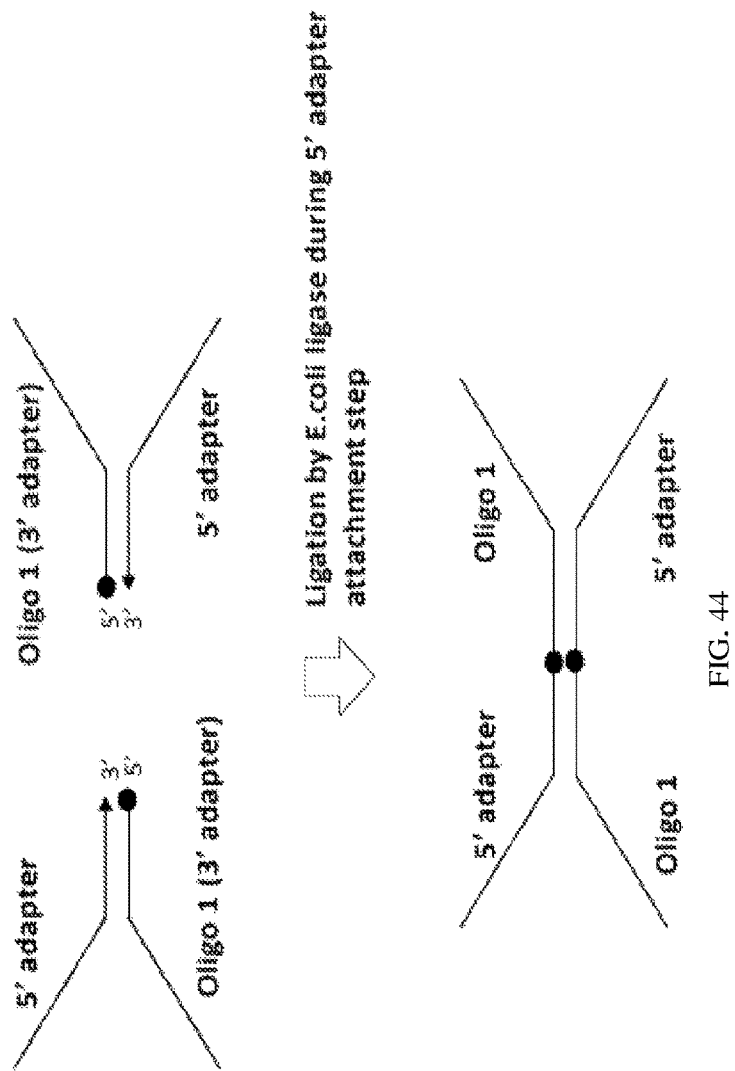

FIG. 44. How adapter dimers form using the sequential ligation library preparation method disclosed herein where residual oligonucleotide 1 of the 3' adapter from the first ligation reaction is carried over through the purification step into the second ligation reaction, where it anneals to the 5' adapter through a complementary sequence to form functional adapter dimer library molecules.

Figure 1:
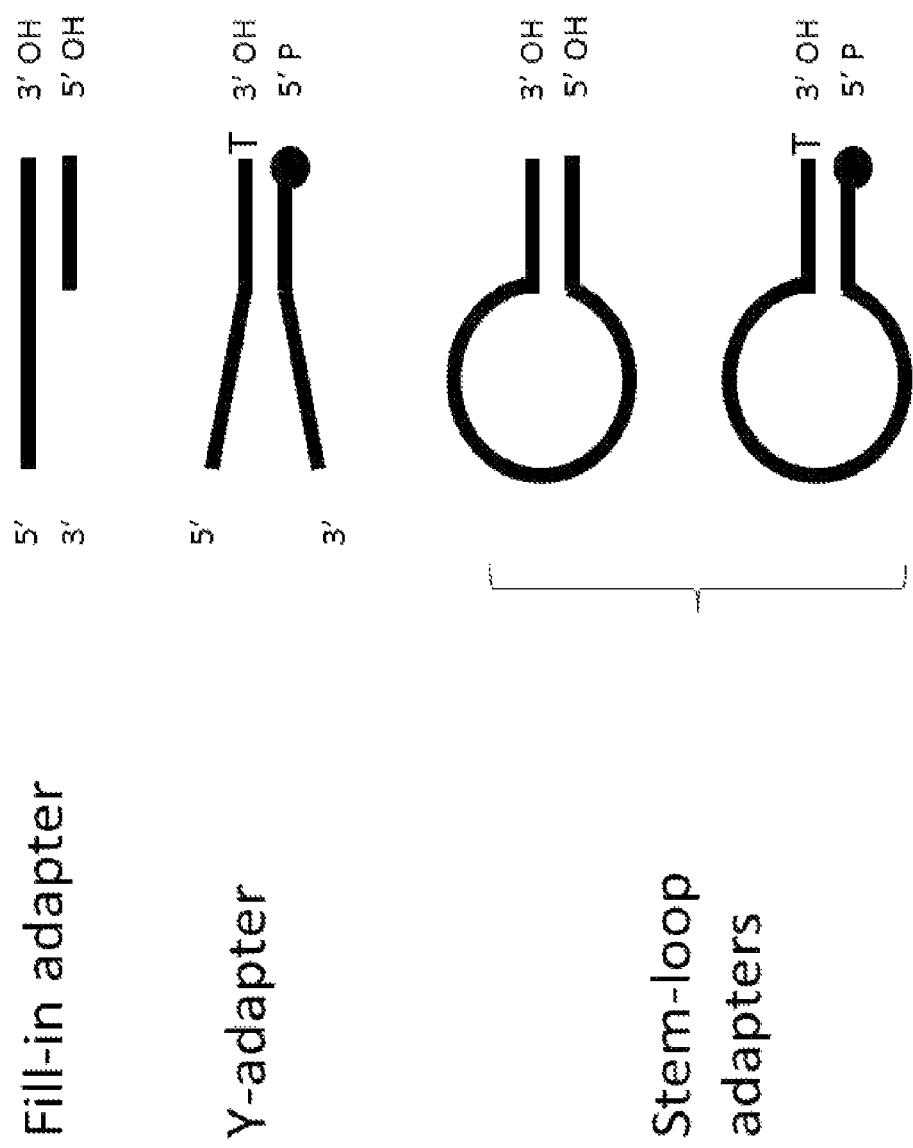
FIG. 1 Current NGS adapters
Fill-in adapter (blunt-ended or with T-overhang) with 3' and 5' hydroxyls
Y-adapter (with T-overhang) with 3' hydroxyl and 5' phosphate
Stem-loop adapter (blunt-ended or with T-overhang) with 3' hydroxyl and 5'hydroxyl or phosphate
FIGS. 2, A and B. Conventional adapter ligation chemistries
FIG. 3 3' and 5' adapter features
FIG. 4 5' adapter ligation by nick-translation
Steps include:
substrate molecule dephosphorylation
substrate molecule polishing/blunt end generation
3' adapter ligation
partial degradation of the 3' adapter and annealing of the 5' adapter
polymerase extension of the 5' adapter by nick-translation
ligation of the extended 5' adapter to the exposed 5' phosphate of the DNA substrate
FIG. 5 5' adapter ligation by displacement-cleavage
Steps include:
1—substrate molecule dephosphorylation
2—substrate molecule end polishing/blunt end generation
3—3' adapter ligation
4—Partial degradation of the 3' adapter and annealing of the 5' adapter
5—Displacement of the 5' base(s) of the DNA fragment and annealing of the 3' base(s) of the 5' adapter
6—Cleavage of the displaced 5' base(s) of DNA by a 5'-flap endonuclease
7—Ligation of the 3' end of the 5' adapter to the exposed 5' phosphate of the substrate DNA
FIG. 6 Adapter ligation can be achieved with two incubations
5'-adapter attachment by coupled annealing-nick-translation-ligation is achieved in 2 incubations where the 1$^{st}$ incubation is a 3'-adapter attachment, and the 2$^{nd}$ incubation combines 3 reactions that occur sequentially: (1) annealing of the 5'-adapter, (2) 5'-adapter extension by DNA polymerase with nick-translation activity (excision of damaged 5' terminus of substrate DNA), and (3) ligation of the 5'-adapter to the exposed 5'-phosphate of the substrate DNA
5'-adapter attachment by coupled annealing-base excision-ligation is achieved in 2 incubations where the 1$^{st}$ incubation is a 3'-adapter attachment, and the 2$^{nd}$ incubation combines 3 reactions that occur sequentially: (1) annealing of the 5'-adapter with one or several random bases at the 3'-end and displacement of one or several terminal 5'-bases of substrate DNA, (2) cleavage of displaced 5-bases by 5'-flap endonuclease (excision of damaged 5' terminus of substrate DNA), and (3) ligation of the 5'-adapter to the exposed 5'-phosphate of the substrate DNA
FIG. 7 Generation of a single-stranded 3' overhang
A 3'-adapter overhang sequence can be added enzymatically by at least 4 different methods:
by conventional ligation using T4 DNA ligase
by single-strand DNA (RNA) ligase
by conventional homopolymer tailing with terminal transferase
by controlled tailing and simultaneous adapter ligation using terminal transferase, DNA ligase and attenuator-adapter molecule. See International patent application number PCT/US13/31104, filed Mar. 13, 2013, incorporated by reference in its entirety.
Figure 45:
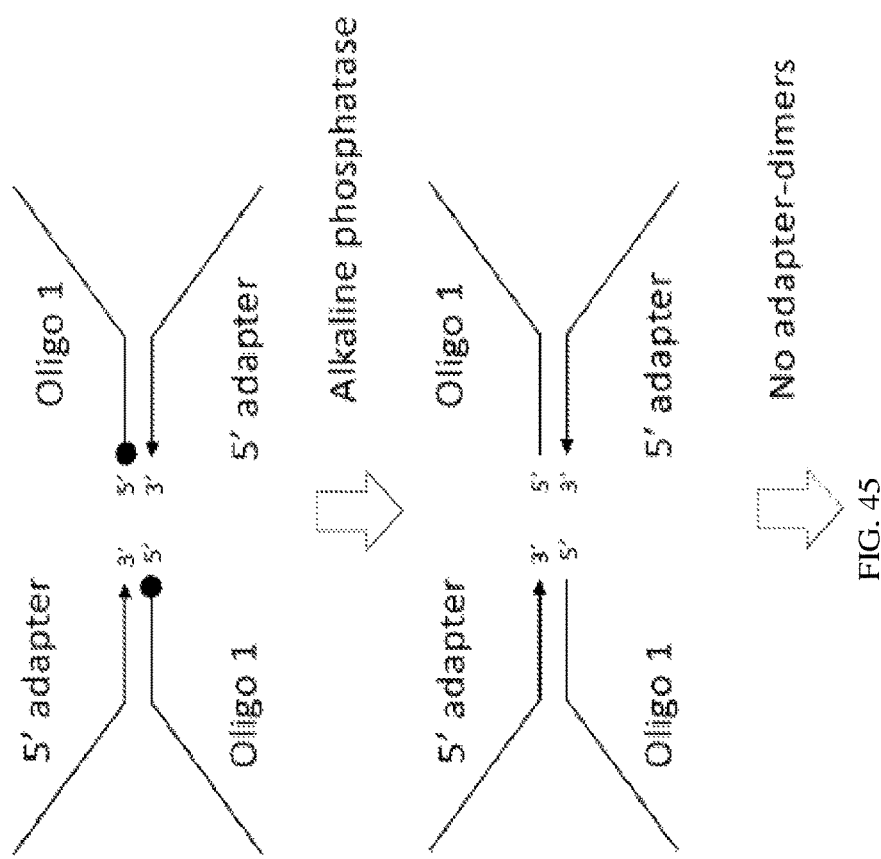

FIG. 45. How adapter dimer formation as depicted in FIG. 1 can be prevented by inactivating (dephosphorylating) the residual 3' adapter oligonucleotide 1 with a phosphatase enzyme that renders the carried over 3' adapter incapable of ligation in the 5' adapter ligation step.

FIG. 46. How an adapter dimer blocker specifically inhibits the 3' adapter/5' adapter ligation reaction to prevent adapter dimer formation while remaining inert to the desired ligation reaction of the 5' adapter to the substrate molecule.

Figure 47:
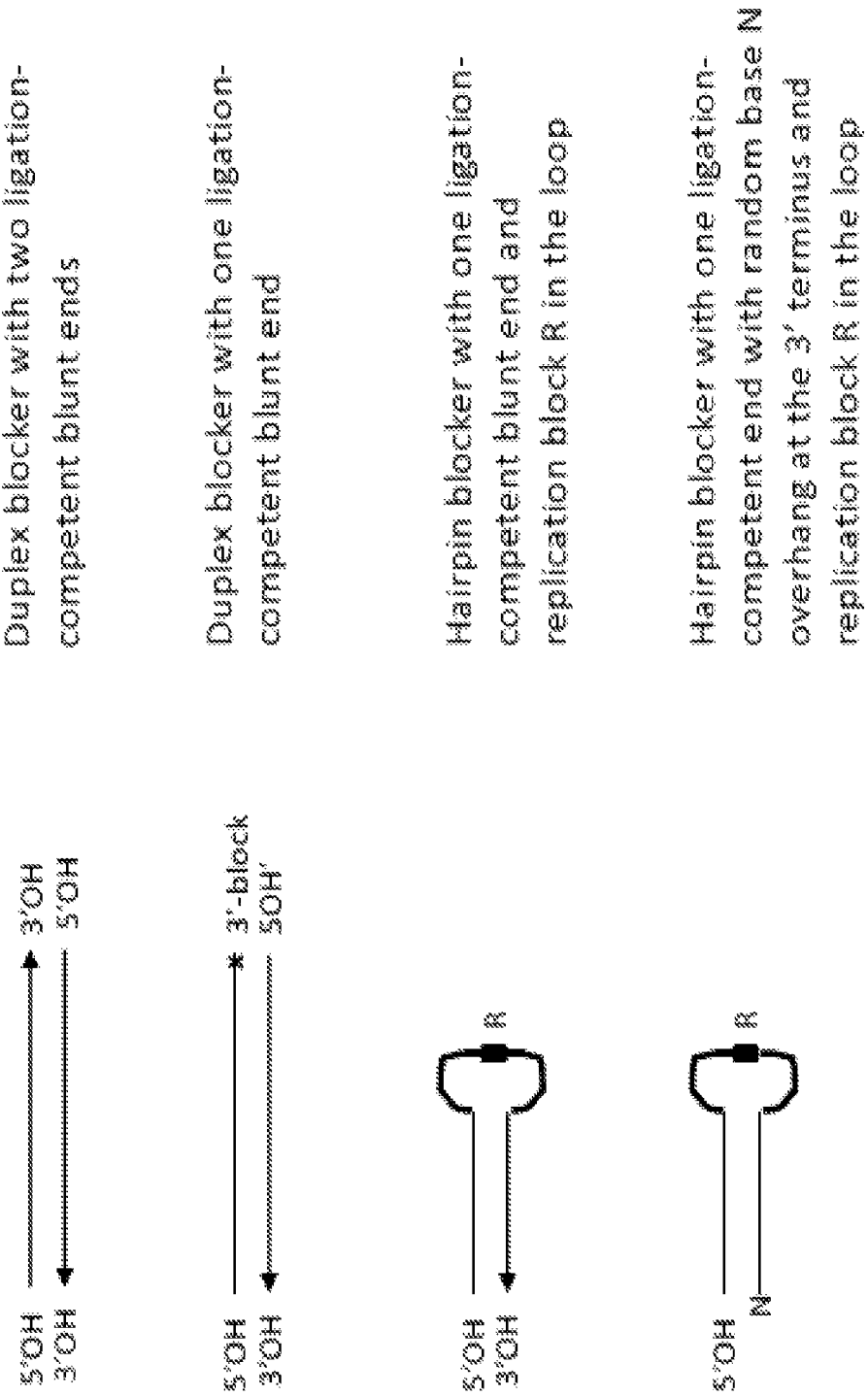

FIG. 47. Types of adapter dimer blockers, which can be comprised of a DNA duplex with either one or two ligation competent termini, or which can be comprised of a single oligonucleotide DNA hairpin with a replication blocking modification in the loop structure and either a blunt end or a single N base 3' overhang.

Figure 48:
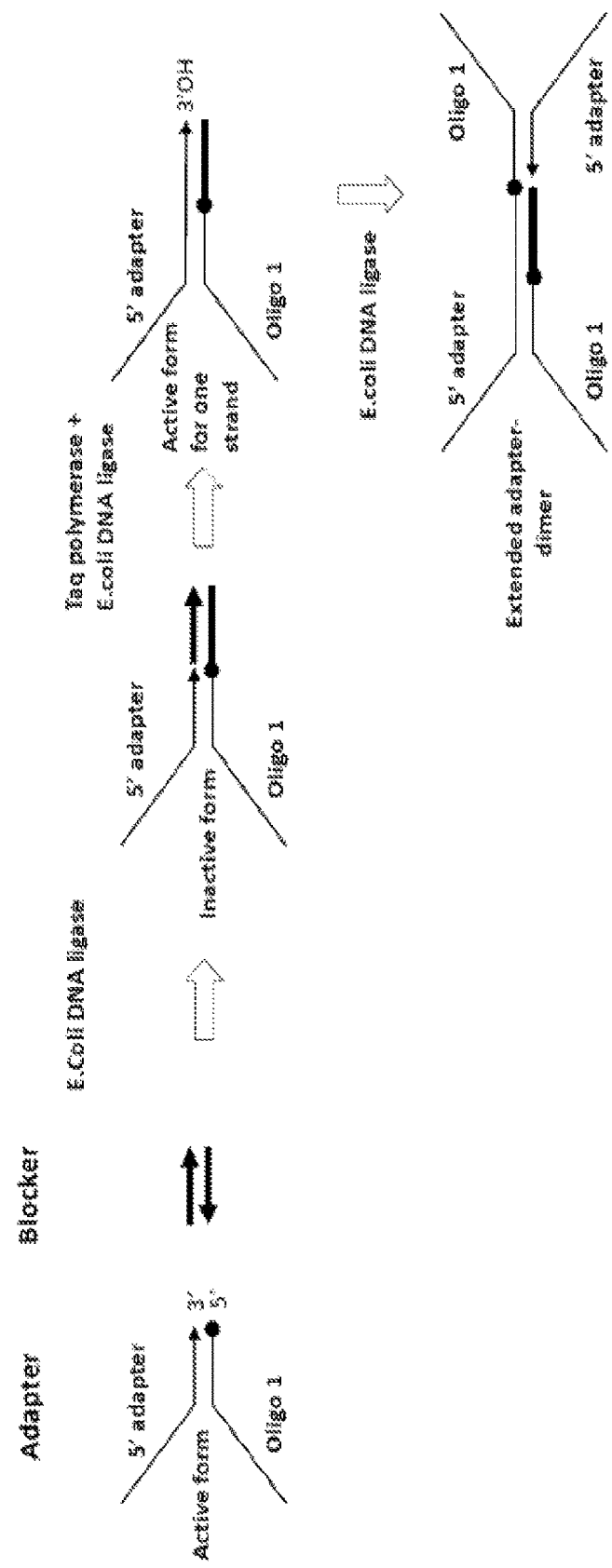

FIG. 48. How adapter dimer blockers comprised of a duplex DNA with two ligation competent ends create ligation products with the 3' adapter oligonucleotide 1/5' adapter duplex that do not result in functional adapter dimer molecules.

Figure 49:
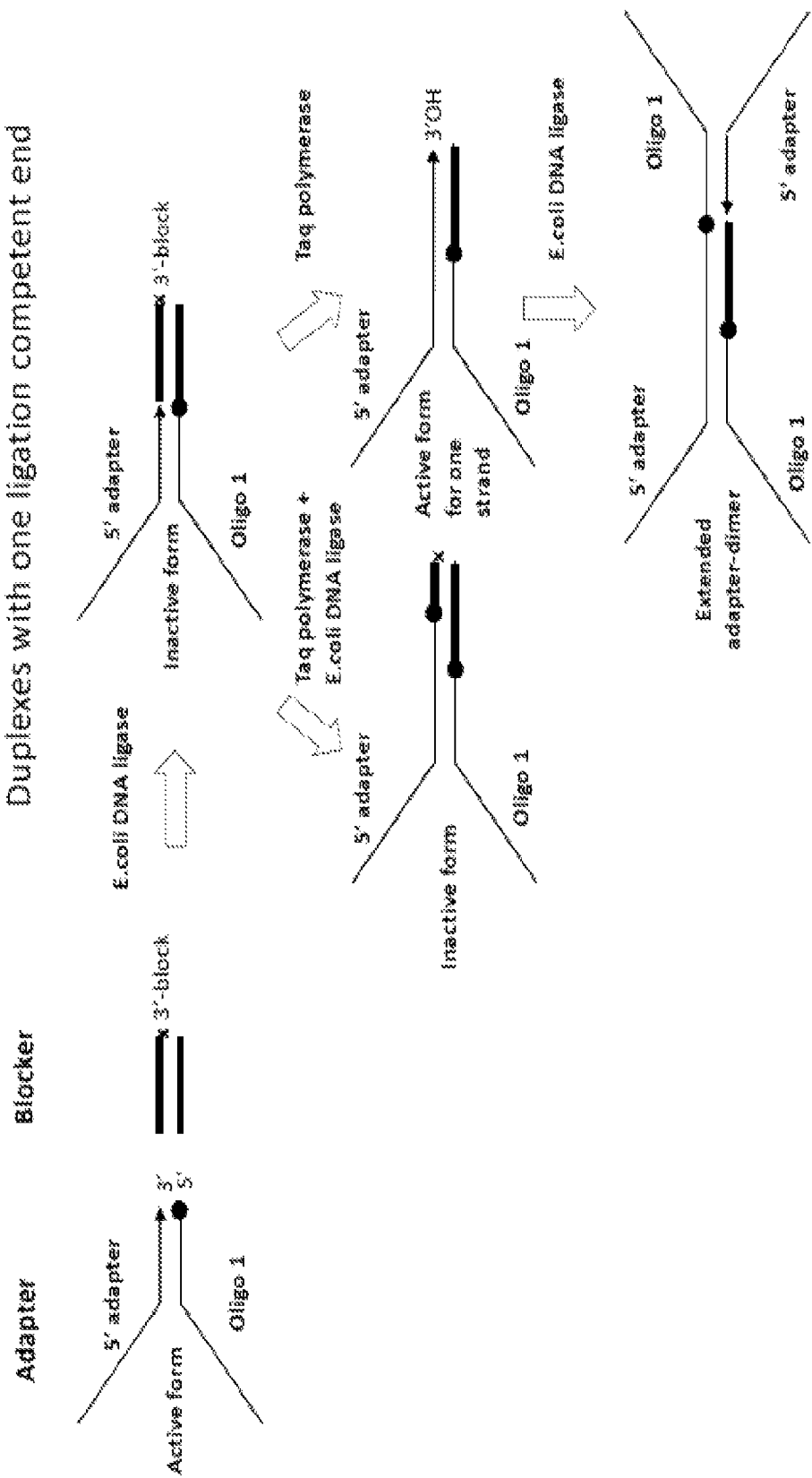

FIG. 49. How adapter dimer blockers comprised of a duplex DNA with one ligation competent end create ligation products with the 3' adapter oligonucleotide 1/5' adapter duplex that do not result in functional adapter dimer molecules.

Figure 50:
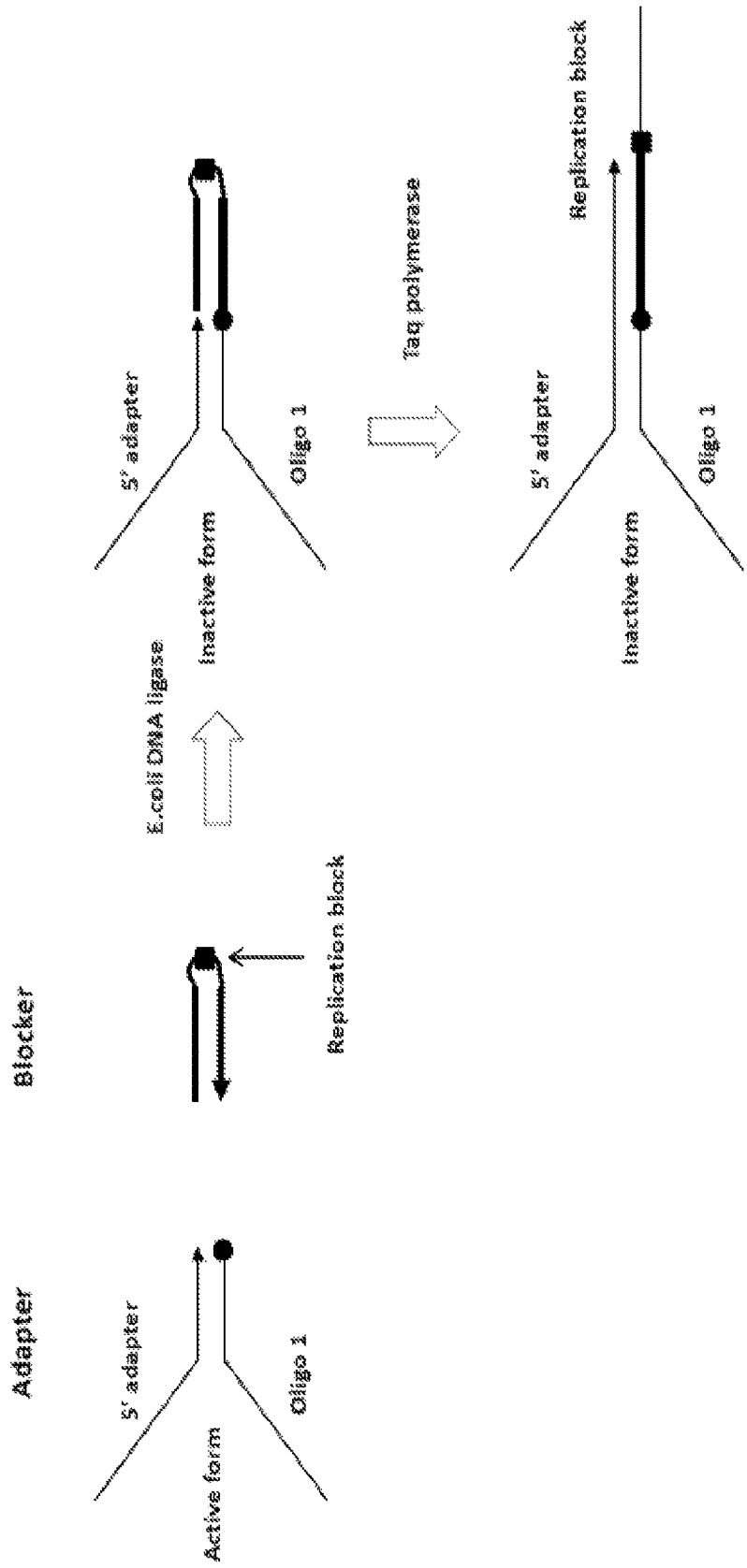

FIG. 50. How adapter dimer blockers comprised of a DNA oligonucleotide hairpin with one ligation competent blunt end and replication blocker in the loop structure can create ligation products with the 3' adapter oligonucleotide 1/5' adapter duplex that do not result in functional adapter dimer molecules.

Figure 51:
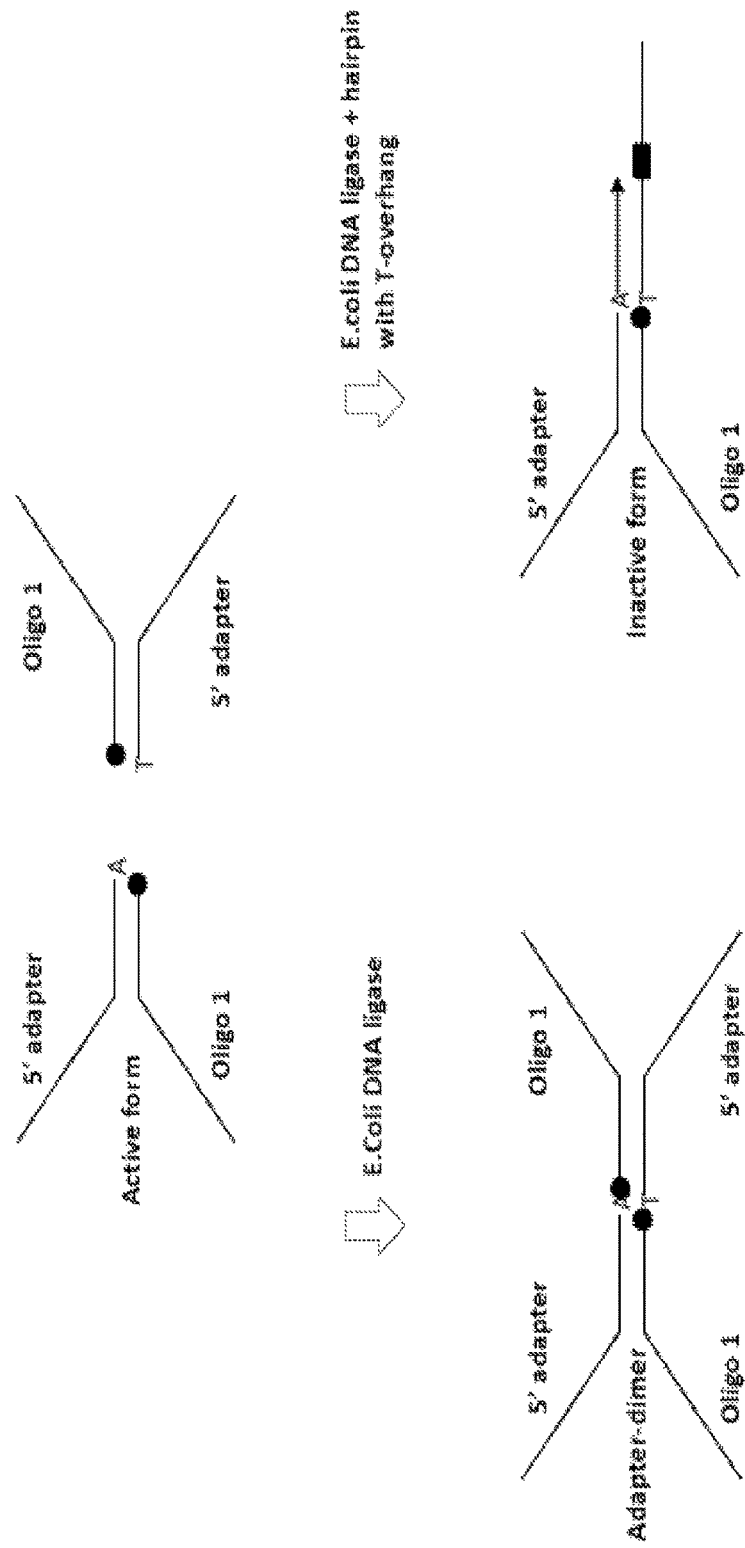

FIG. 51. How adapter dimer blockers comprised of a DNA oligonucleotide hairpin with one ligation competent single base N 3' overhang and replication blocker in the loop structure can create ligation products with the 3' adapter oligonucleotide 1/5' adapter duplex that do not result in functional adapter dimer molecules.

Figure 52:
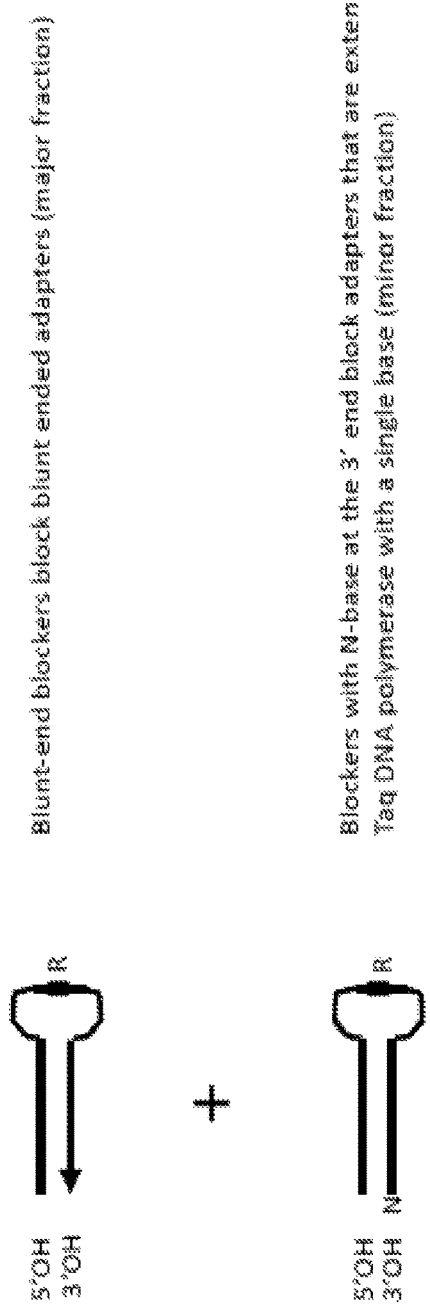

FIG. 52. Depicts an exemplary composition of a mixture of hairpin blockers depicted in FIGS. 7 and 8 that prevent adapter dimer formation both from original blunt end 3' adapter/5' adapter duplexes as well as duplexes that have a single base addition by Taq polymerase that is present in the 5' adapter ligation reaction.

DETAILED DESCRIPTION OF THE INVENTION

The invention describes a highly efficient method of adapter ligation to the ends of fragmented double-stranded DNA molecules. Such DNA molecules are referred to herein as "substrate molecules." In one aspect, the method comprises a single incubation that includes (1) annealing of a 5' adapter to a pre-existing 3' overhang on a substrate molecule, preferably a 3' adapter, (2) removal of a damaged base from the 5'-termini of the substrate molecules, which enables (3) efficient ligation of the 5' adapter to the exposed 5'-phosphate of the substrate molecules. In another aspect, the method comprises two incubations, where in the first incubation a 3' adapter is ligated to the substrate molecule, and in the second incubation the 5' adapter is ligated to the substrate molecule, as described above (see FIG. 6). In various embodiments, the disclosure further provides methods that comprise additional steps that occur prior to the one or two ligation steps, including: (i) a dephosphorylation reaction, (ii) a polishing reaction to excise damaged 3' termini and generate a blunt end, and (iii) an adenylation reaction; various combinations of the steps are contemplated by the disclosure, and are discussed in further detail below.

The term "reaction conditions" or "standard reaction conditions" as used herein means conditions according to manufacturer's instructions. It is understood that all enzymes herein disclosed are used under standard reaction conditions, unless indicated otherwise. The term "first polynucleotide" as used herein is used interchangeably with "3' adapter" and the term "second polynucleotide" as used herein is used interchangeably with "5' adapter".

As used herein, a "processed" substrate molecule is one to which a 5' adapter has been attached.

Substrate Molecule

It is contemplated that a substrate molecule is obtained from a naturally occurring source or it can be synthetic. The naturally occurring sources include but are not limited to genomic DNA, cDNA, DNA produced by whole genome amplification, primer extension products comprising at least one double-stranded terminus, and a PCR amplicon. The naturally occurring source is, in various embodiments, a prokaryotic source or a eukaryotic source. For example and without limitation, the source can be a human, mouse, virus, plant or bacteria.

As used herein, an "amplicon" is understood to mean a portion of a polynucleotide that has been synthesized using amplification techniques.

If the source of the substrate molecule is genomic DNA, it is contemplated that in some embodiments the genomic DNA is fragmented. Fragmenting of genomic DNA is a general procedure known to those of skill in the art and is performed, for example and without limitation in vitro by shearing (nebulizing) the DNA, cleaving the DNA with an endonuclease, sonicating the DNA, by heating the DNA, by irradiation of DNA using alpha, beta, gamma or other radioactive sources, by light, by chemical cleavage of DNA in the presence of metal ions, by radical cleavage and combinations thereof. Fragmenting of genomic DNA can also occur in vivo, for example and without limitation due to apoptosis, radiation and/or exposure to asbestos. According to the methods provided herein, a population of substrate molecules is not required to be of a uniform size. Thus, the methods of the disclosure are effective for use with a population of differently-sized substrate polynucleotide fragments.

The substrate molecule, as disclosed herein, is at least partially double stranded and comprises a 3' overhang (see FIG. 7*a*), a blunt end, a 3' recessed end, or a free 3' hydroxyl group. The length of an overhang or recessed end of a substrate polynucleotide can be varied. In various aspects, the length of an overhang or recessed end of a substrate molecule is 1, 2, 3, 4, 5, 6, 7, 8, 9, 10, 11, 12, 13, 14, 15, 16, 17, 18, 19, 20 or more nucleotides in length. In further embodiments, the length of an overhang or recessed end of a substrate molecule is at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19 or at least 20 nucleotides in length. In still further embodiments, the length of an overhang or recessed end of a substrate molecule is from about 1 to about 5, or from about 1 to about 10, or from about 1 to about 15, or from about 1 to about 20 nucleotides in length. A population of substrate molecules, in various aspects, includes those wherein more than one of the above-mentioned types of substrate molecules are present in a single reaction. The disclosure also contemplates that the substrate molecule is at least partially single stranded. Aspects of the disclosure in which the substrate molecule is single stranded involve the use of a single stranded ligase enzyme.

Some applications of the current invention involve attachment of adapter sequences not to original or native double stranded DNA substrate molecules but to a double stranded DNA produced by primer extension synthesis. One example of such an application is a DNA library produced by (a) attachment of an oligonucleotide comprising a primer-binding sequence to the 3' end of single-stranded or double-stranded DNA to enable primer extension, (b) extension of the primer annealed to the oligonucleotide, and (c) attachment of the 3' and 5' adapters to the double-stranded DNA ends produced by the primer-extension.

The length of either a double-stranded portion or a single-stranded portion of a substrate molecule is contemplated to be between about 3 and about $1\times10^6$ nucleotides. In some aspects, the length of the substrate molecule is between about 10 and about 3000 nucleotides, or between about 40 and about 2000 nucleotides, or between about 50 and about 1000 nucleotides, or between about 100 and about 500 nucleotides, or between about 1000 and about 5000 nucleotides, or between about 10,000 and about 50,000 nucleotides, or between about 100,000 and 1×106 nucleotides. In further aspects, the length of the substrate molecule is at least 3 and up to about 50, 100 or 1000 nucleotides; or at least 10 and up to about 50, 100 or 1000 nucleotides; or at least 100 and up to about 1000, 5000 or 10000 nucleotides; or at least 1000 and up to about 10000, 20000 and 50000; or at least 10000 and up to about 20000, 50000 and 100,000 nucleotides; or at least 20000 and up to about 100,000, 200,000 or 500,000 nucleotides; or at least 200,000 and up to about 500,000, 700,000 or 1,000,000 nucleotides. In various aspects, the length of the substrate molecule is about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 450, about 460, about 470, about 480, about 490, about 500, about 510, about 520, about 530, about 540, about 550, about 560, about 570, about 580, about 590, about 600, about 610, about 620, about 630, about 640, about 650, about 660, about 670, about 680, about 690, about 700, about 710, about 720, about 730, about 740, about 750, about 760, about 770, about 780, about 790, about 800, about 810, about 820, about 830, about 840, about 850, about 860, about 870, about 880, about 890, about 900, about 910, about 920, about 930, about 940, about 950, about 960, about 970, about 980, about 990, about 1000, about 1100, about 1200, about 1300, about 1400, about 1500, about 1600, about 1700, about 1800, about 1900, about 2000, about 2100, about 2200, about 2300, about 2400, about 2500, about 2600, about 2700, about 2800, about 2900, about 3000, about 3100, about 3200, about 3300, about 3400, about 3500, about 3600, about 3700, about 3800, about 3900, about 4000, about 4100, about 4200, about 4300, about 4400, about 4500, about 4600, about 4700, about 4800, about 4900, about 5000, 10,000, 15,000, 20,000, 50,000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000 or more nucleotides.

Adapter Molecule

Figure 3:
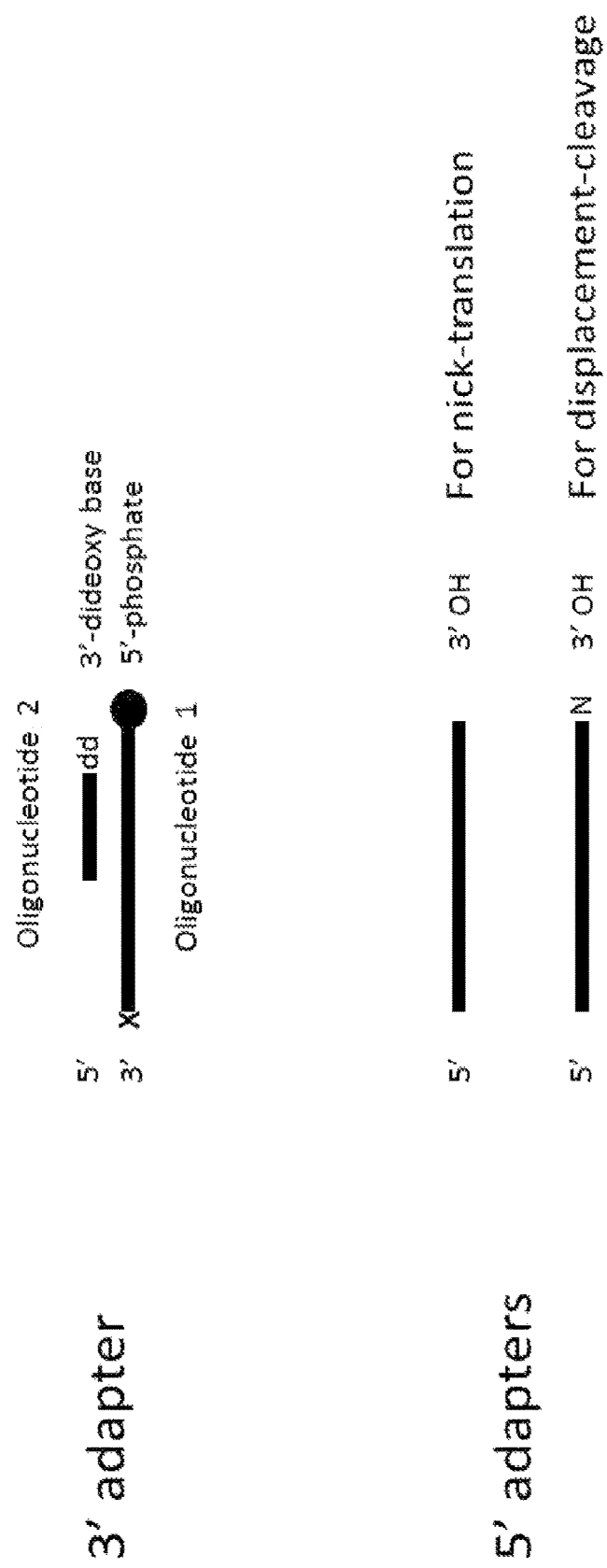

The disclosure contemplates the use of a 5' adapter and a 3' adapter (see FIG. 3). According to the disclosure, a 3' adapter is optionally double stranded, comprising an "oligonucleotide 1" and an "oligonucleotide 2." For such a double stranded substrate molecule, any length of oligonucleotide 1 and oligonucleotide 2 is contemplated as long as the two oligonucleotides are capable of annealing to each other under standard reaction conditions. Thus, the complementarity between oligonucleotide 1 and oligonucleotide 2 is such that they can anneal to each other. In various embodiments, the complementarity is from about 70%, 75%, 80%, 85%, 90%, 95% to about 100%, or from about 70%, 75%, 80%, 85%, 90%, to about 95%, or from about 70%, 75%, 80%, 85% to about 90%. In specific embodiments, the degree of complementarity between oligonucleotide 1 and oligonucleotide 2 is 70%, 75%, 80%, 85%, 90%, 95%, 99% or 100%. In further embodiments, oligonucleotide 2 comprises a nucleotide that is susceptible to degradation/removal such as an abasic nucleotide, a deoxyuracil nucleotide, a deoxyinosine nucleotide, or a ribonucleotide. In certain embodiments, oligonucleotide 1 and oligonucleotide 2 are different lengths and oligonucleotide 1 hybridizes anywhere along the length of oligonucleotide 2.

In further embodiments, the 5' adapter is single stranded. In embodiments wherein the 5' adapter hybridizes to oligonucleotide 1 of the 3' adapter, it is contemplated in further embodiments that such annealing results in either a nick, gap or in an overlapping base or bases between the 5' adapter and the substrate molecule (see FIG. 8). In various embodiments, the gap or the number of overlapping bases is 1, 2, 3, 4, 5, 6, 7, 8, 9, 10, 15, 20, 25, 30, 35, 40, 45, 50, 55, 60, 65, 70, 75, 80, 85, 90, 95 or 100 bases in length. In another embodiment wherein the 3' adapter is double stranded, following annealing of the 5' adapter to the 3' adapter, an enzyme is added to catalyze the "chewing forward" of the 5' adapter via nick translation to remove oligonucleotide 2. In some embodiments, the 5' adapter additionally comprises a random single, double or more N bases at its 3' terminus that are not complementary to oligonucleotide 1 and which can anneal to the first base(s) of the substrate molecule if its 5' bases are displaced. In other embodiments, the 5' adapter is a modified polynucleotide. Modified oligonucleotides contemplated for use are disclosed in United States Patent Application Publication Number 2011/0129832, incorporated by reference in its entirety. In a specific embodiment, the 5' adapter comprises a base modification selected from the group consisting of a locked nucleic acid (LNA) and a peptide nucleic acid (PNA). In certain embodiments, the 5'-adapter oligonucleotide is pre-annealed to the 3'-adapter (see FIG. 8).

The length of either a 5' adapter or a 3' adapter is contemplated to be between about 5 and about 200 nucleotides. In some aspects, the length of the 5' adapter or the 3' adapter is between about 5 and about 200 nucleotides, or between about 5 and about 150 nucleotides, or between about 5 and about 100 nucleotides, or between about 5 and about 50 nucleotides, or between about 5 and about 25 nucleotides, or between about 10 and about 200 nucleotides, or between about 10 and about 100 nucleotides. In further aspects, the length of the 5' adapter or the 3' adapter is at least 5 and up to about 50, 100 or 200 nucleotides; or at least 10 and up to about 50, 100 or 200 nucleotides; or at least 15 and up to about 50, 100, or 200 nucleotides; or at least 20 and up to about 50, 100 or 200 nucleotides; or at least 30 and up to about 50, 100 or 200 nucleotides; or at least 40 and up to about 50, 100 or 200 nucleotides. In various aspects, the length of the substrate molecule is about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, or more nucleotides in length.

Method—Steps

The first three incubations of the method are pre-ligation steps, and include (i) dephosphorylation, (ii) polishing and (iii) optional adenylation. The remaining 2 incubations of the method include (1) 3' adapter ligation, and (2) 5' adapter ligation which comprises (a) 5' adapter annealing (b) removal of the 5' base from the substrate molecule and (c) 5' adapter ligation (see FIGS. 4-6). In this aspect, the method has up to 3 pre-ligation steps and 2 ligation steps. In another aspect, the method has a single ligation step of the 5' adapter if the substrate molecule comprises a pre-existing 3' overhang, preferably serving as a 3' adapter (see FIG. 7a).

Pre-Ligation Steps (i) Dephosphorylation

Prior to adapter ligation, the DNA ends are optionally processed to improve efficiency of the adapter ligation reaction. DNA end processing in existing methods typically uses two enzymatic reactions: (a) incubation with a proofreading DNA polymerase(s) to polish DNA ends by removing the 3'-overhangs and filling-in the recessed 3' ends and (b) incubation with a polynucleotide kinase to add a phosphate group to the 5' termini. When processing DNA ends some methods also adenylate blunt-ended DNA at the 3' termini by incubation of polished DNA with a non-proofreading DNA polymerase. Adenylation helps to prevent DNA self-ligation and formation of chimeric products. It also minimizes formation of adapter-dimers due to the presence of dT at the 3' end of corresponding adapters. The current invention addresses these issues in a completely different way. Rather than adding a phosphate group to the 5' ends of the DNA fragments, the method of the invention implements an optional complete removal of the phosphate group from the 5' ends of the DNA fragments. Dephosphorylation of DNA ends is achieved by incubation of DNA fragments with an enzyme capable of removing a phosphate from a DNA terminus. Examples of enzymes useful in the methods of the disclosure to remove a 5' or a 3' phosphate include, but are not limited to, any phosphatase enzyme, such as calf intestinal alkaline phosphatase, bacterial alkaline phosphatase, shrimp alkaline phosphatase, Antarctic phosphatase, and placental alkaline phosphatase, each used according to standard conditions.

(ii) Polishing

After removal of the alkaline phosphatase or its inactivation by heat, DNA substrate molecules are optionally subjected to incubation with a proofreading DNA polymerase in the presence of dNTPs to create blunt ends. The reactions are performed according to standard conditions. Dephosphorylated and polished DNA fragments are good substrates for attachment of the 3' adapter but they are poor substrates for DNA fragment concatamer ligation and chimera formation. They are also poor substrates for ligation of a conventional adapter.

In some applications of the current invention, 5' end dephosphorylation by a phosphatase enzyme can be omitted but the addition of an enzyme such as T4 polynucleotide kinase to the DNA polishing mix is preferable in this case to assure removal of the phosphate group from the 3' termini prior to DNA polishing. Alternatively, the first two pre-ligation reactions described above, dephosphorylation and polishing, can be executed in any order and result in blunt-ended, double-stranded DNA lacking 5' phosphate groups at their termini.

(iii) Adenylation

The current invention also contemplates the use of adenylation of the 3' terminus of the blunt-end DNA fragments using DNA polymerases with non-template polymerase activity including but not limited to (exo-) Klenow fragment of DNA polymerase I, and Taq DNA polymerase. Both alkaline phosphatase treatment and adenylation reduce the propensity of DNA fragment self-ligation and formation of chimeric library molecules. In the case of including an adenylation step, the 3' adapter used in the subsequent step would require a single T overhang.

Ligation Steps (1) 3' Adapter Ligation, or, Generation of a Single-Stranded 3' Overhang on DNA Substrates The options are depicted in FIG. 7

Figure 7A:
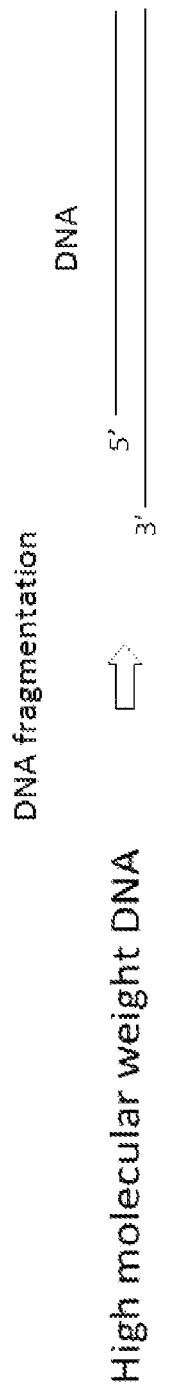

Option 1a: 3' Blocked Oligonucleotide 2 as Part of a Double Stranded 3' Adapter (FIG. 7a)

Figure 2:
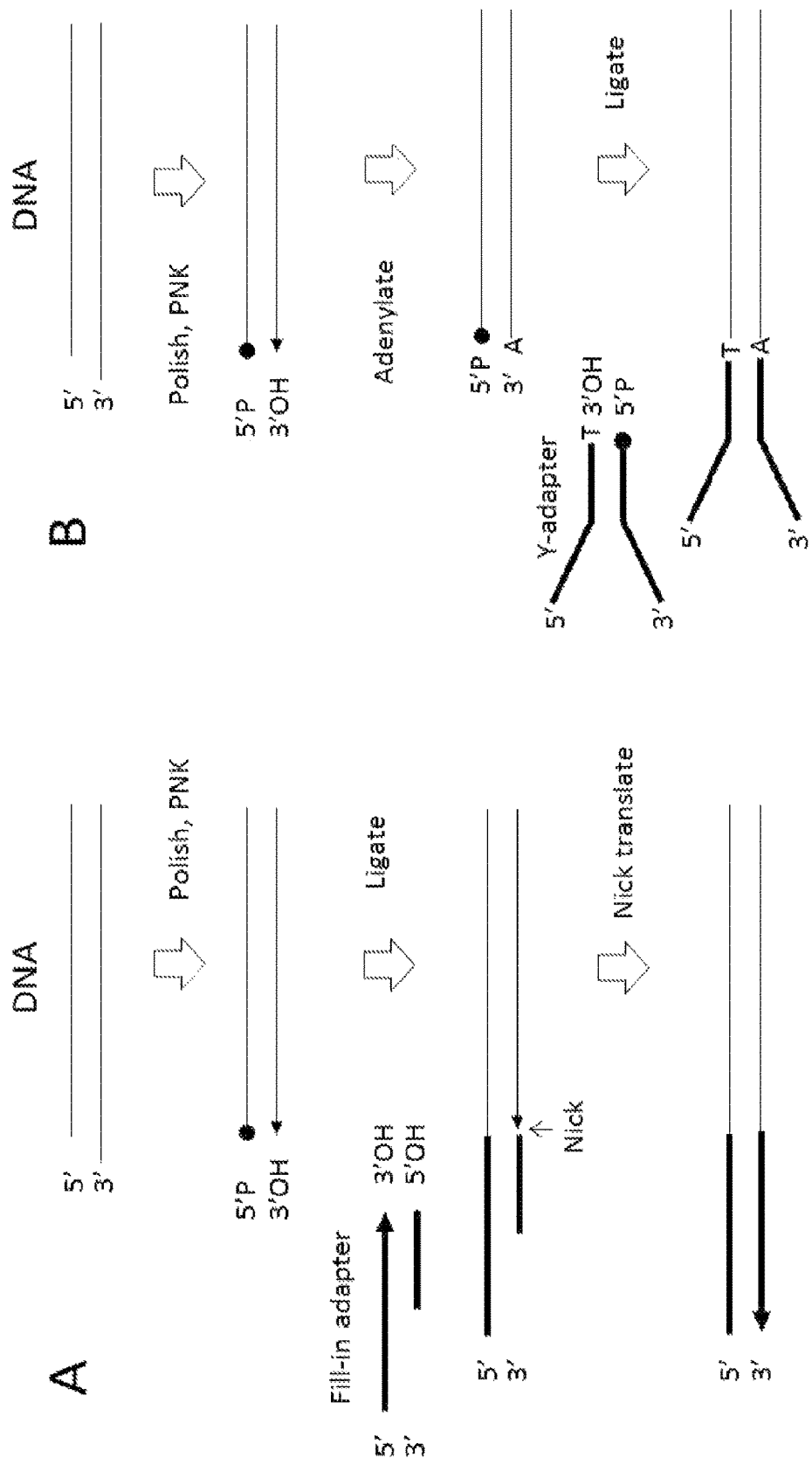

Existing NGS library preparation protocols rely on ligation between the 3'OH group of the adapter and the 5' phosphate group at the termini of the DNA fragments. For this reason, adapters used in conventional methods typically have one functional double-stranded end with a 3' hydroxyl group and optional 5' phosphate group (see FIGS. 1 and 2). In contrast, the current invention uses a ligation reaction between the 5' phosphate group of the 3' adapter and the 3' OH group of DNA fragments while leaving a nick between the 3' terminus of the 3' adapter and the 5' terminus of the DNA fragments (see FIG. 3). The 3' adapter has a functional double-stranded end with a 5'-phosphate group and in this option, a 3' nucleotide that is not competent for ligation (for example comprised of a sugar modified base analogs such as 2',3' dideoxy base or a 3'-deoxy base). The 3' adapter is formed by annealing two oligonucleotides: oligonucleotide 1 that has a phosphate group at the 5' end and a blocking group (such as a C3 spacer) at the 3' end, and oligonucleotide 2 that lacks a phosphate group at the 5' end and comprises a non-ligatable base at the 3' end. Oligonucleotide 2 additionally comprises modified bases and/or linkages that can be destroyed enzymatically, chemically or physically. In most applications, the end of the 3' adapter that is involved in ligation with the substrate molecule is a blunt end. In applications that involve adenylation of DNA fragments, the ligatable end of the 3' adapter has a 3' overhang containing a 2',3' dideoxythymidine or 3'-deoxythymidine base (or other modifications of the thymine base that block its ability to form a covalent linkage with the adjacent base). In other applications, the functional end of the 3' adapter could have either a 3' or 5' overhang containing multiple bases. During incubation with a DNA ligase, the 5' phosphate of the 3' adapter becomes ligated to the 3' terminus of the DNA substrate molecules while leaving a nick between the 3' terminus of the 3' adapter and the 5' terminus of the DNA substrate molecules. After the reaction is completed, ligated DNA is subjected to purification by spin-column or SPRI bead-based purification to remove excess adapters and other components of the ligation reaction.

Option 1b: 3' Hydroxyl Oligonucleotide 2 as Part of a Double Stranded 3' Adapter (FIG. 7a)

In an alternative method, a 3'-adapter that is lacking a blocked, unligatable base at the 3' terminus of oligonucleotide 2 can be used. Ligation of a non-blocked oligonucleotide 2 to the substrate molecule will still be prevented by the lack of 5' phosphate on the substrate molecule as a result of the dephosphorylation reaction. The advantage of using a non-blocked oligonucleotide 2 is that the 3' end of oligonucleotide 2 can be extended by a single base using a dideoxy nucleotide mix and a DNA polymerase capable nick-translation DNA synthesis. This enables an alternate method to perform 5' base excision from the substrate molecule, see subsequent steps described below. The disadvantage of using a non-blocked 3'-adapter is the creation of adapter-dimers during the ligation reaction which reduces adapter concentration and as a result, may decrease adapter ligation efficiency. Also for this option, oligonucleotide 2 additionally comprises modified bases and/or linkages that can be destroyed enzymatically, chemically or physically.

Option 2: Single Stranded 3' Adapter (FIG. 7a)

In the presence of a ligase (DNA or RNA) capable of covalently attaching a single stranded adapter to a double stranded (or single stranded) substrate molecule, oligonucleotide 2 can be omitted from the reaction.

Option 3: Homopolymer 3' Adapter (FIG. 7a)

In the presence of a template independent polymerase such as terminal deoxynucleotidyl transferase (TdT), poly (A) polymerase, poly(U) polymerase or DNA polymerases that lack 3'-exonuclease proofreading activity and comprising a nucleotide, a homopolymer or other tail can be incorporated on the 3' termini of the substrate molecules that can serve as a 3' adapter sequence.

Option 4: Controlled Tailing and Simultaneous 3' Adapter Ligation (FIG. 7a)

In the presence of a template independent polymerase such as TdT, nucleotides, and additionally comprising a ligase and an attenuator-adapter molecule, a synthetic tail and defined 3' adapter sequence can be incorporated on the 3' termini of the substrate molecules. See International patent application number PCT/US13/31104, filed Mar. 13, 2013, incorporated by reference in its entirety.

Figure 7B:
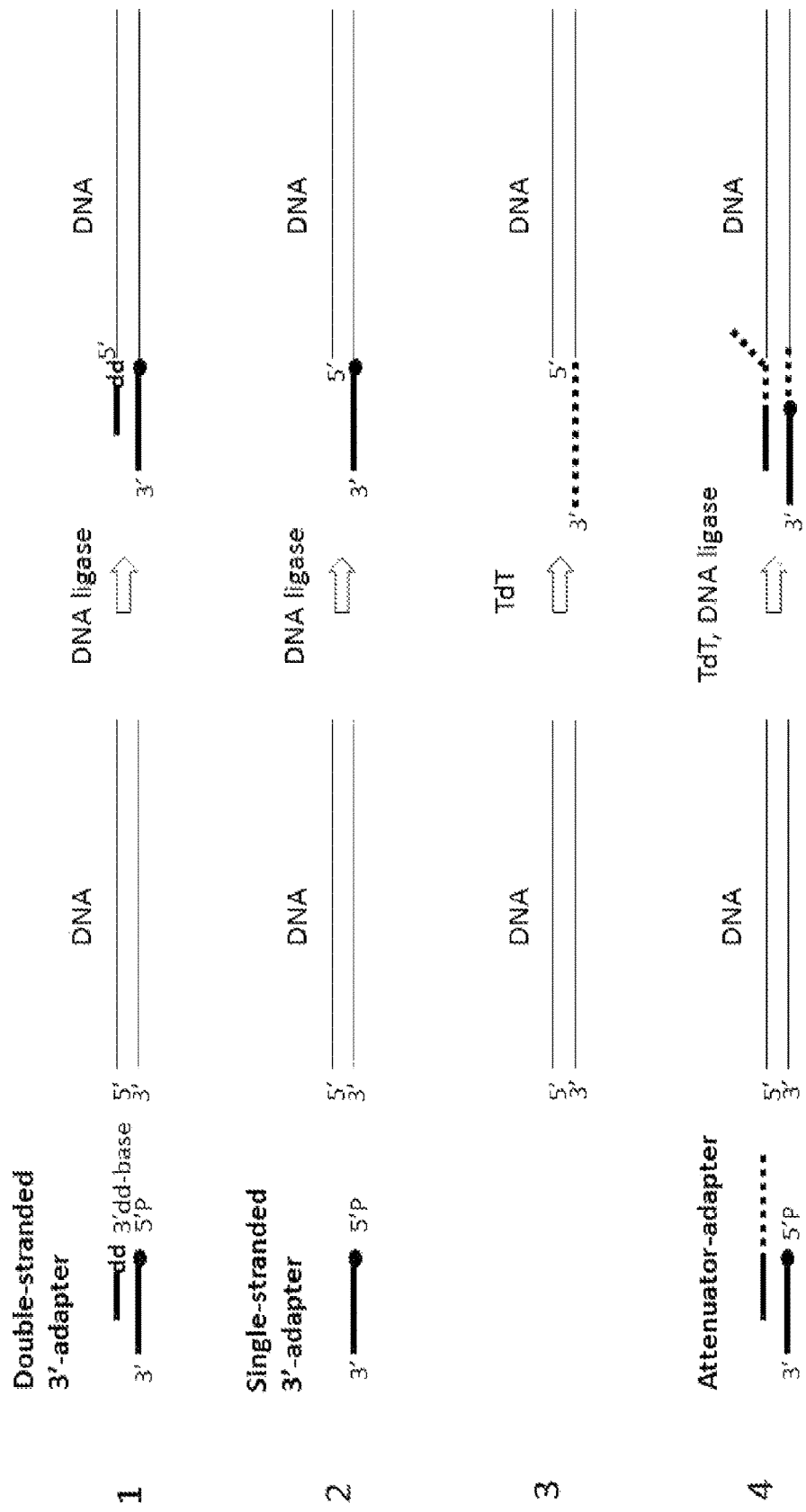

Option 5: Omit 3' Adapter Ligation Step (FIG. 7b)

In the case of substrate molecules that comprise a pre-existing 3' overhang that is naturally occurring or resulting from a previous enzymatic or other treatment, either as a defined or random sequence, a separate 3' adapter ligation step is not required and can be omitted, wherein the pre-existing 3' overhang can serve as the 3' adapter.

In an alternative embodiment, a phosphatase enzyme with Zinc and other reaction components can be added to the 3' adapter ligation reaction at its completion. Performing a phosphatase reaction following 3' adapter ligation is a means of rendering any non-ligated 3' adapter molecules incapable of subsequent ligation, which prevents adapter dimers from forming in subsequent steps when the 5' adapter is present.

(2) 5' Adapter Ligation, which is Comprised of Three Steps that Occur in a Single Incubation (I) Annealing of the 5' Adapter In the case of single stranded 3' adapter ligation (option 2), homopolymer addition (option 3) or use of pre-existing 3' overhang as 3' adapter (option 5), annealing of the 5' adapter can be performed directly without other consideration as there is no oligonucleotide 2 to degrade or displace.

When ligation of a double-stranded 3'-adapter is used to create a single-stranded 3' overhang at the ends of double-stranded DNA (options 1a, 1b and 4 above), the 5'-adapter can be annealed to the 3'-adapter using any of five different options, each of which is discussed below and depicted in FIG. 8:

i) following degradation of oligonucleotide 2 that was annealed to the 3' adapter ii) by competitive displacement of oligonucleotide 2 that was annealed to the 3'-adapter iii) by annealing the 5' adapter further 3' on oligonucleotide 1 relative to the annealing site of oligonucleotide 2, followed by nick-translation and degradation of oligonucleotide 2 iv) by having the 5' adapter pre-annealed to the 3' region of oligonucleotide 1 of the 3' adapter, followed by nick-translation and degradation of oligonucleotide 2 v) by having the 5' adapter with a 3' blocking group pre-annealed to the 5' region of oligonucleotide 1 of the 3' adapter (instead of oligonucleotide 2), followed by enzymatic excision of the 3' blocking group Option i:

Oligonucleotide 2 of the 3' adapter additionally comprises modified bases and/or linkages that can be destroyed enzymatically, chemically or physically. Modifications include but are not limited to dU-bases, deoxyinosine and RNA bases. Annealing of the single-stranded 5' adapter to the 5' portion of oligonucleotide 1 of the 3' adapter occurs as result of partial degradation of the 3' adapter, specifically, of oligonucleotide 2. In some embodiments, degradation of oligonucleotide 2 is achieved enzymatically, more specifically, by using uracil-DNA glycosylase (UDG), or a combination of UDG and apurinic/apyrimidinic endonuclease if the second oligonucleotide contains deoxyuracil bases, or by endonuclease V if the second oligonucleotide contains deoxyinosine bases. Degradation of oligonucleotide 2 can also be performed by incubation with RNase H1 or RNase H2 if the second oligonucleotide contains RNA bases. In some applications, degradation of the second oligonucleotide can be done chemically or physically, for example, by light.

Option ii:

In some applications, annealing of the 5' adapter to oligonucleotide 1 of the 3'adapter occurs without degradation of oligonucleotide 2. In this case, replacement of oligonucleotide 2 with the single-stranded 5' adapter can be facilitated by higher affinity of the 5' adapter over that of oligonucleotide 2 either due to increased complementarity between oligonucleotide 1 and the 5' adapter sequence or due to base modifications within the 5' adapter that increase its melting temperature (for example, LNA bases). Depending on the design of the 5' adapter, annealing to oligonucleotide 1 of the 3' adapter could either result in a nick or gap between the 3' end of the 5' adapter and the 5' end of the DNA substrate molecule, or in overlap of the 3' and 5' bases of the 5' adapter and DNA substrate molecule, correspondingly.

Option iii:

In this case, neither degradable modifications or competitive displacement of oligonucleotide 2 is used. Instead, the 5' adapter replaces oligonucleotide 2 by annealing to the 3' adapter further 3' on oligonucleotide 1 relative to the annealing site of oligonucleotide 2, followed by limited nick-translation "chewing forward" which results in degradation or partial degradation of oligonucleotide 2.

Options iv and v:

In these cases, the 5' adapter constitutes a part of the 3' adapter and it is present during ligation of the 3' adapter to the DNA substrate. In option iv, the 5' adapter is pre-annealed to the 3' adapter further 3' on oligonucleotide 1 relative to the annealing site of oligonucleotide 2 (similar to option iii). In option v, the 5' adapter has a blocking group at the 3' end and it is pre-annealed the 3' adapter instead of oligonucleotide 2. After ligation of the 3' adapter, the blocking group at the 3' end of the 5' adapter is removed enzymatically to allow its extension by a DNA polymerase.

(II) 5'-Base Removal from the Substrate Molecule Resulting in Exposure of a 5' Phosphate In this step, creation of a ligation-compatible 5' terminal phosphate group on the substrate molecule is achieved by removal of the damaged 5' terminal base of the DNA substrate molecules either by nick-translation of the 5' adapter oligonucleotide using a DNA polymerase and nucleotides (option i), by a displacement-cleavage reaction using the 5' adapter and a 5'-flap endonuclease in the absence of nucleotides (option ii), or by single dideoxy base extension from oligonucleotide 2 followed by displacement-cleavage using a 5'-flap endonuclease in the absence of nucleotides (option iii). For the third option, 5' base excision of the substrate molecule occurs prior to 5' adapter annealing, because it is alternately performed using the annealed oligonucleotide 2 instead of the 5' adapter, but is included in this section to simplify description of the method (see FIG. 9).

Figure 4:
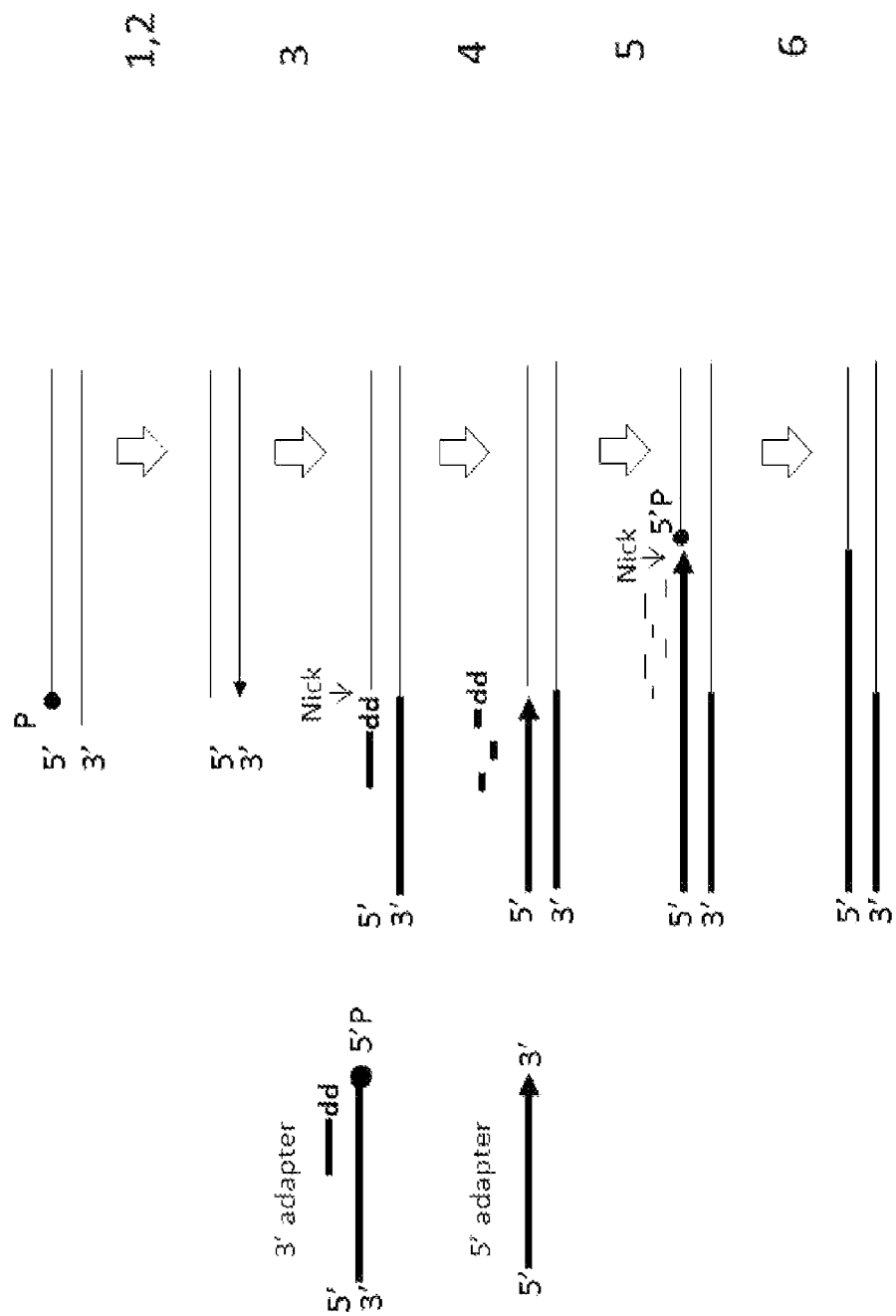
Figure 6A:
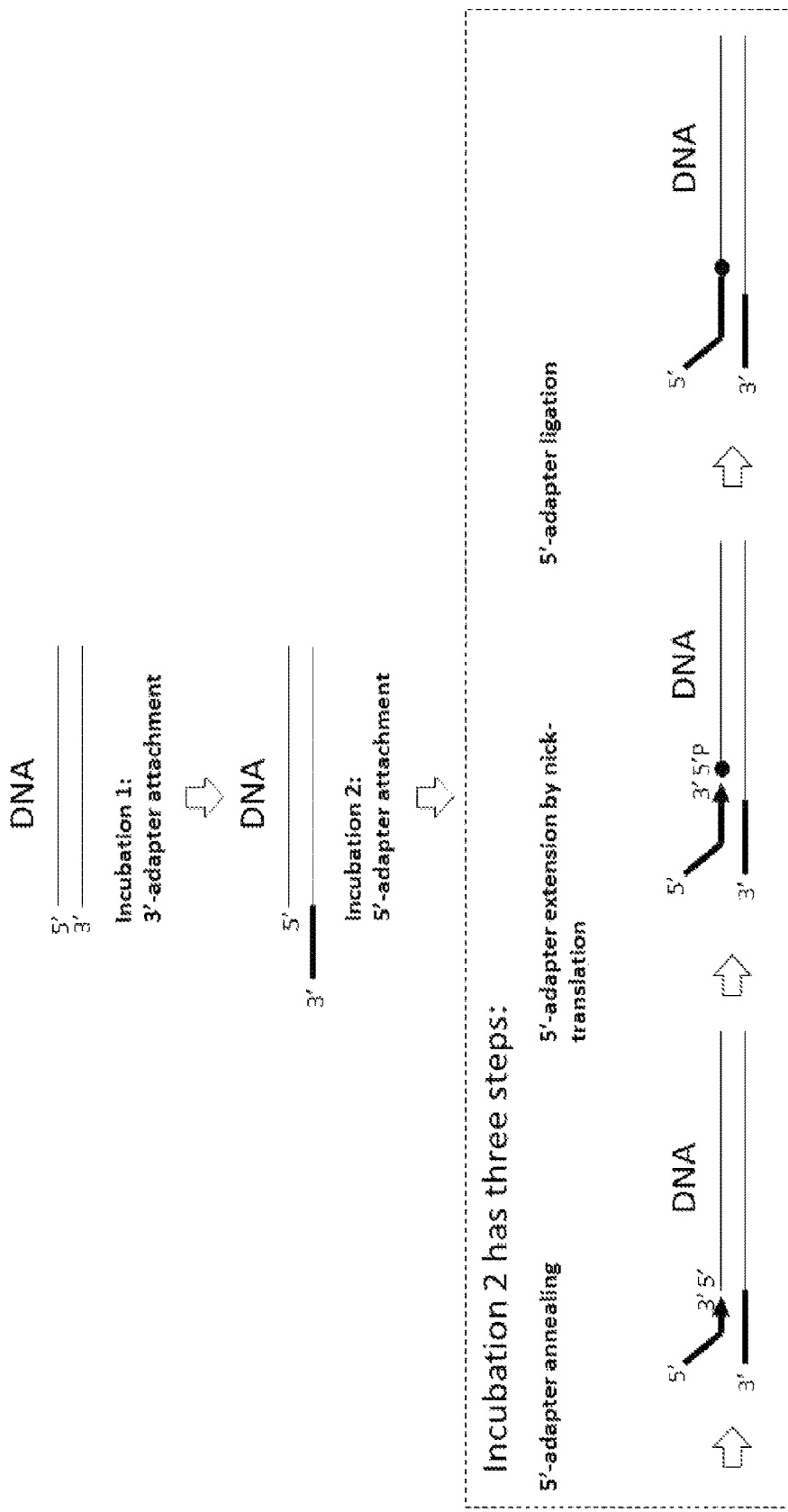

Option i:

Nick-translation DNA synthesis is initiated at the nick or gap between the 3' end of the 5' adapter oligonucleotide and the 5' end of the DNA substrate molecules and stops when the ligation reaction seals the nick (see FIGS. 4 and 6a). The nick-translation reaction can be performed by but is not limited to DNA polymerases capable of nick-translation DNA synthesis such as DNA polymerase I (holoenzyme), Taq DNA polymerase, Tth DNA polymerase, and Bst DNA polymerase (holoenzyme). Additional enzymes contemplated for use include, without limitation, DNA polymerases with 5'-3' exonuclease activity, 5' flap endonuclease, and a combination of a strand displacement polymerase and a 5' flap endonuclease.

The reaction conditions contemplated for this step include those where (i) both a polymerase with endogenous 5' exonuclease activity and a ligase are active; (ii) a strand displacement polymerase and flap endonuclease polymerase and ligase are active; (iii) a flap endonuclease and a ligase are active, (iv) simultaneous activity of both a thermostable enzyme and a thermolabile enzyme occur; or (v) where activity of only thermostable or only thermolabile enzymes can occur. In some embodiments, conditions (i) and (ii) are each performed with dNTPs for nick translation. In a specific embodiment, Taq polymerase and *E. coli* ligase are used at a reaction temperature of 40° C. In various embodiments, however, a range of reaction temperatures from 10° C. to 75° C. are contemplated.

The nick-translation reaction results in removal of one, two or more bases from the 5' end of the DNA substrate molecules prior to the ligation reaction which occurs between the 5' adapter extension product and the DNA substrate molecule. Nick-translation synthesis can occur in the presence of all four nucleotides dGTP, dCTP, dTTP and dATP or their restricted combinations. Restricted combinations include but are not limited to three-nucleotide combinations such as dGTP, dCTP and dATP, or dGTP, dCTP and dTTP, or dGTP, dATP and dTTP, or dCTP, dATP and dTTP, two-nucleotide combination such as dGTP and dCTP, or dGTP and dATP, or dGTP and dTTP, or dCTP and dATP, or dCTP and dTTP, or dATP and dTTP or just one nucleotide such as dGTP, or dCTP, or dATP, or dTTP.

Figure 5:
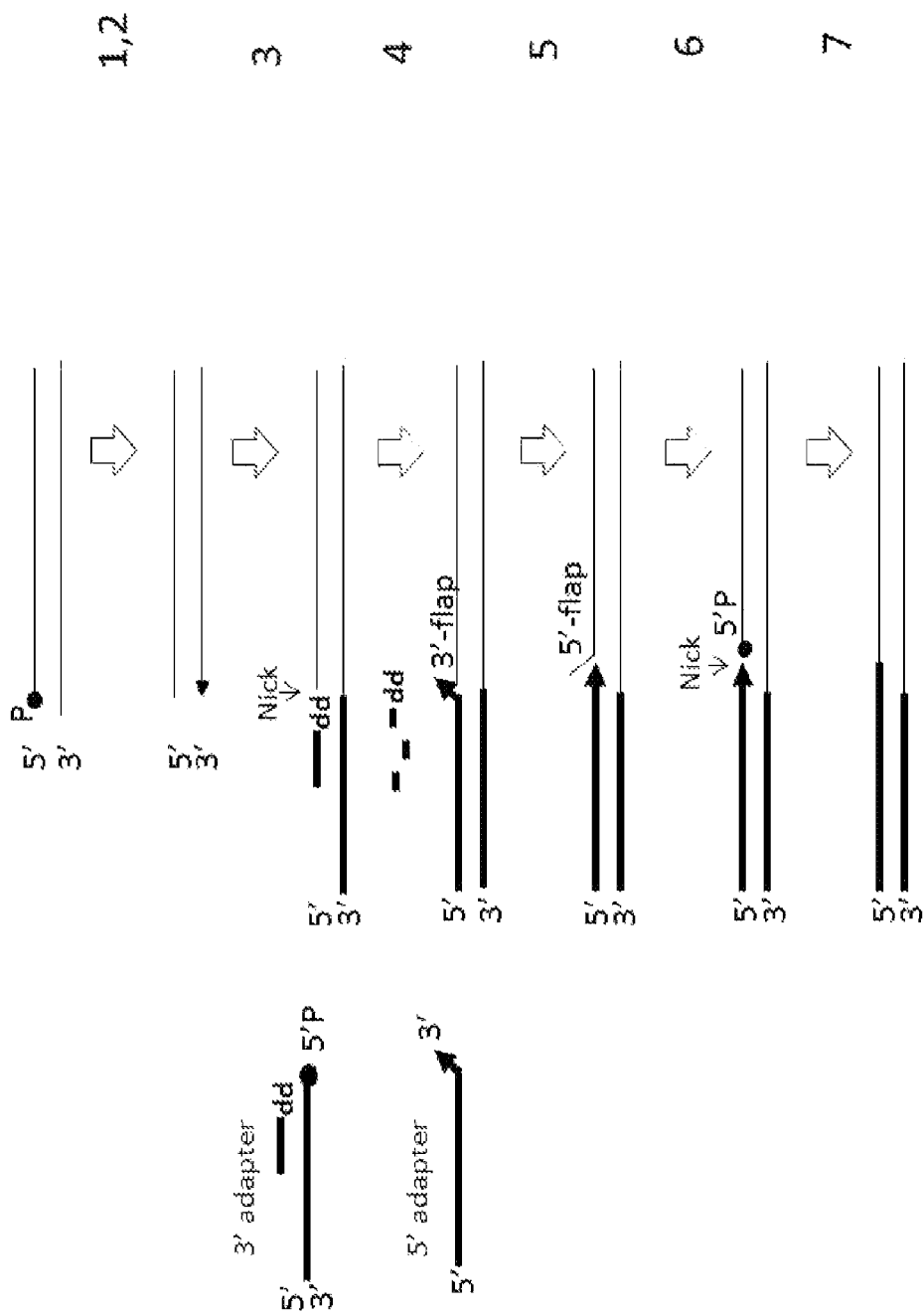
Figure 6B:
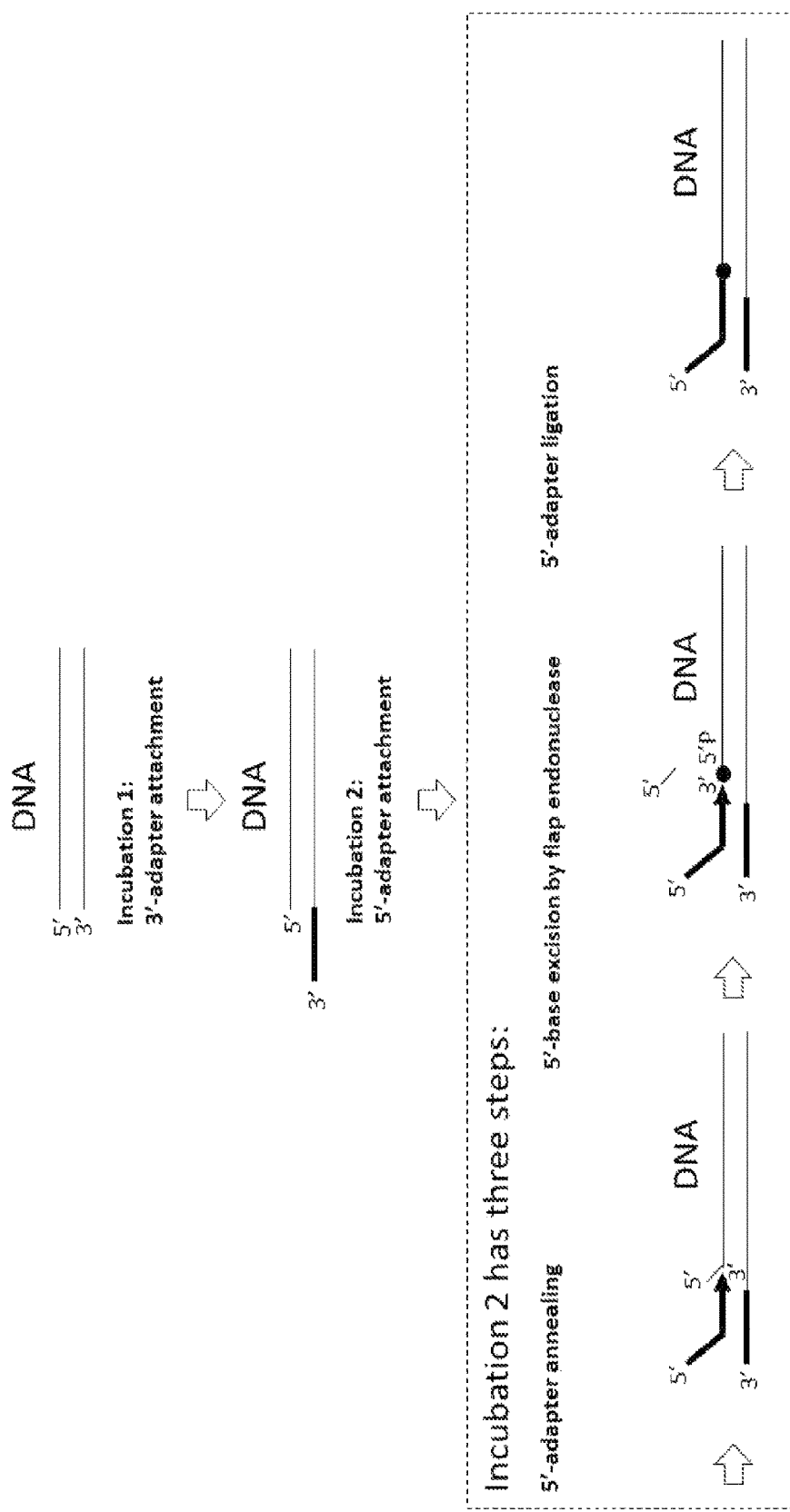

Option ii:

The displacement-cleavage reaction does not require dNTPs but requires that the 5' adapter sequence comprises one, two or more random bases at the 3' terminus to create an overlap with the substrate molecule, and which comprises a plurality of 5' adapters in the reaction (see FIGS. 5 and 6b). The displacement-cleavage reaction is initiated by annealing of the 5' adapters, displacement of the 5' DNA bases of the DNA substrate molecule that overlap with the 3' bases of the 5' adapters, and cleavage of the displaced bases by a 5'-flap endonuclease. In some embodiments, the 5' adapter has one random base dN at the 3' end. In this case the overlap involves one base and only a single 5' base would be removed from the 5' end of DNA substrate molecules and replaced with a similar base from the 5' adapter sequence. Efficiency of the displacement-cleavage reaction is increased by cycling the temperature of the reaction between 40° C. and 65° C. to allow 5' adapters to dissociate and re-anneal if its terminal 3' base is mismatched to the 5' base of the DNA substrate molecule.

Option iii:

An alternative embodiment to the 5' adapter participating in the 5' base excision of the substrate molecules is to instead, in a previous step, have oligonucleotide 2 of the 3' adapter participate in the 5' base excision of the substrate molecules (see FIG. 9).

In one approach (FIGS. 9a and c), oligonucleotide 2 of the 3' adapter comprises an extendable 3' terminus and in the presence of a dideoxy nucleotide mixture and a polymerase under appropriate conditions, a single dideoxy base addition occurs which leads to a single base overlap with the 5' terminus of the substrate molecules, which induces single base displacement-cleavage by an appropriate flap endonuclease or polymerase that possesses 5' flap endonuclease activity. Subsequently, a 5' adapter with a random dN base at its 3' terminus is used (FIG. 9a), where a nick is formed after binding to the 3'-adapter attached to the end of double stranded DNA. The nick can be sealed by a DNA ligase resulting in covalent attachment of the 5'adapter to the 5' terminus of the DNA substrate molecule.

Alternatively, a 5'adapter oligonucleotide that lacks a random dN base at its 3' terminus can be used (FIG. 9c), which forms a single base gap after binding to the 3'-adapter attached to the end of double stranded DNA substrate molecule. The gap can be filled in by a DNA polymerase lacking strand-displacement activity (for example T7 or T4 DNA polymerase) to create a nick that can be in turn sealed by a DNA ligase resulting in covalent attachment of the 5'adapter to the 5' end of DNA substrate molecule.

In another alternative (see FIGS. 9b and d), oligonucleotide 2 that comprises a blocked 3' terminus is partially degraded or displaced by a primer oligonucleotide that becomes extended with a single dideoxy-base by a DNA polymerase with 5' flap endonuclease activity resulting in excision of a single base from the 5' terminus of DNA. The primer oligonucleotide, in turn, becomes degraded or displaced by the 5' adapter with a random dN base at its 3' terminus to create a nick that can be sealed by a DNA ligase.

(III) Ligation of the 5' Adapter

Covalent attachment of the 5' adapter to the substrate molecule involves ligation between the 5' adapter or its extension product and the exposed 5' phosphate of the substrate molecules. When excision of the 5' base(s) of DNA substrate molecules is achieved by a nick-translation reaction, the ligation reaction seals the nick between the polymerase-extended 5' adapter and the excised 5' end of the DNA substrate molecule. When excision of the 5' base of DNA substrate molecules is achieved through the displacement-cleavage reaction, the ligation occurs between the original 5' adapter oligonucleotide and the excised 5' end of the DNA substrate molecule. The standard conditions with respect to the ligation reaction in this step comprise, in various embodiments, use of any DNA ligase that is capable of sealing nicks or gaps in DNA. In one embodiment, the ligase is E. coli DNA ligase and the reaction occurs in the temperature interval between 10° C. and 50° C. In some embodiments, the ligase is a thermostable DNA ligase such as Taq DNA ligase, or AmplLigase, and the reaction occurs in the temperature interval between 30° C. and 75° C.

In various aspects of the current invention, the three steps (I), (II) and (III) of the 5' adapter ligation step are performed simultaneously in a single incubation by mixing and incubating the 3'-adapted substrate DNA with (i) an optional degradation endonuclease (e.g., UDG, endonuclease V, RNase H, or their combination); (ii) a nick-translation DNA polymerase or a 5'-flap endonuclease; and (iii) a DNA ligase (see FIG. 6). The incubation is carried out at a constant temperature or using temperature cycling conditions in the interval 10° C.-75° C. In other applications, 3' adapter partial degradation is performed separately from the downstream reactions.

Construction of NGS Libraries

Synthesis of an Illumina NGS library can be performed using the disclosed methods. As shown in FIG. 10, an Illumina library can be constructed using either the nick translation ligation method (left side) or the displacement cleavage ligation method (right side). The order of attachment of the two Illumina adapters is flexible, where in FIG. 10a, Illumina adapter P7 is a 3' adapter and Illumina adapter P5 is a 5' adapter, whereas in FIG. 10b, Illumina adapter P5 is a 3' adapter and Illumina adapter P7 is a 5' adapter. The libraries depicted in FIG. 10 can be constructed PCR-free or can be PCR amplified, depending on the amount of input substrate DNA. Alternatively, synthesis of Illumina NGS libraries can be performed using the disclosed methods where PCR amplification is required, because the method uses truncated adapter sequences (see FIG. 11). In this case, either P5 or P7 is introduced as a truncated adapter (only P7 shown), and following amplification using a PCR primer that introduces the full-length adapter sequence as well as comprises degradable bases at its 5' terminus, following degradation of the 5' portions of the resulting amplicons, either P7 or P5 can be introduced by annealing and ligation. If alternatively a truncated degradable primer is used for the PCR amplification, a bridge-ligation of the remainder of the adapter can be performed to complete the full-length sequence.

Figure 12A:
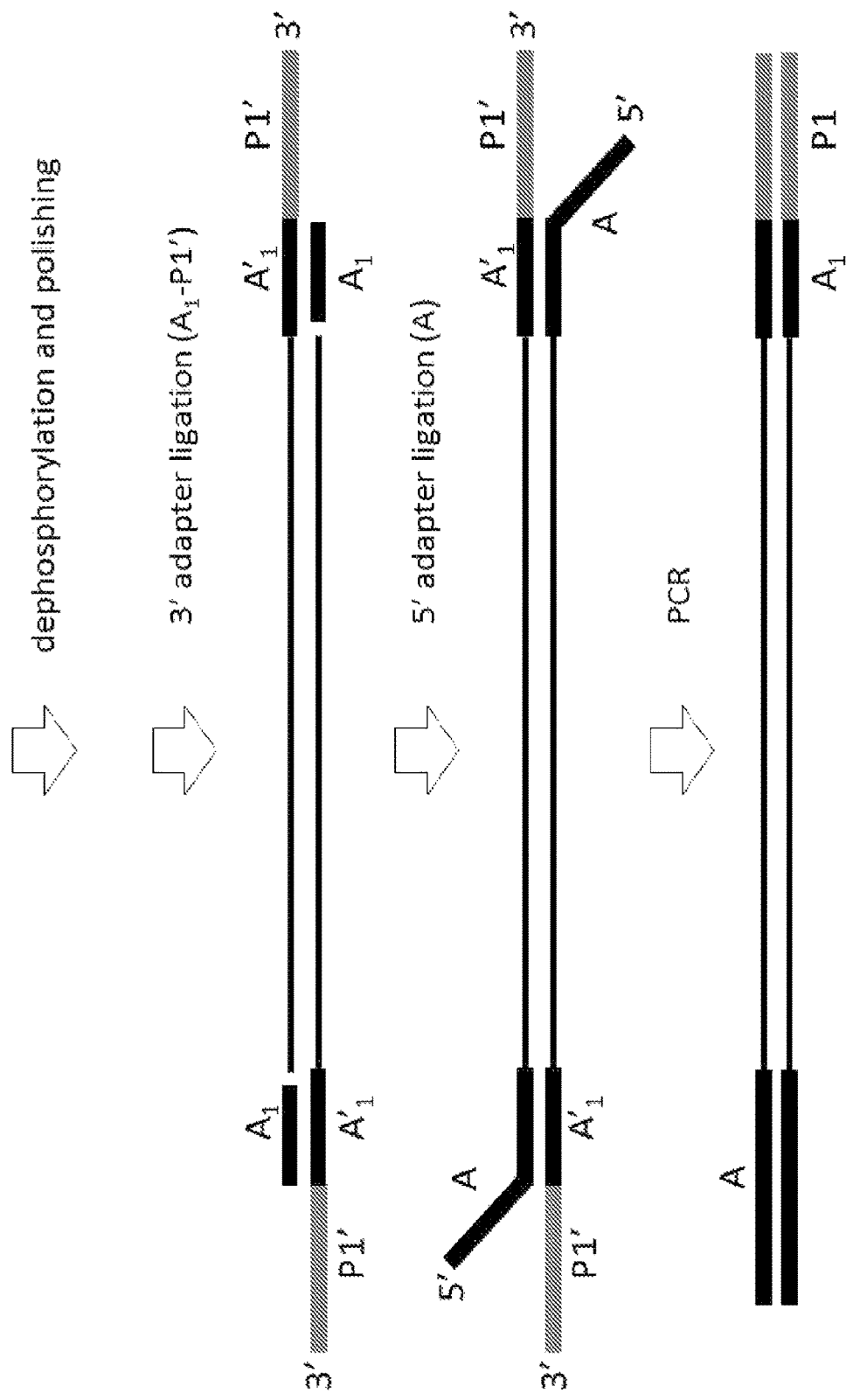
Figure 12B:
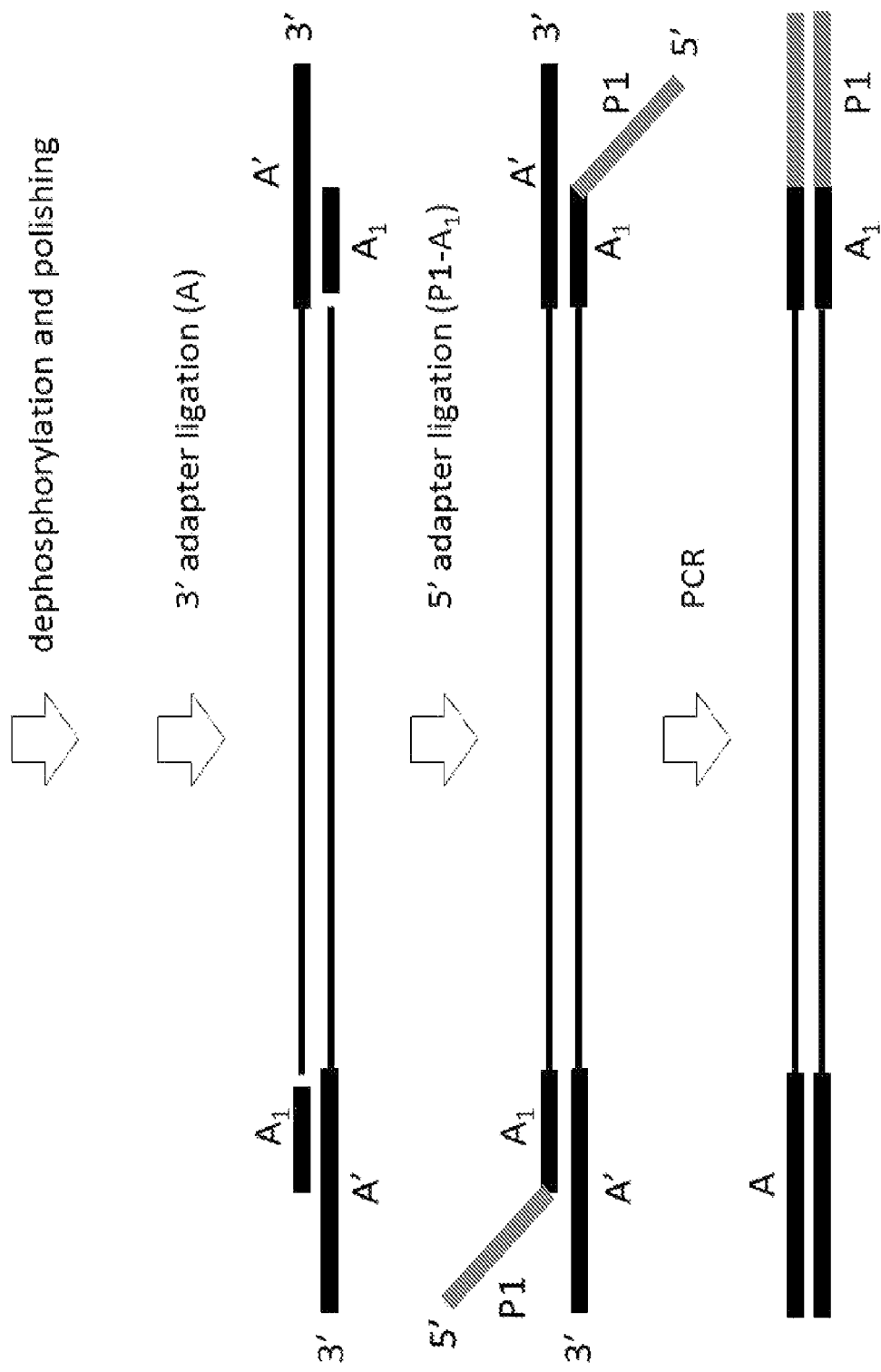

The disclosed methods can be used to construct NGS libraries for a variety of sequencing platforms, and another example is presented in FIGS. 12 and 13 where Ion Torrent library construction is depicted. As shown in FIG. 12, by introducing a partial duplication of the A adapter sequence on the P1 adapter at the insert junction site, subsequent annealing of a 5' adapter after 3' adapter ligation can occur. The order of ligation is flexible, where adapter P1 with a partial duplication of adapter A can be introduced as a 3' adapter followed by ligation of adapter A as a 5' adapter using either nick translation or displacement cleavage (FIG. 12a). Alternatively, adapter A can be introduced as a 3' adapter and adapter P1 with a partial duplication of adapter A can be a 5' adapter (FIG. 12b). Since Ion Torrent sequencing is performed as a single read from the A adapter, due to the length of the partial duplication of adapter A on the P1 adapter, it will not interfere with sequencing primer annealing or other adapter functions.

Alternatively in FIG. 13, combinatorial barcoding can be introduced to Ion Torrent libraries using the disclosed method. During the 3' adapter ligation step, the first portion of the dual combinatorial barcode is introduced, adjacent to a linker region L that is common to all 20 barcodes. After degradation of the 3' blocked strand that does not ligate to the DNA substrate, a 5' adapter anneals to the common linker region L which incorporates the second portion of the dual barcode 5' adjacent to the linker region L. Following nick translation ligation, the resulting library can be amplified with standard Ion Torrent PCR primers, and when library molecules are sequenced from the A adapter side, the sample identification of each Ion sphere will be read at the beginning of the read, where 96 possible combinations can be achieved.

Applications for Target Selected NGS Libraries

The disclosed methods can be used to construct NGS libraries where specific targets can be selected and enriched, as a way to reduce complexity and sequencing requirements relative to whole genome sequencing. An example of such an application would be attachment of the 3' adapter and 5' adapter to randomly fragmented, denatured and primer-extended DNA substrates, where the primer or plurality of primers anneal to known targeted DNA regions. In this case, only the targeted loci would comprise a double stranded terminus, where non-selected loci would remain single stranded and adapter ligation would not occur on their termini.

In other applications, the 5' adapter of the current invention can be used to select and enrich a small fraction of DNA fragments with known terminal sequences. Pre-selected DNA sequences could contain one, two, three or more terminal DNA bases. To achieve such selection the 5' adapter sequence should contain selected invasion bases or base combinations at the 3' end. As a result, only DNA fragments with selected terminal sequences will be ligated to the 5' adapter and amplified. As shown in FIG. 14, use of 5' adapters with 3' termini complementary to the terminal sequences of selected restriction fragments can be used to select restriction fragment targets from a plurality of restriction fragments. In another embodiment, use of 5' adapters with 3' termini comprising CpG dinucleotides would enrich for fragments originating from CpG islands.

Figure 15A:
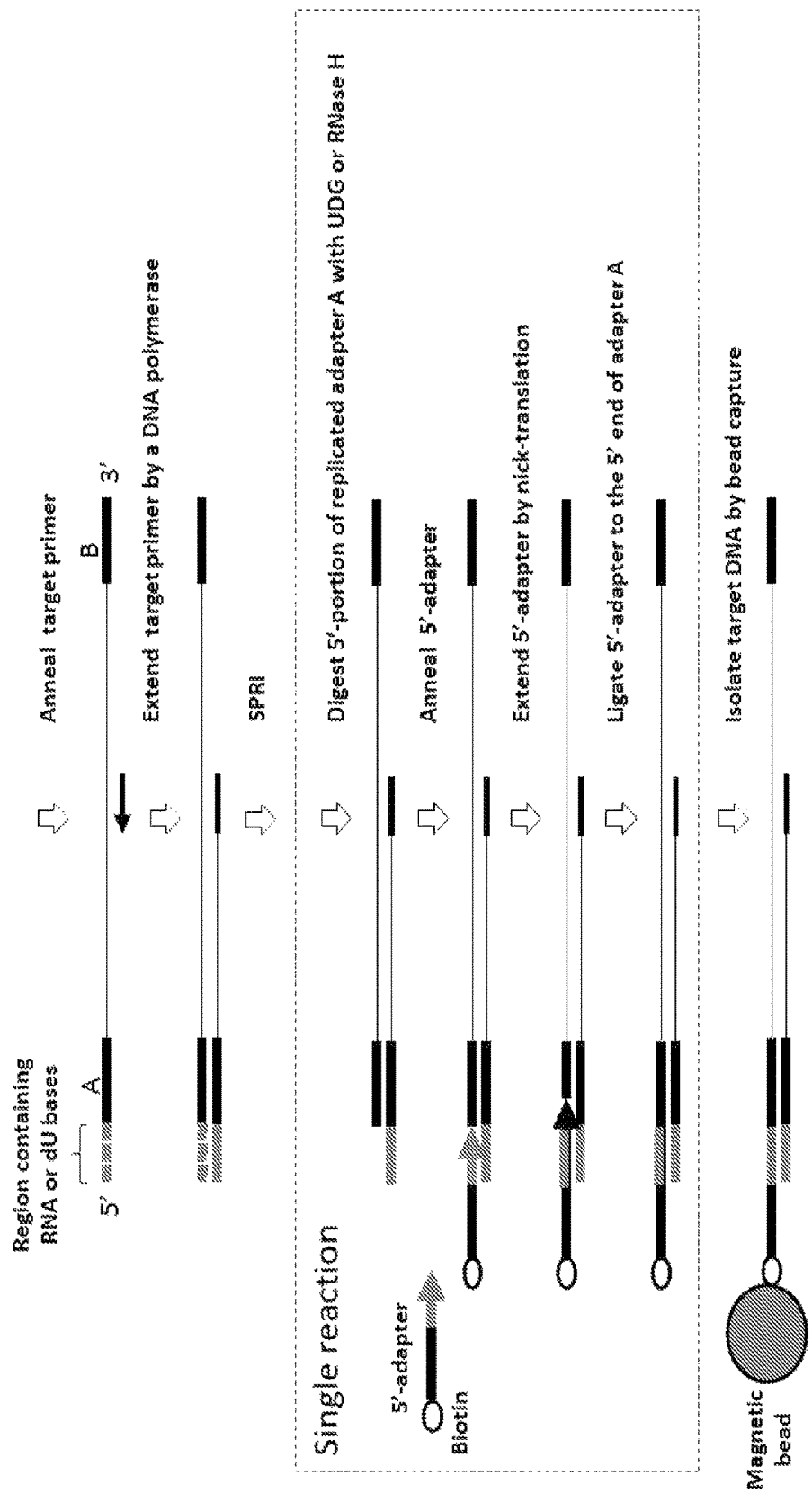
Figure 15B:
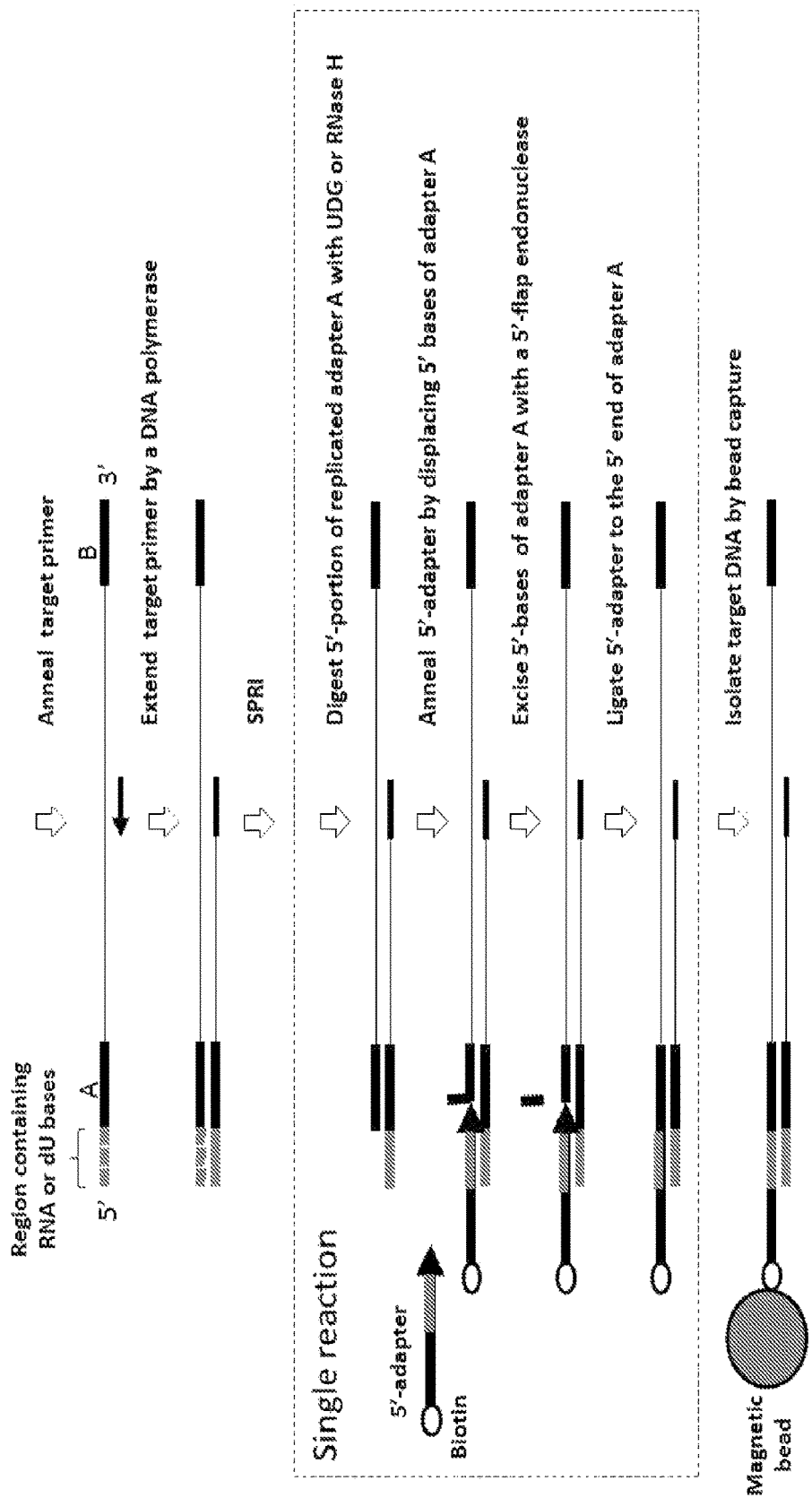

Alternatively, target selection can be performed following library construction using the methods disclosed within (see FIG. 15). If such a library is constructed where one adapter comprises degradable bases at its 5' terminus, following target-specific primer extension and partial digestion of the degradable portion of the adapter, a biotinylated 5' adapter can be annealed to the resulting 3' overhang and using either nick translation ligation (FIG. 15a) or displacement cleavage ligation (FIG. 15b), the biotinylated 5' adapter is covalently attached to only targeted DNA substrates and can be subsequently captured using streptavidin magnetic beads and then PCR amplified to generate sufficient material for sequencing.

Alternative Adapter Designs and Applications

Several alternative adapter designs and ligation methods using the disclosed methods are also presented. In FIG. 16, a library is constructed using a single adapter sequence instead of a pair of adapter sequences. In this example, the same steps are used for substrate processing prior to ligation and both 3' adapter ligation and either nick translation ligation or displacement cleavage ligation of the 5' adapter, and the resulting library can be PCR amplified using a single primer.

In FIG. 17, a method for ligation of single oligonucleotide hairpin adapters is presented, wherein the 5' terminus of the hairpin adapter is used to perform 3' adapter ligation to the substrate molecule, and following degradation of the blocked 3' terminus of the hairpin adapter, the truncated 3' terminus of the hairpin adapter is used for nick translation ligation to the exposed 5' phosphate of the substrate molecule.

Sometimes it is useful to generate circular DNA libraries, such as an intermediate structure for the construction of mate-pair NGS libraries. As shown in FIG. 18, such a library can be constructed using methods of the disclosure. In the first step, 3' adapter ligation is performed using mutually complementary adapters X and X'. Following degradation of the non-ligated strand, non-covalent DNA circularization can occur by means of complementarity of the 3' overhangs X and X' on each substrate molecule. To favor unimolecular annealing and reduce concatamer formation, this annealing reaction is performed at an appropriately low DNA concentration. Following 3' overhang annealing, nick translation ligation can be performed.

Additional Methods

In additional aspects, it is contemplated that the methods and compositions disclosed herein will improve current technologies through the use of a nick-translation mediated ligation step. Non-limiting examples of such improvements are described below.

The disclosure contemplates, in some aspects, a variation on the use of a 5' adapter (see FIGS. 30-32). In such aspects, oligonucleotide 2 of the 3' adaptor functions as the 5' adapter.

The disclosure also contemplates, in various aspects, a variation on the use of a 5' adapter and a 3' adapter (see FIG. 33 and FIG. 34). In such aspects, the term "5' adapter" is used interchangeably with "polynucleotide 1" and the term "3' adapter" is used interchangeably with "polynucleotide 2." In some aspects, a 5' adapter is optionally double stranded, comprising an "oligonucleotide a" and an "oligonucleotide b." For such a double stranded substrate molecule, any length of oligonucleotide a and oligonucleotide b is contemplated as long as the two oligonucleotides are capable of annealing to each other under standard reaction conditions. Thus, the complementarity between oligonucleotide a and oligonucleotide b is such that they can anneal to each other. In various embodiments, the complementarity is from about 70%, 75%, 80%, 85%, 90%, 95% to about 100%, or from about 70%, 75%, 80%, 85%, 90%, to about 95%, or from about 70%, 75%, 80%, 85% to about 90%. In specific embodiments, the degree of complementarity between oligonucleotide a and oligonucleotide b is 70%, 75%, 80%, 85%, 90%, 95%, 99% or 100%. In further embodiments, oligonucleotide a comprises a nucleotide that is susceptible to degradation/removal such as an abasic nucleotide, a deoxyuracil nucleotide, a deoxyinosine nucleotide, or a ribonucleotide. In certain embodiments, oligonucleotide a and oligonucleotide b are different lengths and oligonucleotide a hybridizes anywhere along the length of oligonucleotide b.

In further embodiments, the 3' adapter is single stranded. In embodiments wherein the 3' adapter hybridizes to oligonucleotide b of the 5' adapter, it is contemplated in further embodiments that such annealing results in either a nick, gap or overlap between the 3' adapter and the substrate molecule (see FIG. 33). In various embodiments, the gap is 1, 2, 3, 4, 5, 6, 7, 8, 9, 10, 15, 20, 25, 30, 35, 40, 45, 50, 55, 60, 65, 70, 75, 80, 85, 90, 95 or 100 bases in length. In another embodiment wherein the 5' adapter is double stranded, following annealing of the 3' adapter to the 5' adapter, the 3' adapter additionally comprises a single, double or more bases at its 5' terminus that are not complementary to oligonucleotide b. In other embodiments, the 3' adapter is a modified polynucleotide. Modified oligonucleotides contemplated for use are disclosed in United States Patent Application Publication Number 2011/0129832, incorporated by reference in its entirety. In a specific embodiment, the 3' adapter comprises a base modification selected from the group consisting of a locked nucleic acid (LNA) and a peptide nucleic acid (PNA). In certain embodiments, the 3'-adapter oligonucleotide is pre-annealed to the 5'-adapter.

In one aspect, methods disclosed herein that include a nick-translation-ligation step will improve current library preparation methods comprising substrate molecules that comprise a non-ligatable 5' end, for example, those that lack a 5' phosphate at their termini, by increasing library yield. Thus, in some embodiments, current commercial library preparation methods (e.g., TruSeq™, Illumina) are improved by increasing library yield (FIG. 30). The improvement is achieved by adding dNTPs and a DNA polymerase possessing nick-translation activity (e.g., Taq polymerase) to a ligation reaction mixture and performing the reaction as recommended by the Illumina protocol. Next, a short (for example, from about 5 to about 15 minutes) incubation at about 40-45° C. is performed. In some embodiments, the reaction takes place in the absence of the additional incubation step. The nick-translation step converts any non-ligated 5' terminus of the substrate into ligation-competent 5' phosphate termini. This results in more functional library molecules that have both adapter sequences covalently attached at both termini. In the absence of the subsequent nick-translation ligation reaction, any substrate molecules with one or both of its 5' termini damaged or unphosphorylated will be lost from the library preparation.

In one embodiment, oligonucleotide 2 of the 3' adapter functions as the 5' adapter. In this embodiment, the 3' adapter ligation mix contains not only a DNA ligase but also deoxynucleotide triphosphates and a DNA polymerase capable of nick-translation DNA synthesis. As a result, in a simultaneous reaction, attachment of oligonucleotide 1 of the 3' adapter to the substrate molecule is immediately followed by nick-translation and ligation of the 5' adapter (oligonucleotide 2).

In another embodiment, a DNA polymerase capable of nick-translation DNA synthesis and deoxynucleotide triphosphates can be added to the ligation mix upon completion of the 3' adapter ligation and the subsequent nick translation mediated ligation can be performed in the same reaction vessel without the need for a DNA purification step between the sequential incubations. In further embodiments, the method improves efficiencies of adapter ligation methods.

In another aspect, methods of the disclosure include those that combine non-phosphorylated adapters with a nick translation-ligation step. In such embodiments, formation of adapter dimers is eliminated.

To avoid adapter dimers, some current methods use adenylated DNA substrates with single T overhang compatible cohesive end adapters which are incapable of self-ligation. Other kits currently in use employ non-phosphorylated adapters and adapter ligation to only one DNA strand of the substrate, specifically, to the 5' end of the substrate, followed by nick-translation to covalently attach the adapter to the 3' end (e.g., Life Technologies Ion Torrent™). Nick translation in these cases proceeds to the terminus of the ligated adapter, resulting in attachment of a DNA sequence to the 3' end of the substrate that is complementary to the previously attached 5' adapter sequence. In such a method, however, a mixture of two adapters (e.g., P5 and P7 for Illumina) are used in the ligation reaction. As a result, only 50% of the DNA substrate molecules that are ligated at both ends receive two different adapters, while the remainder have either P5-P5 or P7-P7 combinations. This leads to a two-fold lower yield of functional library molecules (FIG. 31).

The present disclosure also introduces, in some aspects, an alternative approach to prevent adapter-dimer formation. In one aspect, the method uses non-phosphorylated adapters followed by limited nick-translation with one, two or three triphosphate nucleotides (FIG. 32). This enables covalent attachment of an adapter to the 3' terminus of the substrate molecule that is not complementary to the previously attached 5' adapter. By limiting the nick translation reaction, the non-complementarity between the single-stranded portions of the adapter is preserved. Thus, 100% of DNA substrate molecules that are ligated at both termini have both adapters present, which increases the yield of functional library molecules by two-fold.

In one aspect, oligonucleotide 2 of the 3' adapter is the 5' adapter and oligonucleotide 1 lacks a 5' phosphate. In this case, only the 3' end of the 5' adapter becomes ligated to the 5' end of the substrate molecule while the 5' end of the adapter forms a nick with the 3' end of the substrate molecule. In an embodiment, the ligation mix also contains a limited set of deoxynucleotide triphosphates and a DNA polymerase capable of nick-translation DNA synthesis, resulting in a limited nick-translation reaction and extension of the substrate DNA 3' end into the adapter sequence by a single base or several bases, along with excision of a single or several bases from the 5' end of the 3' adapter (oligonucleotide 1) and ligation of the substrate DNA 3' end to the 5' end of the 3' adapter (oligonucleotide 1).

In another embodiment, a DNA polymerase capable of nick-translation DNA synthesis and a limited set of deoxynucleotide triphosphates is added to the ligation mix upon completion of the 5' adapter ligation in the absence of a DNA purification step between the sequential incubations.

In another aspect, the disclosure contemplates a method of producing a processed substrate molecule using sequential adapter ligation and comprising (1) 5' adapter ligation, and (2) 3' adapter ligation which comprises (a) 3' adapter annealing, (c) excising one or more 5' bases of the 3' adapter, and (d) 3' adapter ligation (FIGS. 33, 34). In this aspect, the 5'adapter comprises oligonucleotides a and b. Oligonucleotide a of the 5' adapter is 3' truncated, lacks a 5' phosphate, and has modified bases such as deoxyuridine, deoxyinosine, or ribonucleotides that render it degradable. Oligonucleotide b of the 5' adapter has no phosphate at its 5' terminus. When oligonucleotides a and b are annealed, they either create a blunt or cohesive end for ligation to a substrate molecule. In the first ligation reaction, only the 3' end of the 5' adapter becomes ligated to the 5' end of the substrate molecule while the 5' end of the adapter forms a nick with the 3' end of the substrate molecule. After completion of the first ligation reaction, unused 5' adapter is removed using a purification method (e.g., SPRI) and the substrate molecule is then subjected to incubation with a degradation mix containing such enzymes as uracil deoxyglucosylase (UDG), RNase H, endonuclease V, or combination thereof. After degradation of oligonucleotide a, the 3' adapter is annealed to the 3' end of oligonucleotide b of the 5' adapter, followed by incubation with a second ligation mix, which, in addition to DNA ligase, also contains a limited set of deoxynucleotide triphosphates and a DNA polymerase capable of nick-translation DNA synthesis. This results in a limited nick-translation reaction and extension of the substrate molecule 3' end into the adapter sequence by a single base or several bases, along with excision of a single or several bases from the 5' end of the 3' adapter and ligation of the substrate molecule 3' end to the 5' end of the 3' adapter (FIG. 33). Alternatively, the second ligation mix comprises a ligase and a 5' flap endonuclease, which results in excision of the 5' bases of the 3' adapter, followed by ligation of the 3' end of the substrate to the 5' end of the 3' adapter (FIG. 34). In some embodiments, degradation of oligonucleotide a, replacement with the 3' adapter, limited nick-translation and ligation occur in one reaction vessel as a single incubation step.

Enzymes

Ligases that may be used according to standard reaction conditions to practice the methods of the disclosure include but are not limited to T4 DNA ligase, T4 RNA ligase, T3 DNA ligase or T7 DNA ligase, Taq DNA ligase, Ampligase, E. coli DNA ligase and E. coli RNA ligase. The disclosure contemplates, in various embodiments, reaction conditions appropriate for a blunt end or a cohesive ("sticky") end ligation. The cohesive end, in some embodiments, comprises either a 5' overhang or a 3' overhang.

Examples of enzymes useful in the methods of the disclosure to remove a 5' or a 3' phosphate include, but are not limited to, any phosphatase enzyme, such as calf intestinal alkaline phosphatase, bacterial alkaline phosphatase, shrimp alkaline phosphatase, Antarctic phosphatase, and placental alkaline phosphatase, each used according to standard conditions. Additionally, the phosphatase activity of T4 polynucleotide kinase can be used to remove 3' phosphate groups.

The polymerase enzymes useful in the practice of the invention include but are not limited to a DNA polymerase (which can include a thermostable DNA polymerase, e.g., a Taq DNA polymerase), RNA polymerase, DNA polymerase I and reverse transcriptase. Non-limiting examples of enzymes that may be used to practice the present invention include but are not limited to Deep VentR™ DNA Polymerase, LongAmp™ Taq DNA Polymerase, Phusion™ High-Fidelity DNA Polymerase, Phusion™ Hot Start High-Fidelity DNA Polymerase, Kapa High-Fidelity DNA Polymerase, Q5 High-Fidelity DNA Polymerase, Platinum Pfx High-Fidelity Polymerase, Pfu High-Fidelity DNA Polymerase, Pfu Ultra High-Fidelity DNA Polymerase, KOD High-Fidelity DNA Polymerase, iProof High-Fidelity Polymerase, High-Fidelity 2 DNA Polymerase, Velocity High- Fidelity DNA Polymerase, ProofStart High-Fidelity DNA Polymerase, Tigo High-Fidelity DNA Polymerase, Accuzyme High-Fidelity DNA Polymerase, VentR® DNA Polymerase, DyNAzyme™ II Hot Start DNA Polymerase, Phire™ Hot Start DNA Polymerase, Phusion™ Hot Start High-Fidelity DNA Polymerase, Crimson LongAmp™ Taq DNA Polymerase, DyNAzyme™ EXT DNA Polymerase, LongAmp™ Taq DNA Polymerase, Phusion™ High-Fidelity DNA Polymerase, Taq DNA Polymerase with Standard Taq (Mg-free) Buffer, Taq DNA Polymerase with Standard Taq Buffer, Taq DNA Polymerase with ThermoPol II (Mg-free) Buffer, Taq DNA Polymerase with ThermoPol Buffer, Crimson Taq™ DNA Polymerase, Crimson Taq™ DNA Polymerase with (Mg-free) Buffer, Phire™ Hot Start DNA Polymerase, VentR® (exo-) DNA Polymerase, Hemo Klen-Taq™, Deep VentR™ (exo-) DNA Polymerase, Deep VentR™ DNA Polymerase, DyNAzyme™ EXT DNA Polymerase, Hemo KlenTaq™, LongAmp™ Taq DNA Polymerase, ProtoScript® AMV First Strand cDNA Synthesis Kit, ProtoScript® M-MuLV First Strand cDNA Synthesis Kit, Bst DNA Polymerase, Full Length, Bst DNA Polymerase, Large Fragment, 9° Nm DNA Polymerase, DyNAzyme™ II Hot Start DNA Polymerase, Hemo KlenTaq™, Sulfolobus DNA Polymerase IV, Therminator™ y DNA Polymerase, Therminator™ DNA Polymerase, Therminator™ II DNA Polymerase, Therminator™ III DNA Polymerase, Bsu DNA Polymerase, Large Fragment, DNA Polymerase I (E. coli), DNA Polymerase I, Large (Klenow) Fragment, Klenow Fragment (3'→5' exo-), phi29 DNA Polymerase, T4 DNA Polymerase, T7 DNA Polymerase (unmodified), Terminal Transferase, Reverse Transcriptases and RNA Polymerases, E. coli Poly(A) Polymerase, AMV Reverse Transcriptase, M-MuLV Reverse Transcriptase, phi6 RNA Polymerase (RdRP), Poly(U) Polymerase, SP6 RNA Polymerase, and T7 RNA Polymerase.

The enzymes possessing flap endonuclease activity that are useful in the disclosure include but are not limited to flap endonuclease 1 (FEN1), T5 exonuclease, Taq DNA polymerase, Bst polymerase, Tth polymerase, DNA polymerase I and their derivatives.

EXAMPLES

Example 1

Comparison of Conventional Adapter Ligation to 3' Adapter Ligation with FAM-Labeled Oligonucleotides Rationale:

Using a FAM-labeled oligonucleotide system, blunt ligation using fill-in adapters (FIG. 2A) or 3' adapters (FIG. 3) was tested at different molar ratios of substrate to adapter to examine the effect on ligation efficiency and chimera formation.

Materials:

Fill-in adapter contains oligonucleotides 12-900 and 13-426 (Table 1)

3'Adapter; $1^{st}$ oligonucleotide 13-340 (Table 1)

3'Adapter; $2^{nd}$ oligonucleotide option 1 (with a blocking 3' deoxythymidine base at the 3' terminus) 13-559 (Table 1)

3'Adapter; $2^{nd}$ oligonucleotide option 2 (a phosphate group at the 3' terminus) 13-558 (Table 1)

FAM substrate A composed of oligonucleotides 13-562 and 13-563, where the FAM group labels ligation to the 5' Phosphate of the substrate (Table 1)

FAM substrate B composed of oligonucleotides 13-561 and 13-564, where the FAM group labels ligation to the 3' OH of the substrate and where the corresponding 5' terminus of the substrate has a phosphate (Table 1)

FAM substrate C composed of oligonucleotides 13-560 and 13-564, where the FAM group labels ligation to the 3' OH of the substrate and where the corresponding 5' terminus of the substrate lacks a phosphate (Table 1)

T4 DNA Ligase (Rapid) (Enzymatics, Cat# L6030-HC-L)

10×T4 DNA Ligase Buffer (Enzymatics, Cat# B6030)

Method:

Conventional adapter ligation reactions were assembled in a total volume of 10 µl, comprising 1×T4 DNA Ligase Buffer, 10 pmoles of FAM substrate A, 20 or 200 pmoles of Fill-in adapter, 600 units T4 DNA Ligase (Rapid) or no ligase.

3' adapter ligation reactions were assembled in a total volume of 10 µl, containing 1×T4 DNA Ligase Buffer, 10 pmoles of FAM substrate B or 10 pmoles of FAM substrate C, 20 or 200 pmoles of 3'Adapter option 1 or 20 or 200 pmoles of 3'Adapter option 2 and 600 units T4 DNA Ligase (Rapid) or no T4 DNA ligase.

All ligation reactions were performed at 25° C. for 30 minutes. The total ligation reaction volume (10 µl) was mixed with 10 µl of 2× formamide loading buffer (97% formamide, 10 mM EDTA, 0.01% bromophenol blue and 0.01% xylene cyanol), heated at 95° C. for 5 minutes and subsequently run on a pre-cast 15% polyacrylamide gel, TBE-Urea (Invitrogen, Cat# S11494) in an oven at 65° C., visualized on a Dark reader light box (Clare Chemical Research) and photographed using a digital camera. Subsequently the gel was stained SYBR® Gold nucleic acid gel stain (Invitrogen, Cat# S11494) (not shown).

Results:

FAM substrate A was converted into ligation product in the presence of the fill-in adapter and T4 DNA ligase (FIG. 19, lanes 1-2). This conventional adapter ligation showed some FAM substrate A chimera formation when a ratio of only 2:1 adapter:substate (FIG. 19, lane 1) was used compared to a ratio of 20:1 (lane 2). No ligation product was observed in absence of T4 DNA ligase (FIG. 19, lane 3).

Different scenarios of 3' adapter ligation were tested in lanes 4 to 12 (FIG. 19). Lanes 4 and 5 show ligation reactions between FAM substrate B and 3' Adapter option 1. At 2:1 (lane 4) or 20:1 (lane 5) adapter:substate ratio, chimeric products of higher molecular weight formed which may or may not involve the 3' Adapter. However, the ligation product was more abundant and its formation favored at a ratio of 20:1 adapter:substate (lane 5). Lanes 6 and 7 show ligation reactions between FAM substrate C and 3' Adapter option 1. The reaction was favored at a ratio of 20:1 adapter:substate (lane 7) and no chimeric products were observed. Lanes 8 and 9 show ligation reactions between FAM substrate B and 3' Adapter option 2. No ligation product was observed, however chimeric products were detected. Lanes 10 and 11 show ligation reactions between FAM substrate C and 3' Adapter option 2. No ligation product was observed. No ligation product was observed in absence of T4 DNA ligase (lane 12).

Conclusion:

Conventional adapter ligation required a 5'-phosphate on the FAM substrate which led to the formation of chimeras if the fill-in adapters were not in excess. Ligation of the 3' Adapter was more efficient and with fewer chimeras when the FAM substrate had a 5'hydroxy group and the 3' Adapter had a blocking 3-deoxythymidine base (option 1) which prevented ligation between adapter molecules and favored the ligation between substrate and adapter. In both cases, the ratio of adapter:substate of 20:1 was favored for ligation product formation.

Example 2

Comparison of Conventional Adapter Ligation to 3' Adapter Ligation with Sheared, Size-Selected Genomic DNA Rationale:

This experiment was performed to test the effect of polishing of physically sheared genomic DNA on the efficiency of conventional or 3' adapter ligation Materials:

Fill-in adapter contains oligonucleotides 13-489 and 13-426 (Table 1)

3'Adapter; $1^{st}$ oligonucleotide 13-340 (Table 1) and 2nd oligonucleotide option 1 (containing a blocking 3' deoxythymidine base at the 3' terminus) 13-559 (Table 1)

NEBuffer 2 (New England Biolabs, cat#B7002S)

100 mM 2'-deoxynucleoside 5'-triphosphate (dNTP) Set, PCR Grade (Invitrogen (Life technologies), cat#10297-018)

Adenosine 5'-Triphosphate (ATP) (New England Biolabs, cat# P0756S)

DNA Polymerase I, Large (Klenow) Fragment (New England Biolabs, cat#M0210S)

T4 DNA polymerase (New England Biolabs, cat# M0203S)

T4 Polynucleotide Kinase (New England Biolabs, cat# M0201S)

Exonuclease III (*E. coli*) (New England Biolabs, cat# M0293S)

Antarctic Phosphatase (New England Biolabs, cat# M0289S)

Antarctic Phosphatase reaction buffer (New England Biolabs, cat# B0289S)

T4 DNA Ligase (Rapid) (Enzymatics, cat# L6030-HC-L)

10×T4 DNA Ligase Buffer (Enzymatics, cat# B6030)

*E. coli* genomic DNA ATCC 11303 strain (Affymetrix, cat#14380)

M220 Focused-ultrasonicator, (Covaris, cat# PN 500295)

Pippin Prep (Sage Science)

CDF2010 2% agarose, dye free w/internal standards (Sage Science)

DNA Clean & Concentrator-5 (Zymo research, cat#D4004)

25 bp ladder DNA size marker (Invitrogen (Life technologies), cat#10488-022)

Method:

*E. coli* gDNA was resuspended in DNA suspension buffer (Teknova, cat#T0227) at a concentration of 100 ng/ul. The DNA was fragmented with the M220 Focused-ultrasonicator to 150 base pairs average size. A tight size distribution of fragmented DNA from ~150 bp to ~185 bp was subsequently isolated on a 2% agarose gel using Pippin Prep.

200 ng of the size-selected DNA was subjected to the activity of different enzymes. The reactions were assembled in a total volume of 30 µl, comprising a final concentration of 1×NEBuffer 2, 100M of each dNTP, 3 units T4 DNA polymerase or 5 units DNA Polymerase I, Large (Klenow) Fragment or 3 units T4 DNA polymerase and 5 units DNA Polymerase I, Large (Klenow) Fragment or 3 units T4 DNA polymerase and 5 units DNA Polymerase I, Large (Klenow) Fragment and 1 unit of Exonuclease III. Another reaction was assembled in a total volume of 30 µl comprising a final concentration 1×NEBuffer 2, 1 mM ATP, 10 units of T4 Polynucleotide Kinase. Another reaction was assembled in a total volume of 30 µl comprising a final concentration 1× Antarctic Phosphatase reaction buffer and 5 units of Antarctic phosphatase. A control reaction was assembled with 200 ng of the size-selected DNA with 1×NEBuffer 2. All reactions were incubated at 37° C. for 30 minutes and the DNA purified using the DNA Clean & Concentrator-5 columns. DNA was eluted in 30 µl of DNA suspension buffer and divided into 2 tubes of 15 µl for subsequent conventional adapter ligation or 3' adapter ligation. The conventional adapter ligations were assembled in a total volume of 30 µl comprising 1×T4 DNA Ligase Buffer, Fill-in adapter containing oligonucleotides 13-489 (220 pmoles) and 13-426 (440 pmoles), and 1200 units of T4 DNA Ligase (Rapid). The 3' adapter ligation reactions were assembled in a total volume of 30 µl, containing 1×T4 DNA Ligase Buffer, 220 pmoles of 3' Adapter $1^{st}$ oligonucleotide, 440 pmoles of 3'Adapter $2^{nd}$ oligonucleotide and 1200 units T4 DNA Ligase (Rapid). All reactions were purified using DNA Clean & Concentrator-5-columns. The DNA was resuspended in 10 µl of DNA suspension buffer and was mixed with 10 µl of 2× formamide loading buffer (97% formamide, 10 mM EDTA, 0.01% bromophenol blue and 0.01% xylene cyanol), heated at 95° C. for 5 minutes and subsequently run on a pre-cast 6% polyacrylamide gel, TBE-Urea (Invitrogen, Cat# S11494) in an oven at 65° C. The gel was stained SYBR® Gold nucleic acid gel stain (Invitrogen, Cat# S11494) and visualized on a Dark reader light box (Clare Chemical Research) and photographed using a digital camera.

Results:

The conventional adapter ligation reactions (FIG. 20, upper panel) which require a 5' phosphate on the sheared DNA substrate showed a lower efficiency than the 3' adapter ligation which does not (FIG. 20, lower panel). The ligation reactions were more efficient after treating DNA with T4 DNA polymerase alone (lane 3) or in combination with Klenow (lane 7) or Klenow plus Exonuclease III (lane 8) for both types of ligations. Treatment with Klenow, T4 Polynucleotide Kinase or Antarctic phosphatase alone (lanes 4, 5 and 6, respectively) only moderately enhanced blunt ligation compared to the non-treated DNA (lane 2). The tight range distribution fragmented DNA was loaded on lane 9.

Conclusion:

Ligation of blunt adapters to sheared DNA highly depends on the polishing of this DNA. DNA polymerases like T4 DNA polymerase which present a strong 5' to 3' exonuclease activity and a 5' to 3' polymerase activity are well suited for this purpose. The conventional adapter ligation reaction depends on the presence of an intact 5' phosphate on the substrate's blunt end. However, ligation of the 3' adapter does not, since the ligation occurs at the 3' hydroxyl terminus of the fragmented DNA. Since the 5' termini of sheared DNA are not enzymatic substrates for T4 DNA polymerase, this explains why the 3' adapter was more successfully ligated than the fill-in adapter (lane 3). The combination of T4 DNA Polymerase plus Klenow and Exonuclease III significantly enhanced the blunt ligation. Exonuclease III activity produced blunt ends required for ligation of blunt adapters by removing 3' hydroxyl termini which could be damaged at the 3' terminus of DNA. Exonuclease III also possesses a 3' phosphatase activity, which makes the 3' terminus accessible to DNA polymerase polishing activity.

Example 3

Temperature Optimization for 5' Adapter Ligation Using a FAM-Labeled Oligonucleotide Substrate Rationale:

This experiment assessed the temperature dependence and dNTP composition on nick translation mediated 5' adapter ligation.

Materials:

5' adapter oligonucleotide for nick-translation (13-144) (Table 1)

FAM oligonucleotide substrate (13-581) (Table 1)

Oligonucleotide template (13-582) (Table 1)

100 mM 2'-deoxynucleoside 5'-triphosphate (dNTP) Set, PCR Grade (Invitrogen (Life technologies), cat#10297-018)

E. coli DNA ligase (New England BioLabs, cat# M0205S)

10×E. coli DNA Ligase Reaction Buffer (New England BioLabs)

Taq DNA polymerase, concentrated 25 U/ul (Genscript, cat# E00012)

25 bp ladder DNA size marker (Invitrogen (Life technologies), cat#10488-022)

Method:

A first set of nick translation reactions was assembled in a total volume of 301, comprising a final concentration of 1×E. coli DNA ligase Buffer, 30 pmoles of FAM oligonucleotide substrate, 45 pmoles of 5' adapter oligonucleotide for nick-translation and 45 pmoles of oligonucleotide template, 200 μM of dTTP or a mix of 200 uM of each dTTP/dGTP or 200 uM of each dATP/dTTP/dGTP and 2.5 units of Taq DNA polymerase or no Taq DNA polymerase. The reactions were incubated at 30° C., 40° C. or 50° C. for 30 minutes.

A second set of nick translation reactions followed by ligations were assembled in 30 ul comprising a final concentration of 1×E. coli DNA ligase Buffer, 30 pmoles of FAM oligonucleotide substrate, 45 pmoles of 5' adapter oligonucleotide for nick-translation and 45 pmoles of oligonucleotide template, 200 uM of each dATP/dTTP/dGTP, and 2.5 units of Taq DNA polymerase. The reactions were incubated at 50° C., 53° C., 56° C. or 60° C. for 30 minutes. 10 μl of those reactions were taken for gel analysis. 10 units of E. coli ligase were added to the 20 μl left and incubated at 25° C. for 15 minutes. An additional control reaction was assembled in 30 ul comprising a final concentration of 1×E. coli DNA ligase Buffer, and 30 pmoles of FAM oligonucleotide substrate. 10 μl of those reactions were mixed with 10 μl of 2× formamide loading buffer (97% formamide, 10 mM EDTA, 0.01% bromophenol blue and 0.01% xylene cyanol), heated at 95° C. for 5 minutes and subsequently run on a pre-cast 15% polyacrylamide gel, TBE-Urea (Invitrogen, cat# S11494) in an oven at 65° C., visualized on a Dark reader light box (Clare Chemical Research) and photographed using a digital camera.

Results:

As shown in FIG. 21, panel A, Taq DNA polymerase elongated the 3' hydroxyl terminus of the 5' adapter oligonucleotide for nick-translation, removing nucleotides on the FAM oligonucleotide substrate by its 5' flap endonuclease activity. Adding dTTP only (FIG. 21, lanes 2, 5, 8, panel A) allowed only the addition of one base at the 3' terminus of the 5' adapter oligonucleotide for nick-translation, adding dTTP/dGTP (FIG. 21, lanes 3, 6, 9, panel A) allowed the addition of three bases and adding dTTP/dGTP/dATP (FIG. 21, lanes 4, 7, 10, panel A) allowed the addition of four bases which was proportional to the number of bases cleaved from the FAM oligonucleotide substrate (FIG. 21, panel A). The number of bases cleaved from the FAM oligonucleotide substrate also depended on the temperature in which the reactions take place. At 50° C. (FIG. 21, lanes 2 to 4, panel A), the amount of bases cleaved from the FAM oligonucleotide substrate was greater than those cleaved at 40° C. or 30° C. The efficiency of the nick translation and the amount of FAM oligonucleotide substrate cleaved was also highly dependent on the temperature of the reaction. At 40° C. or 30° C., adding dTTP only (FIG. 21, lanes 5, 8, panel A), did not allow any cleavage of the FAM oligonucleotide substrate, as observed at 50° C. (FIG. 21, lane 2, panel A). Adding dTTP/dGTP or dTTP/dGTP/dATP allowed some cleavage at 40° C. (lanes 6 and 7) or 30° C. (lanes 9 and 10) at a lower efficacy than at 50° C. (lanes 3 and 4). Lane 1 (FIG. 21, panel A) shows FAM oligonucleotide substrate in the absence of Taq DNA polymerase.

The efficiency of nick translation and the amount of FAM oligonucleotide substrate cleaved was highly dependent on the temperature of the reaction. At 60° C., the FAM oligonucleotide substrate was almost entirely processed to smaller species (FIG. 21, lane 4, panel B). The FAM oligonucleotide substrate cleavage product size also decreased as the temperature of the reaction increased (FIG. 21, lanes 1 to 4, panel B). Lane 5 (FIG. 21, panel B) shows the FAM oligonucleotide substrate in the absence of Taq DNA polymerase. During the nick translation reaction, Taq DNA polymerase cleaves the 5' terminus of the FAM oligonucleotide substrate and generates a terminal 5' phosphate that is essential for E. coli ligase to covalently attach the 3' terminus of the 5' adapter oligonucleotide to the 5' terminus of the FAM oligonucleotide substrate. The ligation efficiency was also dependent on the temperature at which the reaction took place. The ligation product was more abundant at 50° C. (lane 6) and almost absent at 60° C. (lane 9), and an intermediate amount of ligation product was generated at 53° C. and 56° C.

Conclusion:

During nick translation, the number of bases cleaved from the FAM oligonucleotide substrate depended on the complementary dNTPs introduced in the reaction and the temperature at which the reactions took place. During the nick translation reaction, Taq DNA polymerase cleaves the 5' terminus of the FAM oligonucleotide substrate and generates a terminal 5' phosphate that is essential for E. coli ligase to ligate two fragments. FAM oligonucleotide substrates cleaved by nick translation at higher temperatures were poor substrates for ligation by E. coli ligase because of a potential gap formed between the 3' terminus of the 5' adapter oligonucleotide and the 5' terminus of the FAM oligonucleotide substrate.

Example 4

Analysis of dNTP Composition Effects on 5' Adapter Ligation

Rationale:

This experiment was performed to assess the degree of nick-translation that occurs in the presence of varied dNTP composition and the effect on the coupled ligation reaction.

Materials:

5' adapter oligonucleotide for nick-translation (13-144) (Table 1)

FAM oligonucleotide substrate (13-581) (Table 1)

Oligonucleotide template (13-582) (Table 1)

100 mM 2'-deoxynucleoside 5'-triphosphate (dNTP) Set, PCR Grade (Invitrogen (Life technologies), cat#10297-018)

25 bp ladder DNA size marker (Invitrogen (Life technologies), cat#10488-022)

E. coli DNA ligase (Enzymatics, cat# L6090L)

10×E. coli DNA ligase Buffer (Enzymatics, cat# B6090)

Taq-B DNA polymerase (Enzymatics, cat# P7250L)

Method:

The reactions were assembled in a total volume of 30l, comprising a final concentration of 1×E. coli DNA ligase Buffer, 30 pmoles of FAM oligonucleotide substrate, 45 pmoles of 5' adapter oligonucleotide for nick-translation and 45 pmoles of oligonucleotide template, 200 µM of each 4 dNTP or a mix of 200 µM of each: dCTP, dTTP, dGTP or dATP, dTTP, dGTP or dATP, dCTP, dGTP or dATP, dTTP, dCTP or no dNTP, 10 units of E. coli ligase and 10 units of Taq-B DNA polymerase. All reactions were incubated at 40° C. for 30 minutes. 10 µl of those reaction were mixed with 10 µl of 2× formamide loading buffer (97% formamide, 10 mM EDTA, 0.01% bromophenol blue and 0.01% xylene cyanol), heated at 95° C. for 5 minutes and subsequently run on a pre-cast 15% polyacrylamide gel, TBE-Urea (Invitrogen, Cat# S11494) in an oven at 65° C., visualized on a Dark reader light box (Clare Chemical Research) and photographed using a digital camera (lower panel). Subsequently the gel was stained SYBR® Gold nucleic acid gel stain (Invitrogen, Cat# S11494), visualized on a Dark reader light box (Clare Chemical Research) and photographed using a digital camera (upper panel).

Results:

The first two lanes of FIG. 22 show control oligonucleotide. In the absence of Taq-B DNA polymerase, E. coli ligase alone cannot ligate the 5' adapter oligonucleotide to the FAM oligonucleotide substrate because the FAM substrate lacks a 5' phosphate modification (FIG. 22, lane 3). In the presence of Taq-B DNA polymerase and the 4 dNTPs, the 5' adapter oligonucleotide was extended, forming a new product of 58 bases and the FAM oligonucleotide substrate was displaced and degraded by the 5' flap endonuclease activity of Taq-B DNA polymerase (FIG. 22, lane 4). In the presence of E. coli ligase, Taq-B DNA polymerase and dATP/dTTP/dGTP (FIG. 22, lane 7) or dCTP/dTTP/dGTP (FIG. 22, lane 6) or dATP/dTTP/dCTP (FIG. 22, lane 9), nick translation was limited to the addition of four, three or one bases, respectively. With the extension of the 5' adapter, a flap was formed at the 5' terminus of the FAM oligonucleotide substrate. This flap becomes a substrate for the Taq-B 5' flap endonuclease activity creating a required 5' phosphate for ligation. The 5' adapter was ligated to the FAM oligonucleotide substrate forming a product of 69 bases. A flap of three or four bases (FIG. 22, lane 6 and 7) supported the ligation more efficiently than the one base flap (FIG. 22, lane 9). In the presence of E. coli ligase, Taq-B DNA polymerase and dATP/dCTP/dGTP (FIG. 22, lane 8), a faint band corresponding to the ligation product was observed. A weak ligation activity may come from the incorporation of an "unmatched" base (A C or G instead of T), leading to formation of the flap on some FAM oligonucleotide substrates. In the presence of E. coli ligase, Taq-B DNA polymerase and no dNTP, no ligation product was observed. In the presence of E. coli ligase, Taq-B DNA polymerase and the 4 dNTPs, the 5' adapter was ligated to the FAM oligonucleotide substrate forming a product of 69 bases (FIG. 22, lane 5). Since the 5' adapter and the oligonucleotide template were in excess compared to the FAM oligonucleotide substrate, a nick translation product was also observed at 58 bases (FIG. 22, lane 5, upper panel). However, the same amount of ligation product was observed. The 25 bp ladder DNA size marker was loaded on lane M.

Conclusion:

Phosphorylation of the 5' terminus of the FAM oligonucleotide substrate is required for ligation. The polymerase activity of Taq DNA polymerase in the presence of dNTPs is required to perform the extension of the 5' adapter, which creates a flap at the 5' terminus of the FAM oligonucleotide substrate. This flap is a good substrate for the 5' flap endonuclease activity of Taq DNA polymerase, generating a perfect 5' phosphate substrate for ligation by E. coli ligase. The ligation occurs even if the flap is only formed by one base. The ligation also occurs when all four dNTPs are present which does not restrict the length of the flap or the extent of nick translation, suggesting that the ligation occurs immediately after a 5'phosphate is created at the 5' terminus of the FAM oligonucleotide substrate.

Example 5

Coupled Nick Translation-Ligation Reaction with Thermo Stable Enzymes

Rationale:

This experiment was performed to assess the effect of reaction temperature and number of units of Taq DNA Polymerase enzyme in the coupled reaction.

Materials:

5' adapter oligonucleotide for nick-translation (13-144) (Table 1)

FAM oligonucleotide substrate (13-581) (Table 1)

Oligonucleotide template (13-582) (Table 1)

100 mM 2'-deoxynucleoside 5'-triphosphate (dNTP) Set, PCR Grade (Invitrogen (Life technologies), cat#10297-018)

Taq DNA ligase (New England BioLabs, cat# M0208S)

10× Taq DNA ligase Reaction Buffer (New England BioLabs)

Taq DNA polymerase, concentrated 25 U/ul (Genscript, cat# E00012)

Method:

The reactions were assembled in a total volume of 30 µl, comprising a final concentration of 1× Taq DNA ligase reaction Buffer, 30 pmoles of FAM oligonucleotide substrate, 45 pmoles of 5' adapter oligonucleotide for nick-translation and 45 pmoles of oligonucleotide template, 200 µM of each: dATP, dTTP, dGTP or dTTP, 40 units of Taq DNA ligase, or 80 units Taq DNA ligase, or 120 units Taq DNA ligase and 10 units of Taq DNA polymerase. Reactions were incubated at 45° C., 50° C., 55° C., or 60° C., for 30 minutes. 10 µl of those reactions were mixed with 10 µl of 2× formamide loading buffer (97% formamide, 10 mM EDTA, 0.01% bromophenol blue and 0.01% xylene cyanol), heated at 95° C. for 5 minutes and subsequently run on a pre-cast 15% polyacrylamide gel, TBE-Urea (Invitrogen, Cat# S11494) in an oven at 65° C., visualized on a Dark reader light box (Clare Chemical Research) and photographed using a digital camera.

Results:

Taq DNA polymerase elongated the 3' hydroxyl terminus of the 5' adapter oligonucleotide, removing nucleotides on the FAM oligonucleotide substrate by its 5' flap endonuclease activity. Adding dTTP/dGTP/dATP (FIG. 23, lanes 2 to 5, panel A) or dTTP (FIG. 23, lanes 6 to 9, panel A) allowed the addition of four and one bases, respectively, at the 3' terminus of the 5' adapter oligonucleotide and the subsequent cleavage of the 5' terminus of the FAM oligonucleotide substrate. At 60° C. the ligation was impaired (FIG. 23, lanes 5 and 9, panel A). The efficiency of ligation was not affected by adding dTTP/dGTP/dATP (FIG. 23, lanes 2 to 5, panel A) or dTTP (FIG. 23, lanes 6 to 9, panel A). The ligation efficiency was dependent on the amount of Taq DNA ligase present in the reaction. The ligation product was more abundant when 120 units of Taq DNA ligase (FIG. 23, lane 4, panel B) were added to the reaction compared to 40 or 80 units (FIG. 23, lane 2 and 3, panel B, respectively). Lane 1, panel A and lane 1, panel B show control oligonucleotides without enzymes.

Conclusion:

During the nick translation reaction, Taq DNA polymerase cleaves the 5' terminus of the FAM oligonucleotide substrate and generates a 5' phosphate terminus essential for Taq DNA ligase between 45° C. and 60° C. to perform ligation. The ligation was reduced at 60° C. The concentration of Taq DNA ligase in the reaction also affected the efficiency of the ligation, as more product was observed in the presence of 120 U enzyme compared to 80 U and 40 U.

Example 6

Coupled Displacement-Cleavage-Ligation Reaction

Rationale:

This experiment was performed to demonstrate that either thermostable Taq DNA ligase or thermolabile *E. coli* ligase can be combined with Taq DNA Polymerase in the coupled displacement-cleavage ligation reaction.

Materials:

5' adapter oligonucleotide for displacement-cleavage (13-156) (Table 1)
FAM oligonucleotide substrate (13-581) (Table 1)
Oligonucleotide template (13-582) (Table 1)
Taq DNA ligase (New England BioLabs, cat# M0208S)
10× Taq DNA ligase Reaction Buffer (New England BioLabs)
Taq DNA polymerase, concentrated 25 U/ul (Genscript, cat# E00012)
*E. coli* DNA ligase (New England BioLabs, cat# M0205S)
10×*E. coli* DNA Ligase Reaction Buffer (New England BioLabs)

Method:

The reactions were assembled in a total volume of 30 µl, comprising a final concentration of 1×*E. coli* DNA ligase reaction Buffer or 1× Taq DNA ligase reaction Buffer, 30 pmoles of FAM oligonucleotide substrate, 45 pmoles of 5' adapter oligonucleotide for displacement-cleavage and 45 pmoles of oligonucleotide template, 10 units of *E. coli* DNA ligase or 40 units Taq DNA ligase, and 10 units of Taq DNA polymerase. Reactions were incubated at 40° C. or 45° C. for 30 minutes. 10 µl of those reactions were mixed with 10 µl of 2× formamide loading buffer (97% formamide, 10 mM EDTA, 0.01% bromophenol blue and 0.01% xylene cyanol), heated at 95° C. for 5 minutes and subsequently run on a pre-cast 15% polyacrylamide gel, TBE-Urea (Invitrogen, Cat# S11494) in an oven at 65° C., visualized on a Dark reader light box (Clare Chemical Research) and photographed using a digital camera.

Results:

The 5' adapter oligonucleotide for displacement-cleavage has an extra matching base "T" at is 3' terminus, which overlaps with the 5' terminus of the FAM oligonucleotide substrate. When the 3' terminus of the 5' adapter oligonucleotide displaces the 5' terminus of the FAM oligonucleotide substrate, the 5' flap endonuclease activity of Taq DNA polymerase cleaves the 5' terminus of the FAM oligonucleotide substrate to create a 5' phosphate which is essential for the ligation with *E. coli* ligase (FIG. 24, lane 2, panel A) or Taq DNA ligase (FIG. 24, lane 2, panel B). Lane 1 for panels A and B show oligonucleotide controls without enzymes.

Conclusion:

In the absence of dNTPs, no extension of the 5' adapter occurs. However, Taq DNA polymerase can cleave the 5' terminus of the FAM oligonucleotide substrate and generates a terminal 5' phosphate that is essential for *E. coli* DNA ligase or Taq DNA ligase to perform ligation.

Example 7

Coupled Displacement-Cleavage-Ligation Reaction with Either "N" Universal/Degenerate or "T" Substrate-Specific 5' Adapter 3' Overhang Rationale:

This experiment demonstrates that 5' adapter ligation using a flap endonuclease can be performed if either the 5' adapter 3' terminal overhang is a sequence-specific match or if it is composed of a degenerate non sequence-specific 'N'.

Materials:

5' adapter oligonucleotide for displacement-cleavage "T" (13-607) (Table 1)
5' adapter oligonucleotide for displacement-cleavage "N" (13-596) (Table 1)
FAM oligonucleotide substrate (13-581) (Table 1)
Oligonucleotide template (13-582) (Table 1)
Taq DNA ligase (New England BioLabs, cat# M0208S)
10× Taq DNA ligase Reaction Buffer (New England BioLabs)
Taq DNA polymerase, concentrated 25 U/ul (Genscript, cat# E00012)
*E. coli* DNA ligase (New England BioLabs, cat# M0205S)
10×*E. coli* DNA Ligase Reaction Buffer (New England BioLabs)

Method:

The reactions were assembled in a total volume of 301, comprising a final concentration of 1× Taq DNA ligase reaction buffer, 30 pmoles of FAM oligonucleotide substrate, 45 pmoles of 5' adapter oligonucleotide "T" or 45 pmoles of 5' adapter oligonucleotide "N" 1 or 180 pmoles of 5' adapter oligonucleotide "N" or 450 pmoles of 5' adapter oligonucleotide "N" and 45 pmoles of oligonucleotide template, 40 units Taq DNA ligase, and 10 units of Taq DNA polymerase. Reactions were incubated at 45° C. or 50° C. or 55° C. for 30 minutes or cycling 8 times between 45° C. for 3 minutes, 65° C. for 15 seconds. 10 µl of those reactions were mixed with 10 µl of 2× formamide loading buffer (97% formamide, 10 mM EDTA, 0.01% bromophenol blue and 0.01% xylene cyanol), heated at 95° C. for 5 minutes and subsequently run on a pre-cast 15% polyacrylamide gel, TBE-Urea (Invitrogen, Cat# S11494) in an oven at 65° C., visualized on a Dark reader light box (Clare Chemical Research) and photographed using a digital camera.

Results:

When the 5' adapter oligonucleotide for displacement-cleavage has a "T" at its 3' terminus matching the oligonucleotide template (FIG. 25, lanes 3, 5, 7, panel A), (which overlaps with the 5' terminus of the FAM oligonucleotide substrate), ligation occurred at a higher rate than when the 5' adapter oligonucleotide had a degenerate "N" base, where during oligo synthesis, all four nucleotides were present at this position (FIG. 25, lanes 2, 4, 6, panel A), which is only a perfect match to the oligonucleotide template one fourth of the time. Different reaction temperatures (45° C., 50° C. and 55° C.), were tested without improving the ligation using the 5' adapter oligonucleotide "N" (FIG. 25, lanes 2, 4, 6, panel A). Also, different amounts of 5' adapter oligonucleotide "N" (45 pmoles, 180 pmoles and 450 pmoles), were tested without improving the ligation reaction (FIG. 25, lanes 3 to 5, panel B). However, temperature cycling of the reaction between 45° C. and 65° C. allowed the ligation to occur at the highest rate which was comparable to the "T" matching base 5' adapter oligonucleotide (FIG. 25, lane 6, panel B). Lane 1 for panels A and B show oligonucleotide controls without enzymes.

Conclusion:

To allow efficient 5' adapter ligation coupled to displacement-cleavage using the 5' adapter oligonucleotide "N", cycling between a first temperature for Taq DNA ligase to operate and a second temperature where the duplex between the oligonucleotide template and the 5' adapter oligonucleotide "N" could dissociate was critical. The cycling conditions permitted multiple associations between the 5' adapter oligonucleotide "N" and the oligonucleotide template where the displacement-cleavage reaction occurred only if the 3' terminal base of the 5' adapter oligonucleotide is a perfect match to the template and can displace the 5' terminus of the FAM oligonucleotide substrate.

Example 8

Coupled Nick-Translation-Ligation Reaction Using DNA Polymerase I

Rationale:

This experiment demonstrates that a DNA polymerase I, which possesses 5'-3' exonuclease activity, can also participate in the nick translation coupled adapter ligation method.

Materials:

5' adapter oligonucleotide for nick-translation (13-144) (Table 1)
FAM oligonucleotide substrate (13-581) (Table 1)
Oligonucleotide template (13-582) (Table 1)
100 mM 2'-deoxynucleoside 5'-triphosphate (dNTP) Set, PCR Grade (Invitrogen (Life technologies), cat#10297-018)
25 bp ladder DNA size marker (Invitrogen (Life technologies), cat#10488-022)
E. coli DNA ligase (Enzymatics, cat# L6090L)
10×E. coli DNA ligase Buffer (Enzymatics, cat# B6090)
Taq-B DNA polymerase (Enzymatics, cat# P7250L)
DNA polymerase I (New England Biolabs, cat# M0209S)

Method:

The reactions were assembled in a total volume of 30 µl, comprising a final concentration of 1×E. coli DNA ligase Buffer, 30 pmoles of FAM oligonucleotide substrate, 45 pmoles of 5' adapter oligonucleotide for nick-translation and 45 pmoles of oligonucleotide template, 200 µM of each 4 dNTPs, 10 units of E. coli ligase and 10 units of Taq-B DNA polymerase or 5 units of DNA polymerase I or 1 unit of DNA polymerase I. Reactions were incubated at 40° C., 18° C., 16° C. or 14° C. for 30 minutes. 10 µl of each reaction was mixed with 10 µl of 2× formamide loading buffer (97% formamide, 10 mM EDTA, 0.01% bromophenol blue and 0.01% xylene cyanol), heated at 95° C. for 5 minutes and subsequently run on a pre-cast 15% polyacrylamide gel, TBE-Urea (Invitrogen, Cat# S11494) in an oven at 65° C., visualized on a Dark reader light box (Clare Chemical Research) with an without SYBR gold (upper panel and lower panel, respectively), and photographed using a digital camera.

Results:

The first lane of FIG. 26 shows the no enzyme control. In the presence of Taq-B DNA polymerase and E. coli ligase (FIG. 26, lane 2), the 5' adapter oligonucleotide was either ligated to the FAM oligonucleotide substrate producing a 69 base product (FIG. 26, lane 2, upper and lower panels) or completely extended forming a new product of 58 bases (FIG. 26, lane 2, upper panel). The 69 base product was from extension by Taq-B DNA polymerase and formation of a flap at the 5' end of the FAM oligonucleotide substrate. The Taq-B 5' flap endonuclease activity cut the flap and generated a 5' phosphate that was used by the E. coli ligase to complete the ligation. The 58 base product was obtained when the FAM oligonucleotide substrate was completely displaced during extension and degraded by the 5' flap endonuclease activity of Taq-B DNA polymerase. These two types of products were also formed when Taq-B DNA polymerase was replaced by DNA polymerase I (FIG. 26, lanes 3 to 8) which has a 5'→3' exonuclease activity that removes nucleotides ahead of a growing DNA chain one by one and allows nick translation to occur. The reaction was performed with either 5 units of DNA polymerase I (FIG. 26, lanes 3 to 5) or 1 unit of DNA polymerase I (FIG. 26, lanes 6 to 8). The reaction with the thermophilic Taq-B DNA polymerase was performed at 40° C. (FIG. 26, lane 2) while the reactions performed with the mesophilic DNA polymerase I were at 18° C. (FIG. 26, lanes 3 and 6), 16° C. (FIG. 26, lanes 4 and 7) or 14° C. (FIG. 26, lanes 5 and 8). The 69 base ligation product was obtained in all cases but the addition of only 1 unit of DNA polymerase I (FIG. 26, lanes 6 to 8) was more efficient than with 5 units (FIG. 26, lanes 3 to 5). This is explained by the very strong 5'→3' exonuclease activity of DNA polymerase that causes the rapid partial degradation of the FAM oligonucleotide substrate before it can be ligated. Degradation products were observed in the bottom part of the lower panel (FIG. 26, lanes 3 to 5). The 25 bp ladder DNA size marker was loaded on lane M.

Conclusion:

Taq-B DNA polymerase (thermophilic polymerase) and DNA polymerase I (mesophilic polymerase) can both be used to perform the nick translation mediated ligation but they require different conditions to be fully active. They both generated a 69 base product which was the result of excision of the 5' end followed by ligation but they use different mechanisms. While Taq-B created a flap that was cut to produce the required 5' phosphorylated end for the ligation by E. coli ligase, DNA polymerase I removed nucleotides one by one in front of the growing strand and generated the 5' phosphorylated nucleotide which was the perfect substrate for E. coli ligase to join the two fragments. DNA polymerase I can be used to perform 5' adapter ligation mediated by nick translation.

Example 9

Polishing is Required for Blunt Ligation of Physically Sheared DNA and Dephosphorylation Prevents the Formation of Chimeric Ligation Products

Rationale:

This experiment demonstrates the importance of end polishing and dephosphorylation for blunt ligation of adapters to physically sheared DNA substrates.

Materials:

Blue Buffer (Enzymatics, cat# B0110)
T4 DNA Ligase (Rapid) (Enzymatics, cat# L6030-HC-L)
10×T4 DNA Ligase Buffer (Enzymatics, cat# B6030)
100 mM 2'-deoxynucleoside 5'-triphosphate (dNTP) Set, PCR Grade (Invitrogen (Life technologies), cat#10297-018)
Adenosine 5'-Triphosphate (ATP) (New England Biolabs, cat# P0756S)
DNA Polymerase I, Large (Klenow) Fragment (New England Biolabs, cat#M0210S)
T4 DNA polymerase (New England Biolabs, cat# M0203S)
T4 Polynucleotide Kinase (New England Biolabs, cat# M0201S)
Shrimp alkaline phosphatase (Affymetrix, cat#78390)
T4 DNA Ligase (Rapid) (Enzymatics, cat# L6030-HC-L)
10×T4 DNA Ligase Buffer (Enzymatics, cat# B6030)
E. coli genomic DNA ATCC 11303 strain (Affymetrix, cat#14380)
M220 Focused-ultrasonicator, (Covaris, cat# PN 500295)
Pippin Prep (Sage Science)
DNA Clean & Concentrator-5-(Zymo research, cat#D4004)
CDF2010 2% agarose, dye free w/internal stds (Sage Science)

Method:

E. coli gDNA was resuspended in DNA suspension buffer (Teknova, cat#T0227) at a concentration of 100 ng/ul. The DNA was fragmented with the M220 Focused-ultrasonicator to 150 base pairs average size. A tight distribution of fragmented DNA from ~150 bp to ~185 bp was subsequently size-selected from a 2% agarose gel using pippin prep.

In a set of reactions A, 100 ng or 500 ng of the size-selected DNA was subjected to the activity of polishing enzymes. The reactions were assembled in a total volume of 30 μl, comprising a final concentration of 1× Blue buffer, 100 μM of each dNTP, 3 units T4 DNA Polymerase, 5 units DNA Polymerase I, Large (Klenow) Fragment, 1 mM ATP, 10 units of T4 Polynucleotide Kinase. The reactions were incubated at 30° C., for 20 minutes. The DNA was purified using the DNA Clean & Concentrator-5 columns. The DNA was eluted in 15 μl of DNA suspension buffer and a subsequent dephosphorylation reactions B was followed by adapter ligation or were placed directly into the ligation reaction without dephosphorylation. The dephosphorylation reactions were assembled in a 30 μl final volume, including the processed DNA, 1× Blue buffer, and 1 unit of shrimp alkaline phosphatase. The reactions were incubated at 37° C., for 10 minutes. The DNA was purified using the DNA Clean & Concentrator-5 columns and eluted in 15 μl of DNA suspension buffer.

In a set of reactions C, 100 ng of the size-selected DNA was subjected to dephosphorylation followed by polishing or directly to polishing in a set of reaction D. The dephosphorylation reactions were assembled in a 30 μl final volume, including the processed DNA, 1× Blue buffer, and 1 unit of shrimp alkaline phosphatase. The reactions were incubated at 37° C., for 10 minutes. The DNA was purified using the DNA Clean & Concentrator-5 columns and eluted in 15 μl of DNA suspension buffer. The polishing reactions D were assembled in a total volume of 30 μl, comprising a final concentration of 1× Blue buffer, 100 μM of each dNTP, 3 units T4 DNA polymerase, 5 units DNA Polymerase I, Large (Klenow) Fragment, (lanes 6 to 7). The DNA was purified using the DNA Clean & Concentrator-5 columns and eluted in 15 μl of DNA suspension buffer.

After purification, all the previous reactions were subject to ligation reactions. Reactions were assembled in a final volume of 30 μl, comprising the processed DNA, 1×T4 DNA ligase reaction buffer and 1200 units of T4 DNA ligase. The reactions were incubated at 25° C., for 15 minutes. 33 ng of DNA from each ligation was mixed with 2× formamide loading buffer (97% formamide, 10 mM EDTA, 0.01% bromophenol blue and 0.01% xylene cyanol), heated at 95° C. for 5 minutes and subsequently run on a pre-cast 15% polyacrylamide gel, TBE-Urea (Invitrogen, Cat# S11494) in an oven at 65° C., stained with SYBR Gold, visualized on a Dark reader light box (Clare Chemical Research) and photographed using a digital camera.

Results:

Before polishing, physically sheared DNA was not a suitable substrate for ligation to blunt ended adapters by T4 DNA ligase (FIG. 27, lane 1). After polishing with T4 Polynucleotide Kinase, T4 DNA polymerase and Klenow fragment, the DNA ends were blunt, some 5' termini were phosphorylated and the molecules could concatenate or ligate to each other as well as to the blunt adapters (FIG. 27, lanes 2 and 4). The species at ~325 bases, ~500 bases and over 500 bases correspond to the ligation of 2 molecules, 3 molecules and 4 molecules of ~175 bases together, respectively (FIG. 27, lanes 2 and 4). The concentration of DNA influenced the formation of ligation products. At higher concentration of DNA, the chimeric ligation species of higher molecular weight were more abundant (FIG. 27, lane 4). Treatment of DNA with shrimp alkaline phosphatase after the polishing step impaired concatamer formation between DNA molecules (FIG. 27, lanes 3 and 5). Treatment with shrimp alkaline phosphatase also prevented concatamer formation if it was performed before the polishing of the fragmented DNA (FIG. 27, lane 6). The ligation products observed after polishing with T4 DNA polymerase and klenow fragment (FIG. 27, lane 7) were not as abundant compared to the polishing with T4 DNA polymerase, klenow and T4 Polynucleotide Kinase (FIG. 27, lane 2).

Conclusion:

Blunt ligation efficiency of physically sheared DNA depended on end polishing by DNA polymerases. The ligation was also improved by the addition of T4 Polynucleotide Kinase, which phosphorylated the 5' terminus of the DNA fragments and dephosphorylated the 3' terminus. The concentration of DNA also influenced the amount of ligation and the formation of chimeric products. At higher concentration, DNA is more likely to form chimeric products in the presences of T4 DNA ligase. Alkaline phosphatases remove 5' phosphates (which are required for ligation) and prevent the formation of chimeric ligation products (concatamers).

Example 10

NGS Libraries have Increased Yield when Prepared Using 5' Base Trimming Coupled to Adapter Ligation Reaction Rationale:

This experiment demonstrates the utility of the reactions presented in their exemplary application to NGS library construction, particularly the increase in library yield that results from including 5' base trimming coupled to 5' adapter ligation. Libraries were constructed from size-selected sheared DNA so library products could be easily visualized by gel electrophoresis.

Materials:

Blue Buffer (Enzymatics, cat# B0110)
T4 DNA Ligase (Rapid) (Enzymatics, cat# L6030-HC-L)
10×T4 DNA Ligase Buffer (Enzymatics, cat# B6030)
100 mM 2'-deoxynucleoside 5'-triphosphate (dNTP) Set, PCR Grade (Invitrogen (Life technologies), cat#10297-018)
Adenosine 5'-Triphosphate (ATP) (New England Biolabs, cat# P0756S)
Klenow Fragment (Enzymatics, cat# P7060L)
T4 DNA polymerase (Enzymatics, cat# P7080L)
T4 Polynucleotide Kinase (Enzymatics, cat# Y904L)
Shrimp alkaline phosphatase (Affymetrix, cat#78390)
T4 DNA Ligase (Rapid) (Enzymatics, cat# L6030-HC-L)
10×T4 DNA Ligase Buffer (Enzymatics, cat# B6030)
3'Adapter; $1^{st}$ oligonucleotide 13-501 (Table 1)
3'Adapter; $2^{nd}$ oligonucleotide 13-712 (Table 1)
E. coli genomic DNA ATCC 11303 strain (Affymetrix, cat#14380)
M220 Focused-ultrasonicator, (Covaris, cat# PN 500295)
E. coli DNA ligase (Enzymatics, cat# L6090L)
E. coli DNA ligase buffer (Enzymatics, cat# B6090)
Uracil-DNA glycosylase (Enzymatics, cat# G5010L)
Taq-B DNA polymerase (Enzymatics, cat# P7250L)
5' adapter oligonucleotide for nick-translation (13-489) (Table 1)
5' adapter oligonucleotide for displacement-cleavage (13-595) (Table 1)
Taq DNA ligase (Enzymatics, cat# L6060L)
SPRIselect (Beckman coulter, cat# B23419)

Methods:

E. coli genomic DNA was resuspended in DNA suspension buffer (Teknova, cat#T0227) at a concentration of 100 ng/µl. The DNA was fragmented with the M220 Focused-ultrasonicator to 150 base pairs average size. A tight distribution of fragmented DNA from ~150 bp to ~185 bp was subsequently size-selected on a 2% agarose gel using pippin prep.

100 ng of the size-selected E. coli genomic DNA was used to prepare a library with the enhanced adapter ligation method. The polishing reaction was assembled in 30 l, comprising a final concentration of 1× Blue buffer, 100 µM of each dNTP, 3 units T4 DNA polymerase, 5 units DNA Polymerase I, Large (Klenow) Fragment, 10 units of T4 Polynucleotide Kinase. The reaction was incubated at 37° C. for 20 minutes. The DNA was purified using the DNA Clean & Concentrator-5 and eluted in 15 µl with DNA suspension buffer. The 3' Adapter ligation reaction was assembled in 30 µl including, 1×T4 DNA ligase buffer, 220 pmoles of the 3' Adapter 1st oligonucleotide, 440 pmoles of the 3' Adapter 2nd oligonucleotide, the 15 µl of DNA purified and 1200 units of T4 DNA ligase. The reaction was incubated at 25° C. for 15 minutes. The DNA was brought up to a 50 µl volume and purified and size selected using 70 µl SPRIselect beads (ratio 1.4×). DNA was eluted in 15 µl of DNA resuspension buffer. The partial degradation of the 3' adapter, annealing of the 5' adapter, 5'-end trimming and ligation of the 5' adapter all took place in the next reaction which was assembled in a final volume of 30 µl containing 1×E. coli DNA ligase buffer or 1× Taq DNA ligase buffer, 200 µM of each dNTPs or 200 µM of each dATP, dTTP, dGTP or no dNTPs, 200 pmoles of 5' adapter oligonucleotide for nick-translation or 5' adapter oligonucleotide for displacement-cleavage, 10 units of E. coli ligase or 40 units of Taq DNA ligase, 2 units of uracil-DNA glycosylase, 10 units of Taq-B DNA polymerase and 15 µl of the DNA purified after the 3' Adapter ligation reaction. The reaction was incubated at 40° C. or 45° C. for 10 minutes or with 30 cycles of (45° C. for 45 seconds-65° C. for 5 seconds) (library 5). The DNA was brought up to a 50 µl volume and purified and size selected using 40 µl of SPRIselect beads (ratio 0.8×). The DNA was eluted in 20 µl and quantified by qPCR using the Kapa Library Quantification Kit—Illumina/Universal (cat#KK4824).

Results:

The library concentrations were reported on the plot (FIG. 28, panel A) and the libraries were visualized on a 6% polyacrylamide gel by electrophoresis under denaturing conditions (FIG. 28, panel B). The input DNA migrated between ~150 bases and ~185 bases (FIG. 28, lane I, panel B). An aliquot was taken after the 3' adapter ligation step and loaded on the gel. This product migrated between ~225 to ~250 bases, which corresponds to the addition of the 64 bases of the 3' Adapter (FIG. 28, lane L, panel B). The contribution of Taq-B DNA polymerase in removing one or more bases and exposing a 5'phosphate group at the 5' terminus of the DNA prior to ligation of the 5' adapter was demonstrated in library 1 vs. 2 (FIG. 28, lanes 1 and 2, panels A and B). The concentration of library 1 made without Taq-B (2.6 nM) is three times lower than library 2 made with Taq-B DNA polymerase (7.9 nM). Even after treatment with T4 Polynucleotide Kinase, 75% of the fragmented DNA required processing of their 5' termini in order to be ligation compatible. The finished libraries were also loaded on the gel (FIG. 28, lanes 1 and 2, panel B). These libraries migrated between ~275 bases and ~300 bases which correspond to the addition of the 58 bases of the 5' adapter oligonucleotide for nick-translation or 5' adapter oligonucleotide for displacement-cleavage and the 64 bases of the 3' adapter. Library 1 product was present at a lower intensity than the library 2 bands (FIG. 28, panel B). The libraries 3 and 4 were made with dATP, dTTP, dGTP and E. coli ligase or Taq DNA ligase, respectively, during the partial degradation of the 3' adapter, the annealing of the 5' adapter, the 5'-end trimming and the ligation of the 5' adapter step. Library 3 concentration (4.8 nM) was about 60% of library 2 (7.9 nM). This loss of 30% in yield is related to the percent of cytosine "C" in the E. coli genome (25%). Every time the 5' terminus of the DNA substrate is a cytosine, the 5' adapter oligonucleotide for nick-translation cannot be extended by Taq and the 5' terminus cannot be trimmed. There is also an extra 6.25% and 1.5% probability to have two and three consecutive cytosines, respectively, at the 5' terminus of the DNA substrate. The ligation at 45° C. with Taq DNA ligase (library 4) gave a similar yield (4.8 nM) when compared with E. coli ligase at 40° C. (5.2 nM) (library 3). Library 5, which was made with 5' adapter oligonucleotide for displacement-cleavage, (4.2 nM) was less efficient than library 2 made with the 5' adapter oligonucleotide for nick-translation (7.9 nM).

Conclusion:

Libraries were successfully made with the disclosed adapter ligation method. The 5'-end DNA trimming by Taq DNA polymerase allows a three-fold increase in the yield of 5' adapter ligation product when compared to libraries that have no 5' end processing step (libraries 1 vs 2). Both Taq DNA ligase (library 4) and *E. coli* ligase (library 3) efficiently ligated the 5' adapter after the nick-translation. Taq DNA ligase also ligated the 5' adapter after the displacement-cleavage (library 5). Using 4 dNTPs (library 2) instead of 3 (libraries 3 and 4) during the nick-translation may allow the ligation of more DNA substrate to the 5' adapter.

Example 11

Sequence Analysis of NGS Libraries Prepared Using 5' Base Trimming Coupled to Adapter Ligation Rationale:

This experiment demonstrates the utility of the reactions presented in their exemplary application to NGS library construction. Libraries were constructed from sheared *E. coli* DNA and then sequenced in order to demonstrate the superior evenness of coverage obtained over a wide base composition of the genome.

Materials:

Blue Buffer (Enzymatics, cat# B0110)
T4 DNA Ligase (Rapid) (Enzymatics, cat# L6030-HC-L)
10×T4 DNA Ligase Buffer (Enzymatics, cat# B6030)
100 mM 2'-deoxynucleoside 5'-triphosphate (dNTP) Set, PCR Grade (Invitrogen (Life technologies), cat#10297-018)
Adenosine 5'-Triphosphate (ATP) (New England Biolabs, cat# P0756S)
Klenow Fragment (Enzymatics, cat# P7060L)
T4 DNA polymerase (Enzymatics, cat# P7080L)
T4 Polynucleotide Kinase (Enzymatics, cat# Y904L)
Shrimp alkaline phosphatase (Affymetrix, cat#78390)
T4 DNA Ligase (Rapid) (Enzymatics, cat# L6030-HC-L)
10×T4 DNA Ligase Buffer (Enzymatics, cat# B6030)
3'Adapter; $1^{st}$ oligonucleotide 13-510 (Table 1)
3'Adapter; $2^{nd}$ oligonucleotide 13-712 (Table 1)
*E. coli* genomic DNA ATCC 11303 strain (Affymetrix, cat#14380)
M220 Focused-ultrasonicator, (Covaris, cat# PN 500295)
*E. coli* DNA ligase (Enzymatics, cat# L6090L)
*E. coli* DNA ligase buffer (Enzymatics, cat# B6090)
Uracil-DNA glycosylase (Enzymatics, cat# G5010L)
Taq-B DNA polymerase (Enzymatics, cat# P7250L)
5' adapter oligonucleotide for nick-translation (13-489)
SPRIselect (Beckman coulter, cat# B23419)

Method:

*E. coli* genomic DNA was resuspended in DNA suspension buffer (Teknova, cat#T0227) at a concentration of 100 ng/μl. The DNA was fragmented with the M220 Focused-ultrasonicator to 150 base pairs average size. 100 ng of *E. coli* covaris genomic DNA was used to prepare a library. A first reaction of dephosphorylation was assembled in a total volume of 15 μl, comprising a final concentration of 1× Blue buffer, 100 ng of fragmented *E. coli* genomic DNA and 1 unit of shrimp alkaline phosphatase. The reaction was incubated at 37° C. for 10 minutes. The shrimp alkaline phosphatase was inactivated 5 minutes at 65° C. The polishing reaction was assembled in 30 μl, comprising a final concentration of 1× Blue buffer, 100 μM of each dNTP, 3 units T4 DNA polymerase, 5 units DNA Polymerase I, Large (Klenow) Fragment and 15 μl of the dephosphorylation reaction. The reaction was incubated at 20° C. for 30 minutes. The DNA was purified using the DNA Clean & Concentrator-5. The DNA was eluted in 15 μl with DNA suspension buffer. The 3' Adapter ligation reaction was assembled in 30 μl including, 1×T4 DNA ligase buffer, 220 pmoles of the 3' Adapter 1st oligonucleotide, 440 pmoles of the 3' Adapter 2nd oligonucleotide, the 15 μl of DNA purified after polishing and 1200 units of T4 DNA ligase. The reaction was incubated at 25° C. for 15 minutes. After adjusting volume to 50 μl, the DNA was purified and sized selected using 45 μl SPRIselect beads (ratio 0.9×). DNA was eluted in 15 μl of DNA resuspension buffer. The partial degradation of the 3' adapter, annealing of the 5' adapter, 5'-end DNA trimming and ligation of the 5' adapter all took place in the next reaction which was assembled in a final volume of 30 μl containing 1×*E. coli* DNA ligase, 200 μM of each dNTPs, 200 pmoles of 5' adapter oligonucleotide for nick-translation, 10 units of *E. coli* ligase, 2 units of uracil-DNA glycosylase, 10 units of Taq-B DNA polymerase and 15 μl of the DNA purified after the 3' Adapter ligation reaction. The reaction was incubated at 40° C. for 10 minutes. After adjusting the volume to 50 μl, the DNA was purified using 70 μl of SPRIselect beads (ratio 1.4×). The DNA was eluted in 20 μl, and quantified by qPCR using the Kapa Library Quantification Kit—Illumina/Universal (cat# KK4824). DNA was denatured 5 minutes with a final concentration of 0.1 mM of sodium hydroxide and 600 μl of 10 pM library was loaded on a MiSeq (Illumina).

Results:

The library concentration as quantified by qPCR was 2.8 nM. Pair end reads of 76 bases were generated by the v2 chemistry of the Illumina MiSeq. 928K/mm$^2$ clusters were generated and the Q30 score were 97.8% and 96.9% for the first and second read, respectively. The sequence data quality was assessed using the FastQC report (Babraham Bioinformatics). A summary of the analysis showed 9 green check marks, 2 yellow exclamation points (warning), but no red X (failed) were observed (FIG. 29, panel A). The overall % GC of all bases in all sequences was 50%, as expected for *E. coli* genome (Green check marks, FIG. 29, panel B). The quality of the sequence was excellent at every read throughout the 76 bases analyzed (Green check mark, FIG. 29, panel C). The percentage of each base was plotted in panel D. The amount of G/C and A/T had <10% difference at any read (Green check mark, FIG. 29, panel D). The GC content was similar throughout the 76 bases analyzed (green check mark, FIG. 29, panel E). The GC content per read across the length of each sequence was compared to a theoretical distribution (yellow exclamation point, FIG. 29, panel F). A warning was raised because the sum of the deviations from the normal distribution was found in more than 15% of the reads (yellow exclamation point, FIG. 29, panel F). No warnings were raised for the Per base N content or the Sequence Length Distribution (summary, FIG. 29, panel A). The sequence duplication level was 35.85% (FIG. 29, panel G). A yellow warning was raised because non-unique sequences make up more than 20% of the total, due to the high level of coverage 135× (Yellow exclamation point, FIG. 29, panel G). No overrepresented sequences or kmer were reported (summary, FIG. 29, panel A). Virtually, no adapter dimer where observed (0.02%, data not shown). The GC bias was also evaluated using the Picard CollectGcBiasMetrics. Evenness of coverage was preserved throughout a broad range of base composition. Deviations in coverage were only observed at lower than 10% GC content or higher than 80%. The base quality was over Q25 which correspond to 99.8% accuracy in the base calling. Again, the lower quality was only observed at extreme low and high GC content.

Conclusion:

A library was successfully made using fragmented *E. coli* genomic DNA. The sequencing demonstrated high quality data and no bias in the coverage throughout the range of GC content.

Example 12

Sequence Analysis of Ultra-Low Input NGS Libraries Prepared Using 5' Base Trimming Coupled to Adapter Ligation in Either the Presence or Absence of an Adapter Dimer Hairpin Blocker Mixture Rationale:

This experiment demonstrates the utility of the adapter dimer blocker reagent in reducing adapter dimer formation during NGS library construction at ultra-low DNA input. Libraries were constructed from 10 pg sheared human DNA and then sequenced to demonstrate the improved sequence output obtained (as a result of reducing adapter dimers) when an adapter dimer blocker was incorporated into the 5' adapter ligation step over that where the blocker was excluded.

Materials:
Blue Buffer (Enzymatics, cat# B0110)
T4 DNA Ligase (Rapid) (Enzymatics, cat# L6030-HC-L)
10×T4 DNA Ligase Buffer (Enzymatics, cat# B6030)
100 mM 2'-deoxynucleoside 5'-triphosphate (dNTP) Set, PCR Grade (Invitrogen (Life technologies), cat#10297-018)
Adenosine 5'-Triphosphate (ATP) (New England Biolabs, cat# P0756S)
Klenow Fragment (Enzymatics, cat# P7060L)
T7 DNA polymerase (Enzymatics, cat# P7260L)
3'Adapter; 1st oligonucleotide Index #1, 13-501 and Index #4, 13-508 (Table 1)
3'Adapter; 2nd oligonucleotide 13-712 (Table 1)
Hapmap human genomic DNA (Coriell, cat # NA12878)
M220 Focused-ultrasonicator, (Covaris, cat# PN 500295)
*E. coli* DNA ligase (Enzymatics, cat# L6090L)
*E. coli* DNA ligase buffer (Enzymatics, cat# B6090)
Uracil-DNA glycosylase (Enzymatics, cat# G5010L)
Taq-B DNA polymerase (Enzymatics, cat# P7250L)
5' adapter oligonucleotide for nick-translation (13-489)
SPRIselect (Beckman coulter, cat# B23419)
Calf intestinal phosphatase (Promega, cat #M182A)
Promega CIP buffer (cat# M183A)
Adapter dimer blocker (blunt) 14-19 (Table 1)
Adapter dimer blocker (N-overhang) 14-20 (Table 1)
KAPA 2× HiFi HotStart ReadyMix (KAPA Biosystems, cat# KK2601)
PCR amplification primer pair (13-164 and 13-641) (Table 2)

Method:

Human genomic DNA was resuspended in DNA suspension buffer (Teknova, cat#T0227) at a concentration of 30 ng/µl. The DNA was fragmented with the M220 Focused-ultrasonicator to 200 base pairs average size. Two NGS libraries were prepared using 10 picograms each of human Covaris sheared genomic DNA.

A first reaction of dephosphorylation was assembled in a total volume of 60 µl each, comprising a final concentration of 1×CIP buffer, 10 pg of fragmented human genomic DNA and 1 unit of calf intestinal phosphatase. The reaction was incubated at 37° C. for 10 minutes. A SPRI bead based cleanup was performed at a 1.2× ratio with 72 µl beads and a final elution volume of 30 µl.

Each 30 µl eluate was assembled in a polishing reaction of 50 µl, comprising a final concentration of 1× Blue buffer, 100 µM of each dNTP, 10 units T7 DNA polymerase and 5 units DNA Polymerase I, Large (Klenow) Fragment. The reaction was incubated at 20° C. for 20 minutes. The DNA was purified using a SPRI ratio of 1.0× (50 ul beads) and a final elution volume of 20 µl.

Each 3' Adapter ligation reaction was assembled in 30 µl including, 1×T4 DNA ligase buffer, 220 pmoles of the 3' Adapter 1st oligonucleotide, 440 pmoles of the 3' Adapter 2nd oligonucleotide, the 20 µl of DNA purified after polishing and 1200 units of T4 DNA ligase. The reaction was incubated at 25° C. for 15 minutes. After adjusting volume to 50 µl, the DNA was purified and sized selected using 40 µl SPRIselect beads (ratio 0.8×). DNA was eluted in 30 µl of DNA resuspension buffer.

The partial degradation of the 3' adapter, annealing of the 5' adapter, 5'-end DNA trimming and ligation of the 5' adapter all took place in the next reaction which was assembled in a final volume of 50 µl each. The reaction contained 1×*E. coli* DNA ligase buffer, 200 µM of each dNTPs, 200 pmol of 5' adapter oligonucleotide for nick-translation, 10 units of *E. coli* ligase, 2 units of uracil-DNA glycosylase, 10 units of Taq-B DNA polymerase and the DNA purified after the 3' Adapter ligation reaction. In one of the two reactions, an equimolar mixture of the two adapter dimer blocker oligonucleotides at a 2 µM concentration was additionally added. The reactions were incubated at 40° C. for 10 minutes. After adjusting the volume to 50 µl, the DNA was purified using 60 µl of SPRIselect beads (ratio 1.2×).

The DNA was eluted in 20 µl and subjected to 15 cycles of PCR using 2×KAPA HiFi HotStart Readymix with a hot start of 45 seconds at 98° C., and cycles of [15 seconds at 98° C.; 30 seconds at 60° C.; 60 seconds at 72° C.] followed by a final 60 second incubation at 72° C. The amplified DNA was subjected to a 1.2×SPRI cleanup and eluted in 20 µl, and quantified by qPCR using the Kapa Library Quantification Kit—Illumina/Universal (cat#KK4824). DNA library was denatured 5 minutes with a final concentration of 0.1 mM of sodium hydroxide and 600 µl of pooled 10 pM libraries were loaded on a MiSeq (Illumina).

Results:

The library concentration as quantified by qPCR was 13.7 nM for the 'minus blocker' library and 13.1 nM for the 'plus blocker' library. Paired end reads of 76 bases were generated by the v2 chemistry of the Illumina MiSeq. The sequenced reads were aligned to human reference UCSC hg19 using Bowtie 2 (Johns Hopkins University). The table below depicts the sequence data observed:

| Library | # adapter dimers | % adapter dimers | # mapped reads | % mapped reads |
|---|---|---|---|---|
| Plus blocker | 4,532/70,128 | 6% | 63,209/70,128 | 90% |
| Minus blocker | 25,348/83,408 | 30% | 55,809/83,408 | 67% |

Conclusion:

Libraries were successfully prepared and sequenced using 10 pg input of fragmented human genomic DNA. The sequencing demonstrated high output of data for the 'plus blocker' library given that adapter dimer formation was only 6% and percent mapped to the reference was 90%. The 'minus blocker' library demonstrated 30% adapter dimers which, as a result, reduced the percent mapped to the reference to only 67%. This demonstrates that when the adapter dimer blocker is added to the 5' adapter ligation step, a significant reduction (5-fold) in adapter dimer formation is observed, which significantly increases the output of sequence information obtained from libraries prepared at ultra-low input DNA quantity.

TABLE 1

| Sequence name | Sequence ID | Sequence (5→3') |
|---|---|---|
| 12-900 | 1 | AATGATACGGCGACCACCGAGATCTACACTCTTTCCCTACACGACGCTCTTCCGATCT |
| 13-426 | 2 | AGATCGGAAGAGCGTCGTGTAG/3SpC3/ |
| 13-340 | 3 | /5PHOS/AGATCGGAAGAGCGTCGTGTAGGGAAAGAGTGTAGATCTCGGTGGTCGCCGTATCATT/3SpC3/ |
| 13-559 | 4 | ACACGACGCTCTTCCGATCddT |
| 13-558 | 5 | ACACGACGCTCTTCCGATCT/3PHOS/ |
| 13-562 | 6 | /5PHOS/TGTACCTCACTTCTCATCACTGCT/3FAM/ |
| 13-563 | 7 | AGCAGTGATGAGAAGTGAGGTACA |
| 13-561 | 8 | /5PHOS/TGTACCTCACTTCTCATCACTGCT |
| 13-564 | 9 | /5FAM/AGCAGTGATGAGAAGTGAGGTACA |
| 13-560 | 10 | TGTACCTCACTTCTCATCACTGCT |
| 13-144 | 11 | GTGACTGGAGTTCAGACGTGTGCTCTTCCGATCT |
| 13-581 | 12 | TGTACCTCACTTCTCATCACTGCTGTCATCCGAT/3FAM/ |
| 13-582 | 13 | AGCAGTGATGAGAAGTGAGGTACAAGATCGGAAGAGCGTCGTGTAG/3SpC3/ |
| 13-156 | 14 | GACTGGAGTTCAGACGTGTGCTCTTCCGATCTT |
| 13-607 | 15 | CAAGCAGAAGACGGCATACGAGATCGTGATGTGACTGGAGTTCAGACGTGTGCTCTTCCGATCTT |
| 13-596 | 16 | /5SpC3/C*A*AGCAGAAGACGGCATACGAGATCGTGATGTGACTGGAGTTCAGACGTGTGCTCTTCCGATCTN |
| 13-501 | 17 | /5PHOS/AGATCGGAAGAGCACACGTCTGAACTCCAGTCACATCACGATCTCGTATGCCGTCTTCTGCT*T*G/3SpC3/ |
| 13-712 | 18 | AGACGUGUGCUCUTCCGATCddT |

TABLE 1-continued

| Sequence name | Sequence ID | Sequence (5→3') |
|---|---|---|
| 13-489 | 19 | /5SpC3/A*A*TGATACGGCGACCACCGAGATCTACACTCTTTCCCTACACGACGCTCTTCCGATCT |
| 13-595 | 20 | /5SpC3/A*A*TGATACGGCGACCACCGAGATCTACACTCTTTCCCTACACGACGCTCTTCCGATCTN |
| 13-510 | 21 | /5PHOS/AGATCGGAAGAGCACACGTCTGAACTCCAGTCACGCCAATATCTCGTATGCCGTCTTCTGCT*T*G/3spC3/ |

*Phosphorothioated DNA bases
/5SpC3/: 5' C3 spacer (IDT)
/3SpC3/: 3' C3 spacer (IDT)
/5PHOS/: 5' Phosphorylation (IDT)
/3PHOS/: 3' Phosphorylation (IDT)
/5FAM/: 5' 6-carboxyfluorescein (IDT)
/3FAM/: 3' 6-carboxyfluorescein (IDT)
ddT: 2',3'-Dideoxythymidine (TriLink)

TABLE 2

| Sequence name | Sequence ID | Sequence (5'→3') |
|---|---|---|
| blocker for nick translation ligation with abasic site | 14-19 | 22 | AGG TCA GGT ACT AGG TTT/idSp/TTC CTA GTA CCT GAC CT |
| blocker for nick translation ligation with abasic site and 3'N | 14-20 | 23 | AGG TCA GGT ACT AGG TTT/idSp/TTC CTA GTA CCT GAC CTN |
| Illumina P5 PCR primer | 13-164 | 24 | AATGATACGGCGACCACCGAGATC |
| Illumina P7 PCR primer | 13-641 | 25 | CAAGCAGAAGACGGCATACGA |
| Illumina P7 3' adapter Index 1 | 13-501 | 17 | /5Phos/AGATCGGAAGAGCACACGTCTGAACTCCAGTCACATCACGATCTCGTATGCCGTCTTCTGCT*T*G/3spC3/ |
| Illumina P7 3' adapter Index 4 | 13-508 | 26 | /5Phos/AGATCGGAAGAGCACACGTCTGAACTCCAGTCACTGACCAATCTCGTATGCCGTCTTCTGCT*T*G/3spC3/ |
| 3' adapter oligo 2 | 13-712 | 18 | AGACGUGUGCUCUTCCGATCddT |
| 5' adapter P5 Illumina | 13-489 | 19 | /5SpC3/A*A*TGATACGGCGACCACCGAGATCTACACTCTTTCCCTACACGACGCTCTTCCGATCT |

*Phosphorothioated DNA bases
/5SpC3/: 5' C3 spacer (IDT)
/3SpC3/: 3' C3 spacer (IDT)
/5PHOS/: 5' Phosphorylation (IDT)
/3PHOS/: 3' Phosphorylation (IDT)
ddT: 2',3'-Dideoxythymidine (TriLink)

The preceding disclosure is supplemented by the following description of various aspects and embodiments of the disclosure, as provided in the following enumerated paragraphs.

1. A method of producing a processed substrate molecule, the method comprising:
   (i) ligating a first polynucleotide to a 3' terminus of a substrate molecule that is at least partially double stranded;
   (ii) annealing a second polynucleotide to the first polynucleotide under conditions that promote the annealing;
   (iii) excising at least one nucleotide from the 5' terminus of the substrate molecule; and then
   (iv) ligating the second polynucleotide to the 5' terminus of the double stranded substrate molecule to produce the processed substrate molecule.

2. The method of paragraph 1, further comprising the step, prior to step (i), of contacting the substrate molecule with a phosphatase enzyme.

3. The method of paragraph 2, further comprising the step of making the substrate molecule blunt-ended by contacting the substrate molecule with a polymerase enzyme possessing 3'-5' exonuclease activity.

4. The method of paragraph 3, further comprising the step of contacting the substrate molecule with a template-independent polymerase to adenylate the 3' end of the substrate molecule.

5. The method of any one of paragraphs 1-4 wherein the substrate molecule is naturally occurring or the substrate molecule is synthetic.

6. The method of paragraph 5 wherein the substrate molecule is naturally occurring.

7. The method of paragraph 6 wherein the substrate molecule is genomic DNA.

8. The method of paragraph 7 wherein the genomic DNA is eukaryotic or prokaryotic.

9. The method of paragraph 7 or paragraph 8 wherein the genomic DNA is fragmented in vitro or in vivo.

10. The method of paragraph 9 wherein the in vitro fragmenting is performed by a process selected from the group consisting of shearing, cleaving with an endonuclease, sonication, heating, irradiation using an alpha, beta, or gamma source, chemical cleavage in the presence of metal ions, radical cleavage, and a combination thereof.

11. The method of paragraph 9 wherein the in vivo fragmenting occurs by a process selected from the group consisting of apoptosis, radiation, and exposure to asbestos.

12. The method of paragraph 5 wherein the substrate molecule is synthetic and is selected from the group consisting of cDNA, DNA produced by whole genome amplification, primer extension products comprising at least one double-stranded terminus, and a PCR amplicon.

13. The method of any one of paragraphs 1-12 wherein the first polynucleotide is at least partially double stranded and comprises oligonucleotide 1 and oligonucleotide 2.

14. The method of paragraph 13 wherein the second polynucleotide anneals to oligonucleotide 1.

15. The method of paragraph 14 wherein the annealing results in a nick, a gap, or an overlapping base between the second polynucleotide and the substrate molecule.

16. The method of paragraph 14 or paragraph 15 wherein the second polynucleotide is contacted with a polymerase, resulting in degradation of oligonucleotide 2.

17. The method of any one of paragraphs 13-16 wherein oligonucleotide 2 comprises a base that is susceptible to degradation.

18. The method of paragraph 17 wherein oligonucleotide 2 is contacted with an enzyme capable of degrading oligonucleotide 2.

19. The method of paragraph 18 wherein the second polynucleotide anneals to the first polynucleotide.

20. The method of claim 19 further comprising the step of contacting the substrate molecule with a polymerase and a ligase.

21. The method of claim 19 further comprising the step of contacting the substrate molecules with a 5' flap endonuclease and a ligase.

22. The method of claim 20 further comprising the step of providing a deoxynucleotide triphosphate.

23. The method of any one of paragraphs 13-17 wherein oligonucleotide 2 comprises a blocking group at its 3' end that prevents ligation.

24. The method of any one of paragraphs 1-23 wherein the second polynucleotide comprises a modified base.

25. The method of paragraph 14 wherein the annealing results in dehybridization of oligonucleotide 1 and oligonucleotide 2.

26. The method of any one of paragraphs 1-25, further comprising:
   (i) ligating a third polynucleotide to a 3' terminus of an additional substrate molecule that is at least partially double stranded;
   (ii) annealing a fourth polynucleotide to the third polynucleotide under conditions that promote the annealing;
   (iii) excising at least one nucleotide from the 5' terminus of the additional substrate molecule; and then
   (iv) ligating the fourth polynucleotide to the 5' terminus of the double stranded additional substrate molecule to produce a processed additional substrate molecule.

27. The method of paragraph 26 wherein the first polynucleotide and the third polynucleotide are the same.

28. The method of paragraph 26 or paragraph 27 wherein the second polynucleotide and the fourth polynucleotide are the same.

29. The method of paragraph 13 wherein the second polynucleotide is absent, and oligonucleotide 2 is ligated to the 5' terminus of the substrate molecule.

30. The method of any one of paragraphs 1-12 wherein the 5' end of oligonucleotide 1 includes a phosphate group.

31. The method of paragraph 29 or 30 wherein the substrate molecule is contacted with a polymerase enzyme possessing 5'-3' exonuclease activity, a deoxynucleotide, and a ligase.

32. A method of producing a processed substrate molecule, the method comprising:
   (i) ligating a polynucleotide 1 to a 5' terminus of a substrate molecule that is at least partially double stranded;
   (ii) annealing a polynucleotide 2 to polynucleotide 1 under conditions that promote the annealing;
   (iii) excising at least one nucleotide from the 5' terminus of the polynucleotide 2; and then
   (iv) ligating polynucleotide 2 to the 3' terminus of the double stranded substrate molecule to produce the processed substrate molecule.

33. The method of paragraph 32, further comprising the step of making the substrate molecule blunt-ended by contacting the substrate molecule with a polymerase enzyme possessing 3'-5' exonuclease activity.

34. The method of paragraph 33, further comprising the step of contacting the substrate molecule with a template-independent polymerase to adenylate the 3' end of the substrate molecule.

35. The method of any one of paragraphs 32-34 wherein the substrate molecule is naturally occurring or the substrate molecule is synthetic.

36. The method of paragraph 35 wherein the substrate molecule is naturally occurring.

37. The method of paragraph 36 wherein the substrate molecule is genomic DNA.

38. The method of paragraph 37 wherein the genomic DNA is eukaryotic or prokaryotic.

39. The method of paragraph 37 or paragraph 38 wherein the genomic DNA is fragmented in vitro or in vivo.

40. The method of paragraph 39 wherein the in vitro fragmenting is performed by a process selected from the group consisting of shearing, cleaving with an endonuclease, sonication, heating, irradiation using an alpha, beta, or gamma source, chemical cleavage in the presence of metal ions, radical cleavage, and a combination thereof.

41. The method of paragraph 39 wherein the in vivo fragmenting occurs by a process selected from the group consisting of apoptosis, radiation, and exposure to asbestos.

42. The method of paragraph 35 wherein the substrate molecule is synthetic and is selected from the group consisting of cDNA, DNA produced by whole genome amplification, primer extension products comprising at least one double-stranded terminus, and a PCR amplicon.

43. The method of any one of paragraphs 32-42 wherein polynucleotide 1 is at least partially double stranded and comprises oligonucleotide a and oligonucleotide b.

44. The method of paragraph 43 wherein polynucleotide 2 anneals to oligonucleotide a.

45. The method of paragraph 44 wherein the annealing results in a nick, a gap, or an overlapping base between polynucleotide 2 and the substrate molecule.

46. The method of any one of paragraphs 43-45 wherein oligonucleotide b comprises a base that is susceptible to degradation.

47. The method of paragraph 46 wherein oligonucleotide b is contacted with an enzyme capable of degrading oligonucleotide b.

48. The method of paragraph 47 wherein the polynucleotide 2 anneals to polynucleotide 1.

49. The method of claim 48 further comprising the step of contacting the substrate molecule with a polymerase, a deoxynucleotide triphosphate, and a ligase.

50. The method of claim 48 further comprising the step of contacting the substrate molecule with a 5' flap endonuclease and a ligase.

51. The method of any one of paragraphs 40-44 wherein oligonucleotide b lacks a 5' phosphate group.

52. The method of any one of paragraphs 32-51 wherein polynucleotide 2 comprises a modified base.

53. The method of paragraph 44 wherein the annealing results in dehybridization of oligonucleotide a and oligonucleotide b.

54. The method of any one of paragraphs 32-53 wherein polynucleotide 2 lacks a 5' phosphate.

What is claimed is:

1. A method of producing a processed substrate nucleic acid molecule, the method comprising:
   (1) adding a first polynucleotide and a ligase to a sample comprising a substrate nucleic acid molecule, wherein the substrate nucleic acid molecule is at least partially double-stranded and has a phosphate at its 5' ends, wherein the first polynucleotide comprises oligonucleotide A, oligonucleotide B, and a double-stranded portion, wherein the double-stranded portion comprises oligonucleotide A hybridized to oligonucleotide B, wherein oligonucleotide A lacks a 5' phosphate and comprises a base that is susceptible to degradation;
   (2) incubating the sample under conditions sufficient to ligate oligonucleotide B to the 5' ends of the substrate nucleic acid molecule;
   (3) adding to the sample a second polynucleotide, an enzyme capable of degrading oligonucleotide A, a DNA polymerase, deoxynucleotide triphosphates, wherein the second polynucleotide lacks a 5' phosphate and is capable of annealing to a 3' portion of oligonucleotide B, and wherein the DNA polymerase is capable of nick-translation DNA synthesis; and
   (4) incubating the sample under conditions sufficient to (i) promote degradation of oligonucleotide A by the enzyme, (ii) promote annealing of the second polynucleotide to oligonucleotide B and (iii) allow the DNA polymerase and ligase to act on the substrate nucleic acid molecule in order to add the second polynucleotide to the 3' ends of the substrate nucleic acid molecule thereby forming the processed substrate nucleic acid molecule.

2. The method of claim 1, wherein the substrate nucleic acid molecule is genomic DNA.

3. The method of claim 2, wherein the genomic DNA is eukaryotic or prokaryotic.

4. The method of any one of claims 1-3, wherein the substrate nucleic acid molecule is synthetic and is selected from the group consisting of cDNA, DNA produced by whole genome amplification, primer extension products comprising at least one double-stranded terminus, and a PCR amplicon.

5. The method of any one of claims 1-4, wherein the deoxynucleotide triphosphates comprise no more than three different types of deoxynucleotide triphosphates.

6. The method of claim 1, further comprising a purification step after step (2), wherein the purification step removes any unused first polynucleotide.

7. The method of claim 6, wherein step (3) further comprises adding ligase to the sample.

\* \* \* \* \*

SEQUENCE LISTING

```
<160> NUMBER OF SEQ ID NOS: 26

<210> SEQ ID NO 1
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 1
aatgatacgg cgaccaccga gatctacact ctttccctac acgacgctct tccgatct          58

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (22)..(22)
<223> OTHER INFORMATION: 3' C3 spacer (IDT)

<400> SEQUENCE: 2
agatcggaag agcgtcgtgt ag                                                 22

<210> SEQ ID NO 3
<211> LENGTH: 58
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
```

<223> OTHER INFORMATION: 5' Phosphorylation (IDT)
<220> FEATURE:
<221> NAME/KEY: misc_feature
<222> LOCATION: (58)..(58)
<223> OTHER INFORMATION: 3' C3 spacer (IDT)

<400> SEQUENCE: 3
agatcggaag agcgtcgtgt agggaaagag tgtagatctc ggtggtcgcc gtatcatt       58

<210> SEQ ID NO 4
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (19)..(19)
<223> OTHER INFORMATION: 3'- Dideoxythymidine  (TriLink)

<400> SEQUENCE: 4
acacgacgct cttccgatc                                                  19

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (20)..(20)
<223> OTHER INFORMATION: 3' Phosphorylation (IDT)

<400> SEQUENCE: 5
acacgacgct cttccgatct                                                 20

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' Phosphorylation (IDT)

<400> SEQUENCE: 6
tgtacctcac ttctcatcac tgct                                            24

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 7
agcagtgatg agaagtgagg taca                                            24

<210> SEQ ID NO 8
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature

```
<222> LOCATION: (1)..(1)
<223> OTHER INFORMATION: 5' Phosphorylation (IDT)

<400> SEQUENCE: 8
tgtacctcac ttctcatcac tgct                                          24

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' 6-carboxyfluorescein (IDT)

<400> SEQUENCE: 9
agcagtgatg agaagtgagg taca                                          24

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 10
tgtacctcac ttctcatcac tgct                                          24

<210> SEQ ID NO 11
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 11
gtgactggag ttcagacgtg tgctcttccg atct                               34

<210> SEQ ID NO 12
<211> LENGTH: 34
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (34)..(34)
<223> OTHER INFORMATION: 3' 6-carboxyfluorescein (IDT)

<400> SEQUENCE: 12
tgtacctcac ttctcatcac tgctgtcatc cgat                               34

<210> SEQ ID NO 13
<211> LENGTH: 46
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (46)..(46)
<223> OTHER INFORMATION: 3' C3 spacer (IDT)

<400> SEQUENCE: 13
agcagtgatg agaagtgagg tacaagatcg gaagagcgtc gtgtag                  46
```

```
<210> SEQ ID NO 14
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 14
gactggagtt cagacgtgtg ctcttccgat ctt                                    33

<210> SEQ ID NO 15
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 15
caagcagaag acggcatacg agatcgtgat gtgactggag ttcagacgtg tgctcttccg       60
atctt                                                                   65

<210> SEQ ID NO 16
<211> LENGTH: 65
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' C3 spacer (IDT)
<220> FEATURE:
<221> NAME/KEY: misc_feature
<222> LOCATION: (1)..(1)
<223> OTHER INFORMATION: Phosphorothioated base
<220> FEATURE:
<221> NAME/KEY: misc_feature
<222> LOCATION: (2)..(2)
<223> OTHER INFORMATION: Phosphorothioated base
<220> FEATURE:
<221> NAME/KEY: misc_feature
<222> LOCATION: (65)..(65)
<223> OTHER INFORMATION: n is a, c, g, or t

<400> SEQUENCE: 16
caagcagaag acggcatacg agatcgtgat gtgactggag ttcagacgtg tgctcttccg       60 atctn                                                                   65

<210> SEQ ID NO 17
<211> LENGTH: 64
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' Phosphorylation (IDT)
<220> FEATURE:
<221> NAME/KEY: misc_feature
<222> LOCATION: (62)..(62)
<223> OTHER INFORMATION: Phosphorothioated base
<220> FEATURE:
<221> NAME/KEY: misc_feature
<222> LOCATION: (63)..(63)
<223> OTHER INFORMATION: Phosphorothioated base
<220> FEATURE:
<221> NAME/KEY: misc_feature
<222> LOCATION: (64)..(64)
<223> OTHER INFORMATION: 3' C3 spacer (IDT)
```

<400> SEQUENCE: 17
agatcggaag agcacacgtc tgaactccag tcacatcacg atctcgtatg ccgtcttctg    60
cttg                                                                64

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (20)..(20)
<223> OTHER INFORMATION: 2', 3'- Dideoxythymidine  (TriLink)

<400> SEQUENCE: 18
agacgugugc ucutccgatc                                                20

<210> SEQ ID NO 19
<211> LENGTH: 58
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' C3 spacer (IDT)
<220> FEATURE:
<221> NAME/KEY: misc_feature
<222> LOCATION: (1)..(1)
<223> OTHER INFORMATION: Phosphorothioated base
<220> FEATURE:
<221> NAME/KEY: misc_feature
<222> LOCATION: (2)..(2)
<223> OTHER INFORMATION: Phosphorothioated base

<400> SEQUENCE: 19
aatgatacgg cgaccaccga gatctacact ctttccctac acgacgctct tccgatct      58

<210> SEQ ID NO 20
<211> LENGTH: 59
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' C3 spacer (IDT)
<220> FEATURE:
<221> NAME/KEY: misc_feature
<222> LOCATION: (1)..(1)
<223> OTHER INFORMATION: Phosphorothioated base
<220> FEATURE:
<221> NAME/KEY: misc_feature
<222> LOCATION: (2)..(2)
<223> OTHER INFORMATION: Phosphorothioated base
<220> FEATURE:
<221> NAME/KEY: misc_feature
<222> LOCATION: (59)..(59)
<223> OTHER INFORMATION: n is a, c, g, or t

<400> SEQUENCE: 20
aatgatacgg cgaccaccga gatctacact ctttccctac acgacgctct tccgatctn     59

<210> SEQ ID NO 21
<211> LENGTH: 64
<212> TYPE: DNA

```
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' Phosphorylation (IDT)
<220> FEATURE:
<221> NAME/KEY: misc_feature
<222> LOCATION: (62)..(62)
<223> OTHER INFORMATION: Phosphorothioated base
<220> FEATURE:
<221> NAME/KEY: misc_feature
<222> LOCATION: (63)..(63)
<223> OTHER INFORMATION: Phosphorothioated base
<220> FEATURE:
<221> NAME/KEY: misc_feature
<222> LOCATION: (64)..(64)
<223> OTHER INFORMATION: 3' C3 spacer (IDT)

<400> SEQUENCE: 21
agatcggaag agcacacgtc tgaactccag tcacgccaat atctcgtatg ccgtcttctg    60
cttg                                                                64

<210> SEQ ID NO 22
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (18)..(18)
<223> OTHER INFORMATION: Int 1',2'-Dideoxyribose (dSpacer)

<400> SEQUENCE: 22
aggtcaggta ctaggttttt cctagtacct gacct                              35

<210> SEQ ID NO 23
<211> LENGTH: 36
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (18)..(18)
<223> OTHER INFORMATION: Int 1',2'-Dideoxyribose (dSpacer)
<220> FEATURE:
<221> NAME/KEY: misc_feature
<222> LOCATION: (36)..(36)
<223> OTHER INFORMATION: n is a, c, g, or t

<400> SEQUENCE: 23
aggtcaggta ctaggttttt cctagtacct gacctn                             36

<210> SEQ ID NO 24
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 24
aatgatacgg cgaccaccga gatc                                          24

<210> SEQ ID NO 25
<211> LENGTH: 21
<212> TYPE: DNA
<213> ORGANISM: Artificial Sequence
```

```
<220> FEATURE:
<223> OTHER INFORMATION: Synthetic oligonucleotide

<400> SEQUENCE: 25
caagcagaag acggcatacg a                                              21

<210> SEQ ID NO 26
<211> LENGTH: 64
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' Phosphorylation (IDT)
<220> FEATURE:
<221> NAME/KEY: misc_feature
<222> LOCATION: (62)..(62)
<223> OTHER INFORMATION: Phosphorothioated base
<220> FEATURE:
<221> NAME/KEY: misc_feature
<222> LOCATION: (63)..(63)
<223> OTHER INFORMATION: Phosphorothioated base
<220> FEATURE:
<221> NAME/KEY: misc_feature
<222> LOCATION: (64)..(64)
<223> OTHER INFORMATION: 3' C3 spacer (IDT)

<400> SEQUENCE: 26
agatcggaag agcacacgtc tgaactccag tcactgacca atctcgtatg ccgtcttctg    60
cttg                                                                 64
```